US012799531B2

(12) United States Patent
Andrews et al.

(10) Patent No.: US 12,799,531 B2
(45) Date of Patent: Nov. 17, 2026

(54) DETECTION OF GENE POLYMORPHISMS

(71) Applicant: The Board of Trustees of the Leland Stanford Junior University, Stanford, CA (US)

(72) Inventors: Jason Randolph Andrews, Menlo Park, CA (US); Renu Verma, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 934 days.

(21) Appl. No.: 17/912,177

(22) PCT Filed: Mar. 18, 2021

(86) PCT No.: PCT/US2021/023029

§ 371 (c)(1),
(2) Date: Sep. 16, 2022

(87) PCT Pub. No.: WO2021/188834

PCT Pub. Date: Sep. 23, 2021

(65) Prior Publication Data

US 2023/0132088 A1 Apr. 27, 2023

Related U.S. Application Data

(60) Provisional application No. 62/991,477, filed on Mar. 18, 2020.

(51) Int. Cl.

| | |
|---|---|
| ***C12Q 1/68*** | (2018.01) |
| ***A61K 31/4409*** | (2006.01) |
| ***C12P 19/34*** | (2006.01) |
| ***C12Q 1/6883*** | (2018.01) |

(52) U.S. Cl.

CPC ........ *C12Q 1/6883* (2013.01); *A61K 31/4409* (2013.01); *C12Q 2600/106* (2013.01); *C12Q 2600/156* (2013.01)

(58) Field of Classification Search

CPC ............ C12Q 1/6883; C12Q 2600/106; C12Q 2600/156

See application file for complete search history.

(56) References Cited

U.S. PATENT DOCUMENTS

| | | | | |
|---|---|---|---|---|
| 9,937,192 | B2 * | 4/2018 | Locher ................. | A61K 31/454 |
| 2003/0232382 | A1 | 12/2003 | Brennan et al. | |
| 2010/0068710 | A1 | 3/2010 | Buela et al. | |
| 2014/0242586 | A1 | 8/2014 | Whitman et al. | |
| 2017/0368070 | A1 | 12/2017 | Pfizer et al. | |

OTHER PUBLICATIONS

Hu, Y., et al. "Rapid Identification of the NAT2 Genotype in Tuberculosis Patients by Multicolor Melting Curve Analysis". Pharmacogenomics, 17(11), 1211-1218. (Year: 2016).*

Audrey Sabbagh, et al. "SNP selection at the NAT2 locus for an accurate prediction of the acetylation phenotype" Genet Med 2006: 8(2):76-85. (Year: 2006).*

Janice A. Nicklas, et al. "A Real-Time Multiplex SNP Melting Assay to Discriminate Individuals" Forensic Sciences. vol. 53, Issue 6, Nov. 2008. (Year: 2008).*

Yiqun Liao, et al. "Combination of fluorescence color and melting temperature as a two-dimensional label for homogeneous multiplex PCR detection" Nucleic Acids Research, vol. 41, Issue 7, Apr. 1, 2013, p. e76 (Year: 2013).*

Girish Pai, et al. "Rapid Detection of Mycobacterium Tuberculosis Complex with IS6110 Marker Based on Real Time PCR High Resolution Melting Analysis" International Journal of Health Sciences and Research, vol. 6; Issue: 1; pp. 450-458 Jan. 2016. (Year: 2016).*

Kinzig-Schippers M, Tomalik-Scharte D, Jetter A, Scheidel B, Jakob V, Rodamer M, Cascorbi I, Doroshyenko O, Sörgel F, Fuhr U. Should we use N-acetyltransferase type 2 genotyping to personalize isoniazid doses? Antimicrob Agents Chemother. May 2005;49(5):1733-8.

Du H, Chen X, Fang Y, Yan O, Xu H, Li L, Li W, Huang W. Slow N-acetyltransferase 2 genotype contributes to anti- tuberculosis drug-induced hepatotoxicity: a meta-analysis. Mol Biol Rep. May 2013;40.

Sabbagh A, Langaney A, Darlu P, Gerard N, Krishnamoorthy R, Poloni ES. Worldwide distribution of NAT2 diversity: Implications for NAT2 evolutionary history. BMC Genet. Feb. 27, 2008;9:21.

Wang PY, Xie SY, Hao Q, Zhang C, Jiang BF. NAT2 polymorphisms and susceptibility to anti-tuberculosis drug-induced liver injury: a meta-analysis. Int J Tuberc Lung Dis. May 2012;16(5):589-95.

Parkin DP, Vandenplas S, Botha FJ, Vandenplas ML, Seifart HI, van Helden PD, van der Walt BJ, Donald PR, van Jaarsveld PP. Trimodality of isoniazid elimination: phenotype and genotype in patients with tuberculosis. Am J Respir Crit Care Med. May 1997;155(5):1717-22.

Gross M, Kruisselbrink T, Anderson K, Lang N, McGovern P, Delongchamp R, Kadlubar F. Distribution and concordance of N-acetyltransferase genotype and phenotype in an American population. Cancer Epidemiol Biomarkers Prev. Aug. 1999;8(8):683-92.

Mrozikiewicz PM, Cascorbi I, Brockmoller J, Roots I. Determination and allelic allocation of seven nucleotide transitions within the arylamine N-acetyltransferase gene in the Polish population. Clin Pharmacol Ther. Apr. 1996;59(4):376-82.

Hein DW, Doll MA. Accuracy of various human NAT2 SNP genotyping panels to infer rapid, intermediate and slow acetylator phenotypes. Pharmacogenomics. Jan. 2012;13(1):31-41.

Snider DE Jr, Caras GJ. Isoniazid-associated hepatitis deaths: a review of available information. Am Rev Respir Dis. Feb. 1992;145(2 Pt 1):494-7.

(Continued)

*Primary Examiner* — Stephen T Kapushoc

(74) *Attorney, Agent, or Firm* — KDW Firm PLLC

(57) ABSTRACT

Provided herein, inter alia, are methods of detecting single polypeptide polymorphisms in a subject by detecting a G191A NAT2 SNP, a C282T NAT2 SNP, a T341C NAT2 SNP, a G590A NAT2 SNP and a G857A NAT2 SNP in a biological sample, wherein the subject is taking an arylamine drug or a hydrazine drug or the subject is in need of an arylamine drug or a hydrazine drug. The subject can have a tuberculosis infection and the drug can be isoniazid. Also provided are related kits.

10 Claims, 16 Drawing Sheets

Specification includes a Sequence Listing.

(56) References Cited

OTHER PUBLICATIONS

Azuma J, Ohno M, Kubota R, Yokota S, Nagai T, Tsuyuguchi K, Okuda Y, Takashima T, Kamimura S, Fujio Y, Kawase I; Pharmacogenetics-based tuberculosis therapy research group. NAT2 genotype guided regimen reduces soniazid-induced liver injury and early treatment failure in the 6-month four-drug standard treatment of tuberculosis: a randomized controlled trial for pharmacogenetics-based therapy. Eur J Clin Pharmacol. May 2013;69(5):1091-101.
Sabbagh A, Darlu P, Vidaud M. Evaluating NAT2PRED for inferring the individual acetylation status from unphased genotype data. BMC Med Genet. Dec. 31, 2009;10:148.
Ramachandran G, Swaminathan S. Role of pharmacogenomics in the treatment of tuberculosis: a review. Pharmgenomics Pers Med. 2012;5:89-98.
Rens NE, Uyl-de Groot CA, Goldhaber-Fiebert JD, Croda J, Andrews JR. Cost-effectiveness of a Pharmacogenomic Test for Stratified Isoniazid Dosing in Treatment of Active Tuberculosis. Clin Infect Dis. Dec. 15, 2020;71(12):3136-3143.
Sabbagh A, Darlu P, Crouau-Roy B, Poloni ES. Arylamine N-acetyltransferase 2 (NAT2) genetic diversity and traditional subsistence: a worldwide population survey. PLoS One. Apr. 6, 2011;6(4):e18507.
Mthiyane T, Millard J, Adamson J, Balakrishna Y, Connolly C, Owen A, Rustomjee R, Dheda K, McIlleron H, Pym AS. N-Acetyltransferase 2 Genotypes among Zulu-Speaking South Africans and Isoniazid and N-Acetyl-Isoniazid Pharmacokinetics during Antituberculosis Treatment. Antimicrob Agents Chemother. Mar. 24, 2020;64(4):e02376-19.
van Oosterhout JJ, Dzinjalamala FK, Dimba A, Waterhouse D, Davies G, Zijlstra EE, Molyneux ME, Molyneux EM, Ward S. Pharmacokinetics of Antituberculosis Drugs in HIV-Positive and HIV-Negative Adults in Malawi. Antimicrob Agents Chemother. Oct. 2015;59(10):6175-80.
Wilkins JJ, Langdon G, McIlleron H, Pillai G, Smith PJ, Simonsson US. Variability in the population pharmacokinetics of isoniazid in South African tuberculosis patients. Br J Clin Pharmacol. Jul. 2011;72(1):51-62.
Selius L, Evans DA. Formal genetics of isoniazid metabolism in man. Clin Pharmacokinet. Nov.-Dec. 1983;8(6):541-4.
Evans DA. Genetic variations in the acetylation of isoniazid and other drugs. Ann N Y Acad Sci. Jul. 31, 1968;151(2):723-33.
Evans DA. An improved and simplified method of detecting the acetylator phenotype. J Med Genet. Dec. 1969;6(4):405-7.
Naidoo A, Chirehwa M, Ramsuran V, McIlleron H, Naidoo K, Yende-Zuma N, Singh R, Ncgapu S, Adamson J, Govender K, Denti P, Padayatchi N. Effects of genetic variability on rifampicin and isoniazid pharmacokinetics in South African patients with recurrent tuberculosis. Pharmacogenomics. Mar. 2019;20(4):225-240.
Wilkins JJ, Langdon G, McIlleron H, Pillai GC, Smith PJ, Simonsson US. Variability in the population pharmacokinetics of pyrazinamide in South African tuberculosis patients. Eur J Clin Pharmacol. Sep. 2006;62(9):727-35.
Lee SW, Chung LS, Huang HH, Chuang TY, Liou YH, Wu LS. NAT2 and CYP2E1 polymorphisms and susceptibility to first-line anti-tuberculosis drug-induced hepatitis. Int J Tuberc Lung Dis. May 2010;14(5):622-6.
Chen et al., "The influence of NAT2 genotypes on the plasma concentration of isoniazid and acetylisoniazid in Chinese pulmonary tuberculosis patients" Clinica Chimica Acta—vol. 365, Issues 1-2, Mar. 2006, pp. 104-108 [abstract only].
International Search Report and Written Opinion for the International Patent Application No. PCT/US2021/023029, mailed Jul. 16, 2021, 11 pages.
Abouraya, Mahmoud et al. "Dapsone-associated methemoglobinemia in a patient with slow NAT2*5B haplotype and impaired cytochrome b5 reductase activity." Journal of clinical pharmacology vol. 52,2 (2012): 272-8.
Selinski, Silvia et al. "Genotyping NAT2 with only two SNPs (rs1041983 and rs1801280) outperforms the tagging SNP rs1495741 and is equivalent to the conventional 7-SNP NAT2 genotype." Pharmacogenetics and genomics vol. 21,10 (2011): 673-8.

* cited by examiner

NAT2-857 Probe

| Analyte Name | Ct | EndPt | Interpretation Result | Analyte Result | Probe Check Result |
|---|---|---|---|---|---|
| 282-Alexa647 | 28.2 | 221 | POS | POS | PASS |
| 341-Alexa532 | 27.3 | 235 | POS | POS | PASS |
| 590-FAM | 30.8 | 77 | POS | POS | PASS |
| 191-Cy5.5 | 32.2 | 90 | POS | POS | PASS |
| 857-Alexa405 | 30.4 | 63 | POS | POS | PASS |

DETECTION OF GENE POLYMORPHISMS

CROSS-REFERENCE TO RELATED APPLICATIONS

This application is a national phase application claiming the benefit of and priority to International Patent Application No. PCT/US2021/023029, entitled "DETECTION OF GENE POLYMORPHISMS," filed Mar. 18, 2021, which claims the benefit of priority under 35 U.S.C. § 119 to U.S. Provisional Application No. 62/991,477, filed Mar. 18, 2020, which is hereby incorporated by reference in its entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 60450556_ST25.txt, created on Mar. 18, 2021, 3,421 bytes, machine format IBM-PC, MS Windows operating system, is hereby incorporated by reference.

BACKGROUND

Effective treatment of infectious diseases requires multiple inputs: the choice of the correct medication, for the correct pathogen, at the right dose to achieve cure without significant side effects. Most infectious disease diagnostics focus upon identifying the pathogen and, in some circumstances, detecting whether that pathogen is resistant to various antimicrobials. However, the dosing of the antimicrobial is critically important. If a dose is too high, patients are at risk of serious adverse events including liver toxicity, seizures, hearing loss, and, in some cases, death. By contrast, if an antimicrobial dose is too low, it may be inadequate to cure the infection, and bacteria may become resistant to the antibiotic.

In nearly all current medical practice for treatment of infectious diseases, a single dose (or weight-based dose) is used for all patients. However, metabolism of drugs varies considerably between individuals, such that some individuals will have too high of drug levels—at risk of toxicity—while others at the same dose will have too low of drug levels and be at risk for treatment failure and drug-resistance.

There have been increasing genetic markers identified that predict metabolism and/or toxicities from various medications, including antimicrobials. For example, a single mitochondrial mutation (A1555G) is associated with a 40-fold increased risk of hearing loss in individuals receiving aminoglycoside antibiotics. A single HLA type (B*5701) is associated with an 8-fold risk of potentially fatal hypersensitivity reactions to the antiviral abacavir.

Despite the availability of effective chemotherapeutic regimens for treatment and prevention of tuberculosis, a substantial proportion of patients experience toxicities, fail treatment or develop recurrent disease (1-3). Standardized, weight-based dosing of anti-tuberculosis treatment has been the conventional approach to therapy, despite mounting evidence that inter-individual variability in metabolism leads to highly variable drug levels (4,5). High drug levels are strongly associated with risk of toxicity, while low drug levels are a determinant of treatment failure, slow response, and emergence of drug resistance. Hepatotoxicity is the most common adverse effect, affecting up to 33% of patients receiving standard four-drug therapy (6) and leading to regimen changes in up to 10% of patients (7). This toxicity is associated with increased costs, morbidity, and occasional mortality, particularly among HIV co-infected individuals (8). Additionally, as many as 3% of new tuberculosis cases experience treatment failure, and between 6-10% relapse within 2 years (9,10). Pharmacokinetic variability to a single drug is associated with treatment failure and acquired drug resistance (11,12). One study found that individuals with at least one drug below the recommended AUC threshold had a 14-fold increased risk of poor outcomes (13). Moreover, antibiotic resistance is a growing problem with increasing rates of multiple drug-resistant tuberculosis (MDR-TB) and extensively drug-resistant tuberculosis (XDR-TB).

Seven specific NAT2 haplotypes (defined by single nucleotide polymorphisms) have been shown in multiple studies to strongly predict drug-induced liver injury from isoniazid, the most common medication for tuberculosis. With very few exceptions, pharmacogenetic testing has not entered the mainstream of clinical practice. High costs of testing and slow return of results is likely the major reason for the lack of use of pharmacogenetic testing to guide treatment of infectious diseases. Provided herein, inter alia, are solutions to these and other problems in the art.

BRIEF SUMMARY OF THE INVENTION

In an aspect is provided, inter alia, a method of detecting single nucleotide polymorphisms in a subject, the method including: detecting G191A NAT2 SNP, C282T NAT2 SNP, T341C NAT2 SNP, G590A NAT2 SNP and G857A NAT2 SNP in a biological sample from the subject, wherein the subject is taking an arylamine drug or a hydrazine drug or the subject is in need of an arylamine drug or a hydrazine drug. In an aspect, the subject has a tuberculosis infection and the drug is isoniazid. In an aspect, the infection is active or the infection is latent.

In another aspect is provided a kit for determining acetylator type in a subject, the kit including nucleic acid probes to G191A NAT2 SNP, C282T NAT2 SNP, T341C NAT2 SNP, G590A NAT2 SNP and G857A NAT2 SNP.

In an aspect, is provided a method for detecting single polypeptide polymorphisms in a sample from a subject having or suspected of having tuberculosis, the method including: detecting a G191A NAT2 SNP, a C282T NAT2 SNP, a T341C NAT2 SNP, a G590A NAT2 SNP and a G857A NAT2 SNP in a sample from the subject.

In another aspect is provided a method of treating a subject with a tuberculosis infection, the method including administering isoniazid to the subject at a dose greater than the isoniazid prescribed dose where a G191A NAT2 SNP, C282T NAT2 SNP, T341C NAT2 SNP, G590A NAT2 SNP and G857A SNPG857A NAT2 SNP are not detected in a biological sample from the subject.

In another aspect is provided a method of treating a subject with a tuberculosis infection, the method including administering isoniazid to the subject at a dose less than the isoniazid prescribed dose where: (a) two occurrences of G191A NAT2 SNP is detected in a biological sample from the subject, two occurrences of C282T NAT2 SNP is detected in a biological sample from the subject, two occurrences of T341C NAT2 SNP is detected in a biological sample from the subject, two occurrences of G590A NAT2 SNP is detected in a biological sample from the subject, or two occurrences of G857A SNPG857A NAT2 SNP is detected in a biological sample from the subject or, (b) at least two SNPs selected from the group consisting of G191A NAT2 SNP, C282T NAT2 SNP, T341C NAT2 SNP, G590A NAT2 SNP and G857A SNPG857A NAT2 SNP are detected in a biological sample from the subject and the at least two SNPs reside on different chromosomes.

BRIEF DESCRIPTION OF THE DRAWINGS

FIGS. 1A-1C shows NAT2 haplotype predicted from sputum qPCR strongly predicts isoniazid acetylation (FIG. 1A) and clearance (FIGS. 1B and 1C).

(FIG. 2A) Melt curve anaylsis is shown for detecting NAT2 polymorphisms for wild type (WT) and mutant (MUT) positions 191, 341, and 857, 282, and 590. Melt curve analysis is depicted for detecting wild type, mutant, and heterozygous alleles for positions (FIG. 2B) 191 and 282, (FIG. 2C) 341 and 590, and (FIG. 2D) 857.

(FIG. 3A) Melt curves corresponding to five NAT2 polymorphisms. (FIG. 3B) Amplification plots for 191, 282, 341, 590 and 857 probes. (FIG. 3C) Ct values and probe quality assessment on GeneXpert.

DETAILED DESCRIPTION

Figure 1A:
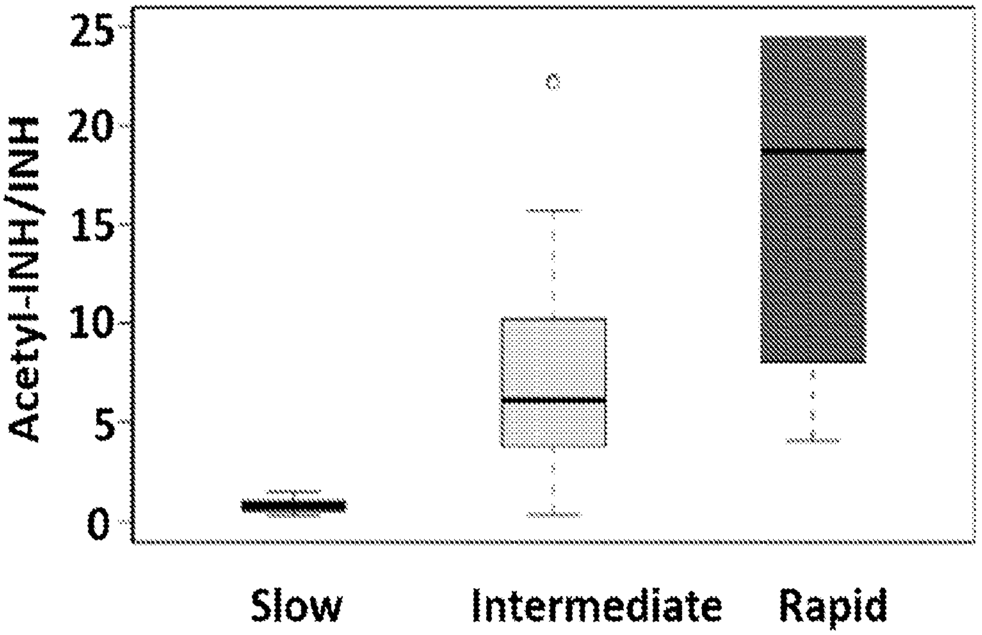
Figure 1B:
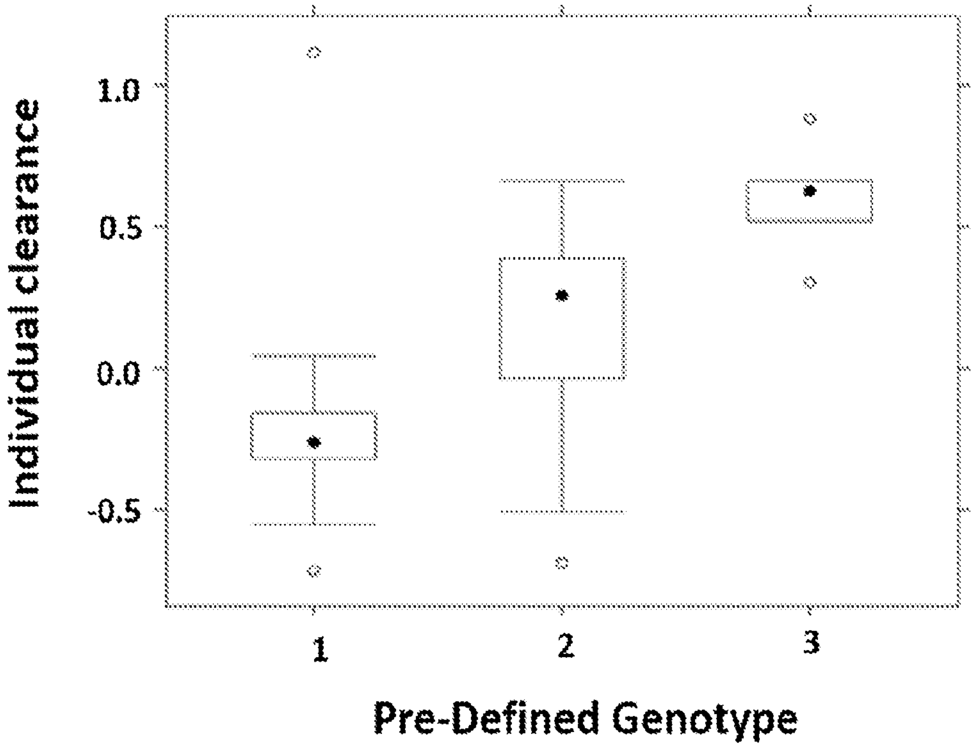
Figure 2A:
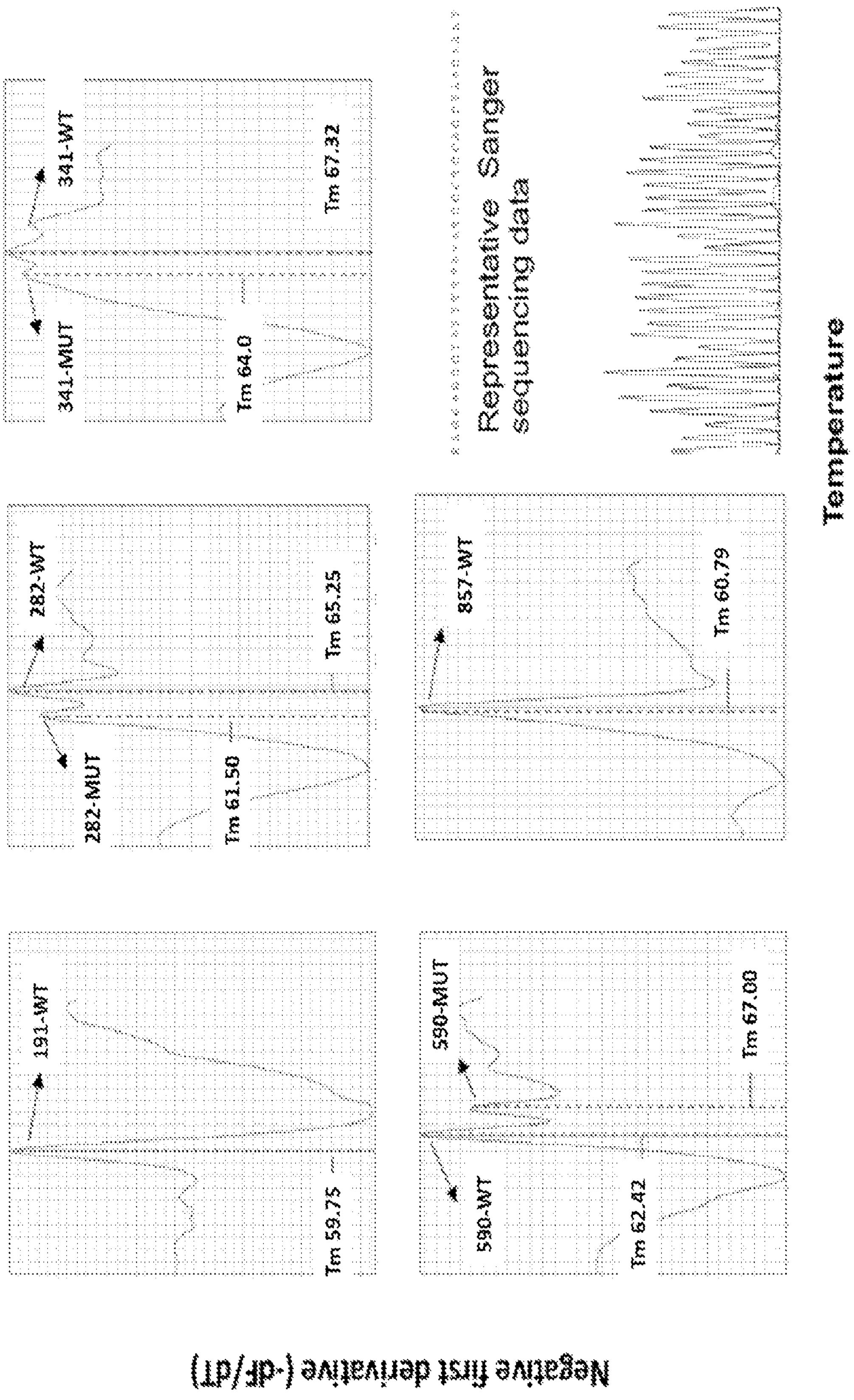
FIGS. 2A-2D illustrates representative melt curves for NAT2 polymorpisms identifed on single-plex assays.
Figure 2B:
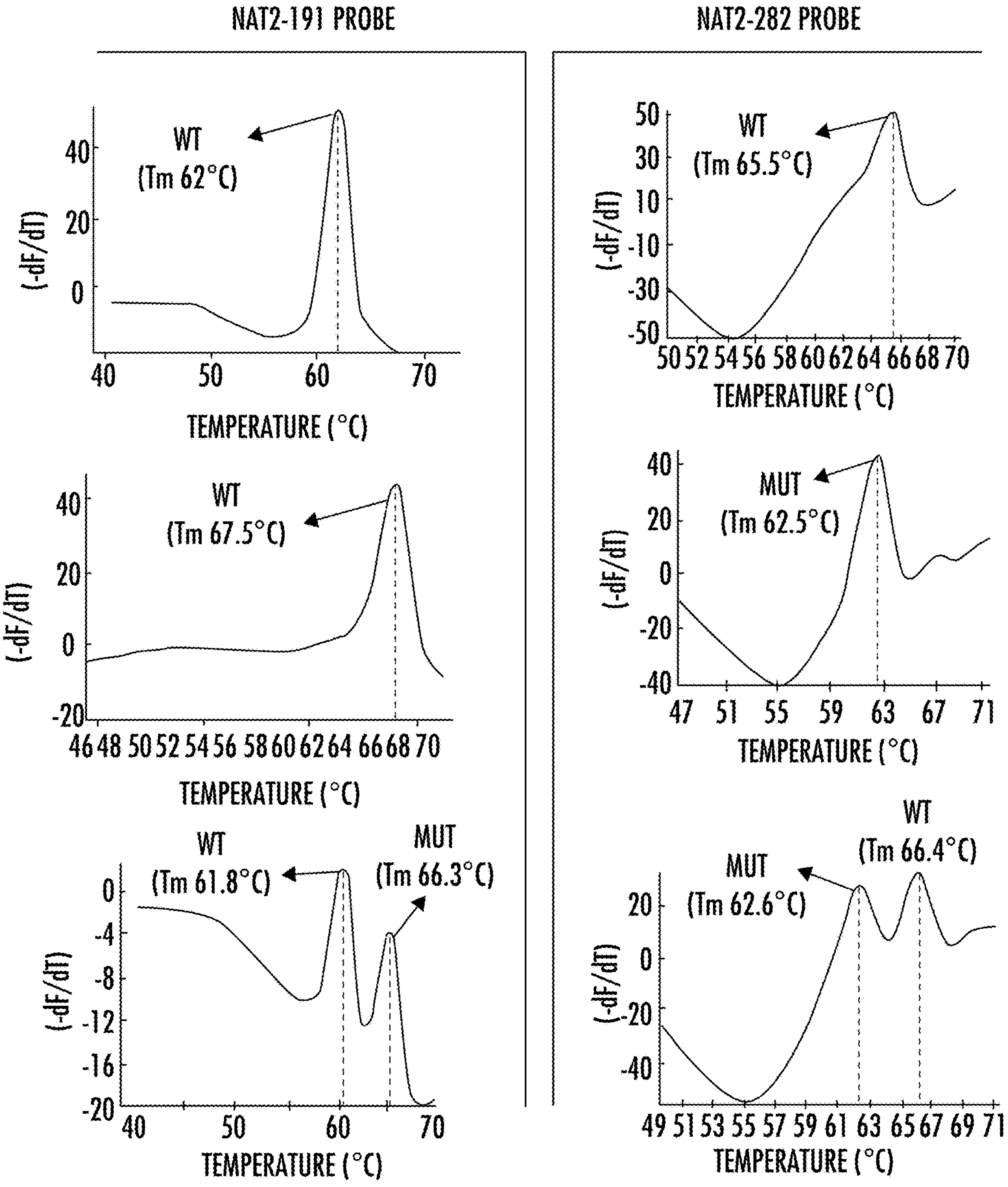
Figure 2C:
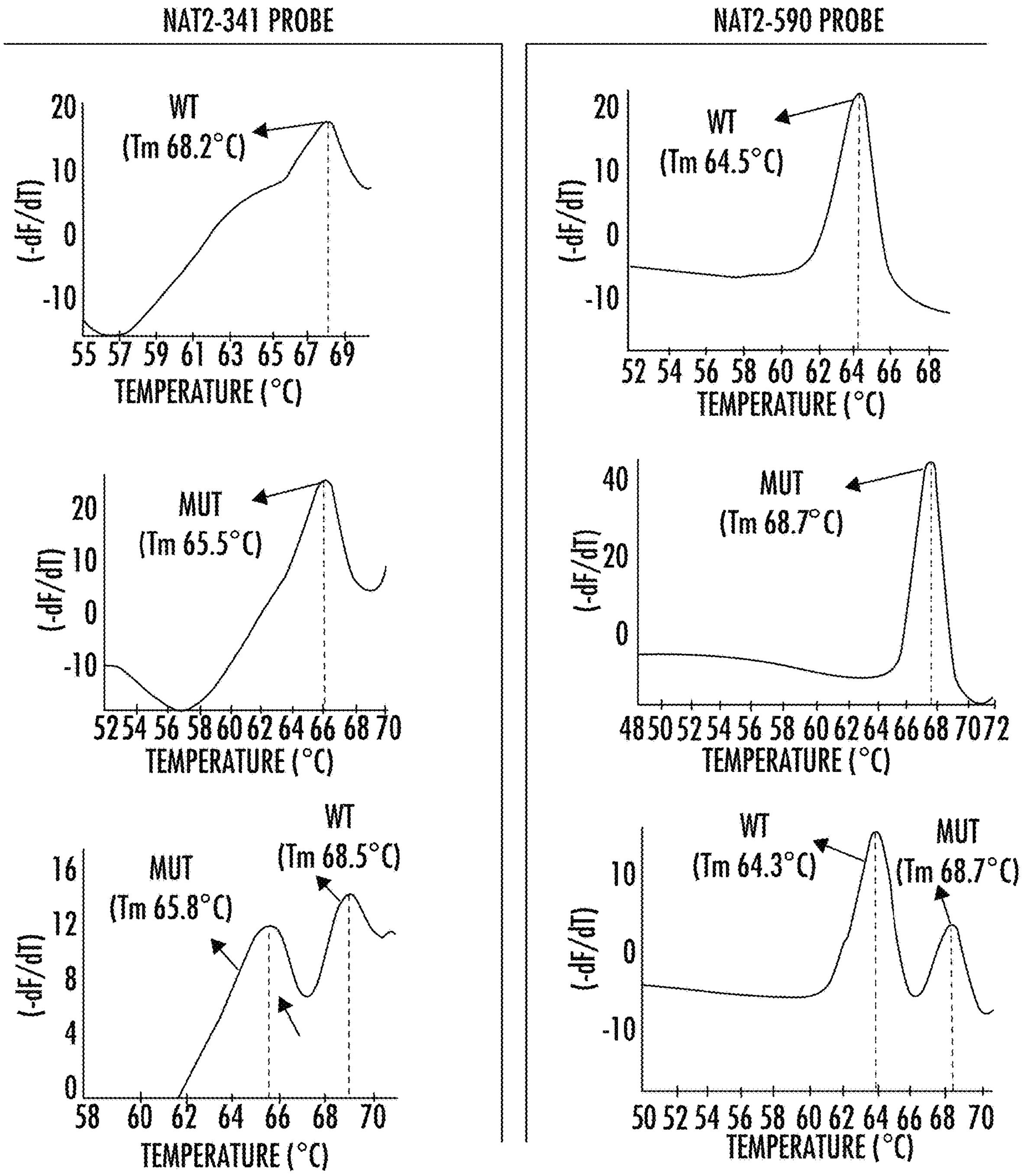
Figure 2D:
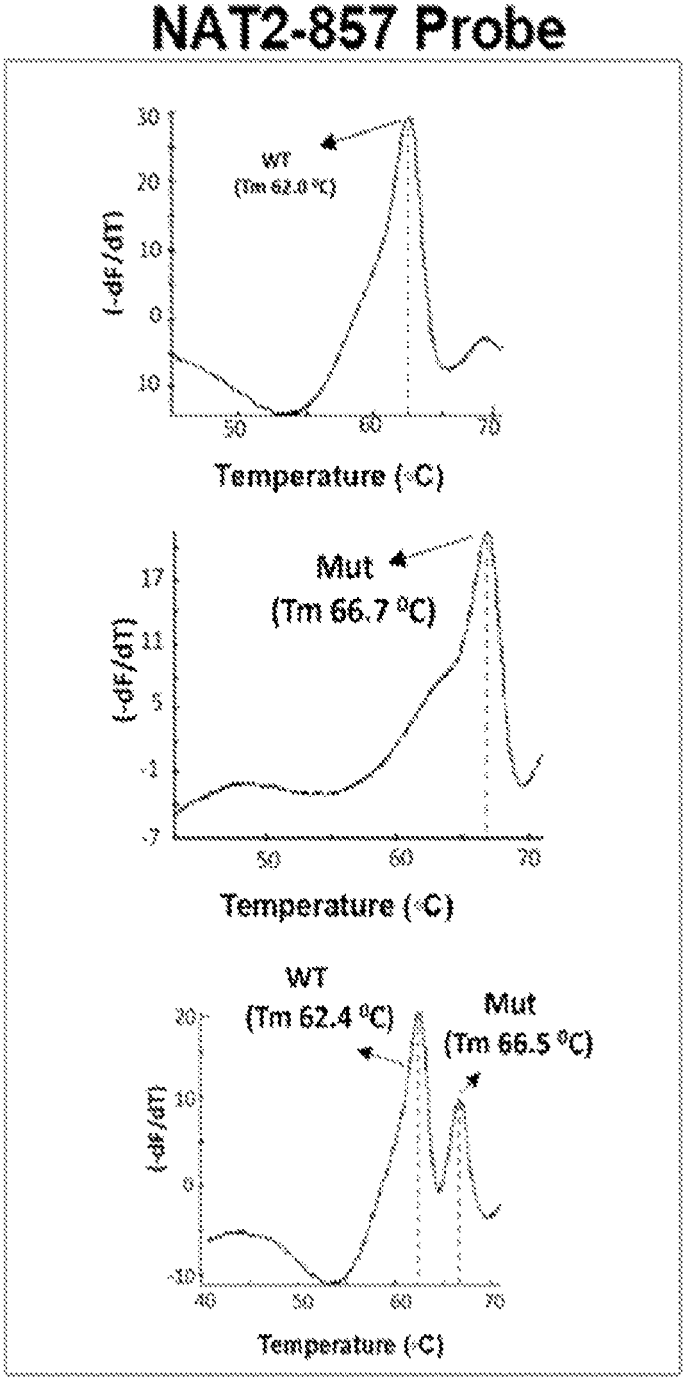
Figure 3A:
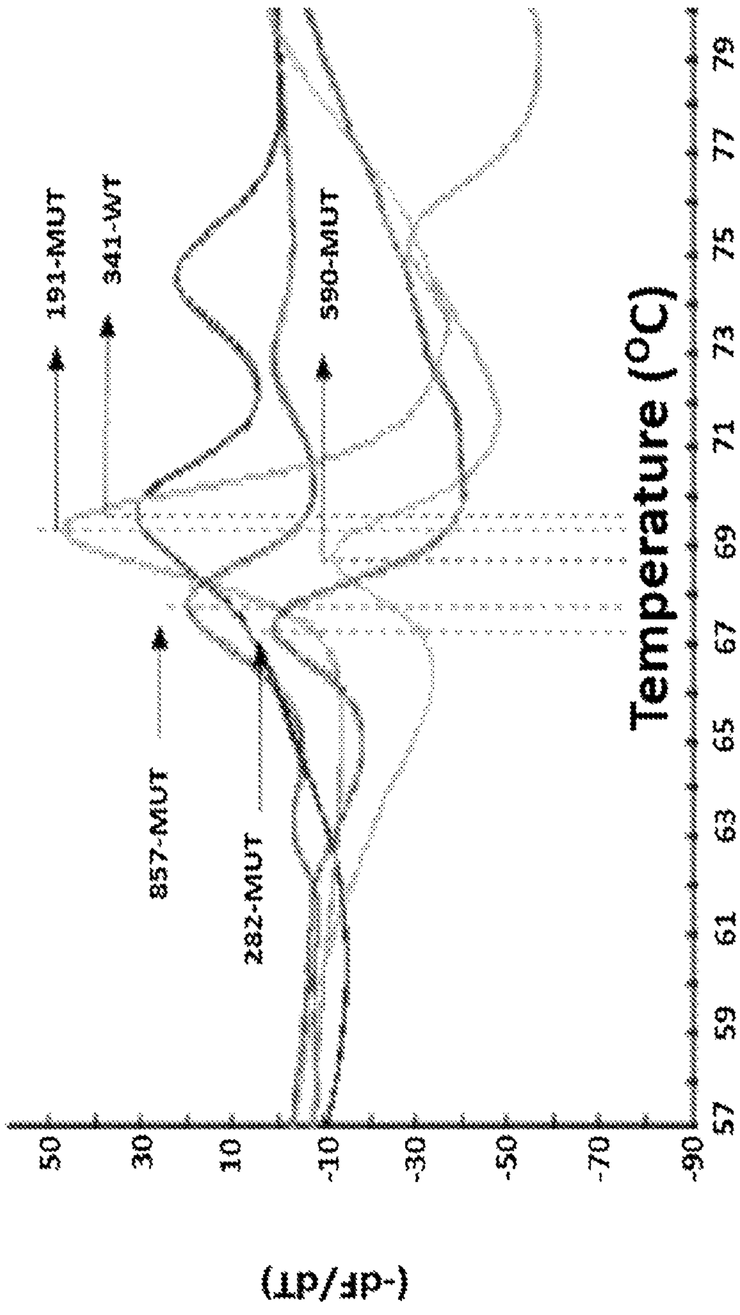
FIGS. 3A-3C show data for melt curve analysis performed on GeneXpert platform to detect NAT2 polymorphisms.
Figures 3B, 3C:
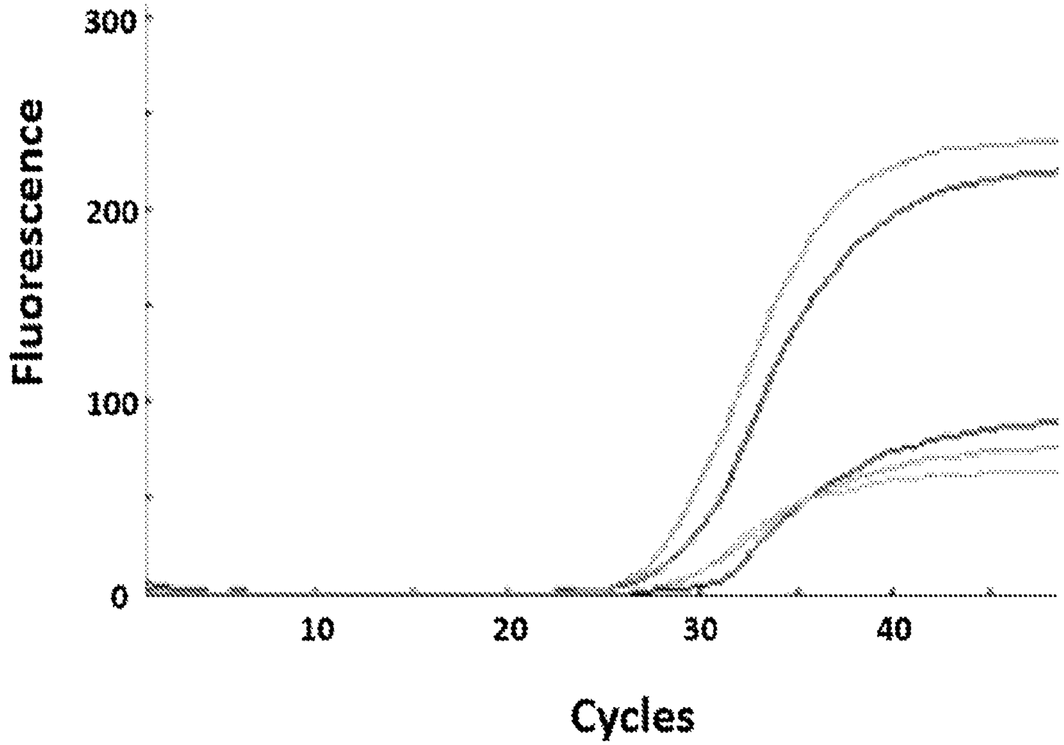

Provided herein inter alia, are methods of detecting single nucleotide polymorphisms in a subject by detecting a G191A NAT2 SNP, a C282T NAT2 SNP, a T341C NAT2 SNP, a G590A NAT2 SNP and a G857A NAT2 SNP in a biological sample, wherein the subject is taking an arylamine drug or a hydrazine drug or the subject is in need of an arylamine drug or a hydrazine drug. Applicants have developed, using machine learning from a global population dataset, methods for determining whether the subject requires an increase or lowering of a drug. In aspects, the subject can have a tuberculosis infection and the drug can be isoniazid. Also provided herein are related kits.

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "gene" refers to a DNA sequence in a chromosome that codes for a product (either RNA or its translation product, a polypeptide). A gene contains a coding region and includes regions preceding and following the coding region. The coding region is comprised of a plurality of coding segments ("exons") and intervening sequences ("introns") between individual coding segments. A gene can also comprise a non-coding RNA product such as a miRNA or lncRNA gene.

As used herein, the term "polymorphism" refers to more than one allele that occupies the gene's locus within a population. Gene polymorphisms can occur in any region of the genome. Polymorphisms can be identified in the laboratory using a variety of methods.

The term "allele" refers to varying forms of the genomic DNA located at a given site. For example, "allele" refers to a genetic variant of a specific genomic location (locus). Alleles include silent nucleotide substitutions and nucleotide substitutions that alter the amino acid sequence of the encoded protein. In some instances, alleles may result in alternative RNA splicing.

"Genotype" refers to the chemical composition of polynucleotide sequences within the genome of an individual. For example, the genotype may include single-nucleotide variants (SNVs) and/or single nucleotide polymorphisms (SNPs).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

An amino acid residue in a protein "corresponds" to a given residue when it occupies the same essential structural position within the protein as the given residue.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. In embodiments the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

For specific proteins described herein, the named protein includes any of the protein's naturally occurring forms, variants or homologs that maintain the protein activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof The term "NAT2 protein" or "NAT2" as used herein includes any of the recombinant or naturally-occurring forms of N-acetyltransferase-2, also known as Arylamide acetylase 2, N-acetyltransferase type 2, Polymorphic arylamine N-acetyltransferase, or variants or homologs thereof that maintain NAT2 activity (e.g. within at least 50%, 80%, 90%, 95%, 96%, 97%, 98%, 99% or 100% activity compared to NAT2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NAT2 protein. In embodiments, the NAT2 protein is substantially identical to the protein identified by the UniProt reference number P11245 or a variant or homolog having substantial identity thereto.

The term "IS6110 protein" or "IS6110" as used herein includes any of the recombinant or naturally-occurring forms of Transposase, from Mycobacterium tuberculosis, or variants or homologs thereof that maintain IS6110 activity (e.g. within at least 50%, 80%, 90%, 95%, 96%, 97%, 98%, 99% or 100% activity compared to IS6110). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IS6110 protein. In embodiments, the IS6110 protein is substantially identical to the protein identified by the UniProt reference number Q4GZQ9 or a variant or homolog having substantial identity thereto.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof As used herein the term, "NAT2" or "NAT2 gene" refers to the gene encoding N-acetyltransferase 2 (arylamine N-acetyltransferase), also known as NAT2, an enzyme which in humans is encoded by the NAT2 gene. This gene encodes a type of N-acetyltransferase. The NAT2 isozyme functions to both activate and deactivate arylamine and hydrazine drugs and carcinogens. Polymorphisms in this gene are responsible for the N-acetylation polymorphism in which human populations segregate into rapid, intermediate, and slow acetylator phenotypes. Polymorphisms in NAT2 are also associated with higher incidences of cancer and drug toxicity. In embodiments, the NAT2 gene is substantially identical to the nucleic acid sequence corresponding to position 18386585 to 18401219 of the nucleic acid sequence identified by Accession No. NC_000008.11 or a variant or homolog having substantial identity thereto.

As used herein the term, "IS6110" or "IS6110 gene" refers to the gene encoding insertion element IS6110, also known as transposon. This gene is found in *Mycobacterium tuberculosis*. In embodiments, the IS6110 gene is substantially identical to the nucleic acid sequence corresponding to the nucleic acid sequence identified by Accession No. X17348.1 or a variant or homolog having substantial identity thereto.

Drugs that can be acetylated by NAT2 include, but are not limited to, isoniazid (INH), hydralazine, sulphadoxine, procainamide, and dapsone. As used herein the term "isoniazid", or "isonicotinylhydrazide (INH)" refers to an antibiotic used for the treatment of tuberculosis. As used herein "hydralazine" refers to a vasodilator used for the treatment of high blood pressure. As used herein "sulphadoxine" refers to an ultra-long-lasting sulfonamide, that is used in combination with pyrimethamine to treat malaria. As used herein "procainamide" refers to a sodium channel blocker of cardiomyocytes used for the treatment of cardiac arrhythmias. As used herein "dapsone" also known as diaminodiphenyl sulfone (DDS), refers to an antibiotic used in combination with rifampicin and clofazimine for the treatment of leprosy. Dapsone is a second-line medication for the treatment and prevention of pneumocystis pneumonia and for the prevention of toxoplasmosis in those who have poor immune function. Additionally, it has been used for acne, dermatitis herpetiformis, and various other skin conditions.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{123}$I, $^{124}$I, $^{125}$I, $^{131}$I, $^{142}$Pr, $^{143}$Pr, $^{149}$Pm, $^{153}$Sm, $^{154-1581}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$a and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

The terms "disease" or "condition" refer to a state of being or health status of a patient or subject capable of being treated with the compounds or methods provided herein. The disease may be an inflammatory disease. The disease may be an infectious disease. The disease may be a bacterial infection. The disease may be a viral infection.

The term "infection" or "infectious disease" refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by *Mycobacterium tuberculosis*). Non-limiting bacteria associated diseases include pneumonia, which may be caused by bacteria such as *Streptococcus* and *Pseudomonas*; or foodborne illnesses, which can be caused by bacteria such as *Shigella, Campylobacter*, and *Salmonella*. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the *Lactobacilli* species that maintain healthy vaginal microbial populations) (e.g., yeast infection, or *Trichomonas vaginalis*); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is a *Campylobacter jejuni, Enterococcus faecalis, Haemophilus influenzae, Helicobacter pylori, Klebsiella pneumoniae, Legionella pneumophila, Neisseria gonorrhoeae, Neisseria meningitides, Staphylococcus aureus, Streptococcus pneumonia*, or *Vibrio cholera* infection. In embodiments, the infectious disease is a *Mycobacterium tuberculosis* infection. In embodiments, the infectious diseases is a viral disease. In embodiments, the infectious diseases is human immunodeficiency virus (HIV) infection. In embodiments, the infectious diseases is an invasive bacterial infection. In embodiments, the infectious diseases is a viral respiratory infection.

As used herein "Tuberculosis" or "TB" refers to its usual and customary meaning as an infectious disease usually caused by *Mycobacterium tuberculosis* (MTB) bacteria. Most infections show no symptoms, in which case it is known as "latent tuberculosis." About 10% of latent infections progress to active disease which, if left untreated, kills about half of those affected. The classic symptoms of "active TB" are a chronic cough with blood-containing mucus, fever, night sweats, and weight loss. It was historically called consumption due to the weight loss. Tuberculosis is spread from one person to the next through the air when people who have active TB in their lungs cough, spit, speak, or sneeze. People with latent TB do not spread the disease. Active infection occurs more often in people with HIV/AIDS and in those who smoke. Diagnosis of active TB is based on chest X-rays, as well as microscopic examination and culture of body fluids. Diagnosis of latent TB relies on the tuberculin skin test (TST) or blood tests.

"Treating" or "treatment" as used herein (and as well-understood in the art) also includes any approach for obtaining beneficial or desired results in a subject's condition, including clinical results. Beneficial or desired clinical results can include, but are not limited to, alleviation or amelioration of one or more symptoms or conditions, diminishment of the extent of a disease (e.g. tuberculosis), stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein includes prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment. In regards to tuberculosis, the subject can be treated for an active infection or the subject can be treated for a latent infection.

The term "prevent" refers to a decrease in the occurrence of disease symptoms in a patient. As indicated above, the prevention may be complete (no detectable symptoms) or partial, such that fewer symptoms are observed than would likely occur absent treatment.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components.

"Contacting" is used in accordance with its plain ordinary meaning and refers to the process of allowing at least two distinct species (e.g. enzyme and substrate) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "therapeutic agent" as referred to herein, is a composition useful in treating or preventing a disease, such as one caused by a bacterial infection (e.g., tuberculosis). In embodiments, the therapeutic agent is an arylamine drug. In embodiments, the therapeutic agent is hydrazine drug.

As used herein, "hydrazine drugs" refer to therapeutic compounds derived from hydrazine. Examples of hydrazine drugs include: Carbidopa, Phenelzine, Levosimendan, Isoniazid, Balsalazide, Iproniazid, Sivifene, Aldoxorubicin, Semapimod, Simendan. For example, Cardidopa is a dopa decarboxylase inhibitor used in combination with levodopa for the symptomatic treatment of idiopathic Parkinson disease and other conditions associated with parkinsonian symptoms. Phenelzine is a monoamine oxidase inhibitor used to treat atypical, nonendogenous, or neurotic depression. Levosimendan is used for short term treatment of acutely decompensated severe chronic heart failure (CHF). Levosimendan is further being investigated for use/treatment in heart disease. Isoniazid is an antibiotic used to treat mycobacterial infections. Isoniazid is commonly used in combination with other antimycobacterial agents for the treatment of active or latent tuberculosis. Balsalazide is an aminosalicylate used to treat ulcerative colitis. Iproniazid was originally intended to treat tuberculosis, and currently used for the treatment of depression. Sivifene, is a compound used for treatment of cervical dysplasia/cancer, genital warts, and skin cancer. Aldoxorubicin is a compound investigated for use/treatment in solid tumors. Semapimod is a compound currently used in trials studying the treatment of Crohn Disease. Simendan is under investigation in clinical trial NCT00527059 (Renal Effects of Levosimendan in Patients Admitted With Acute Decompensated Heart Failure). Thus, in embodiments, the hydrazine drug is Carbidopa, Phenelzine, Levosimendan, Isoniazid, Balsalazide, Iproniazid, Sivifene, Aldoxorubicin, Semapimod, Simendan. In embodiments, the hydrazine drug is Carbidopa. In embodiments, the hydrazine drug is Phenelzine. In embodiments, the hydrazine drug is Levosimendan. In embodiments, the hydrazine drug is Isoniazid. In embodiments, the hydrazine drug is Balsalazide. In embodiments, the hydrazine drug is Iproniazid. In embodiments, the hydrazine drug is Sivifene. In embodiments, the hydrazine drug is Aldoxorubicin, Semapimod, Simendan. In embodiments, the hydrazine drug is Aldoxorubicin. In embodiments, the hydrazine drug is Semapimod. In embodiments, the hydrazine drug is Simendan.

Arylamine drugs are therapeutic compounds derived from or including an arylamine moiety. Examples of arylamine drugs include Dapsone, Benzocaine, acebutolol, procainamide, Sulfamethoxazole, or Nitrazepam. Dapsone is an antibiotic, commonly used in combination with other therapeutics for the treatment of leprosy. Benzocaine is a local anesthetic, and can be found in topical pain relievers and in cough drops. Acebutolol is a beta-blocker commonly used to treat high blood pressure, angina, and irregular heartbeat. Procainamide is a sodium channel blocker commonly used to treat cardiac arrhythmias. Sulfamethoxazole is used as an antibacterial. Nitrazepam is a benzodiazepine commonly used as a sedative. Nitrazepam may be used as an anticonvulsant and as treatment for severe anxiety and insomnia. Thus, in embodiments, the arylamine drug is Dapsone, Benzocaine, acebutolol, procainamide, or Sulfamethoxazole. In embodiments, the arylamine drug is Dapsone. In embodiments, the arylamine drug is Benzocaine. In embodiments, the arylamine drug is acebutolol. In embodiments, the arylamine drug is procainamide, or Sulfamethoxazole. In embodiments, the arylamine drug is Sulfamethoxazole. In embodiments, the arylamine drug is Nitrazepam.

The terms "disorder" or "disease" as provided herein are used interchangeably and refer to any deviation from the normal health of a mammal and include a state when disease/disorder symptoms are present, as well as conditions in which a deviation (e.g., chemical imbalance, infection, gene mutation, genetic defect, etc.) has occurred, but symptoms are not yet manifested or are not yet fully manifested.

According to the present invention, the methods disclosed herein are suitable for use in a subject that is a member of the Vertebrate class, Mammalia, including, without limitation, primates, livestock and domestic pets (e.g., a companion animal). Typically, a subject will be a human subject.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In embodiments, the control is the activity of one variant of an enzyme (e.g. NAT2) compared to another variant of the same enzyme. In embodiments, the control is the activity of a drug in the presence of one variant of an enzyme (e.g. NAT2) compared to the activity of the drug in the presence of another variant of the same enzyme. In embodiments, the control is the acetylation level of a drug in the presence of one variant of an enzyme (e.g. NAT2) compared to the acetylation level of the drug in the presence of another variant of the same enzyme. In some instances, the control is used as a standard of comparison in evaluating experimental effects. In embodiments, the control is the activity of one variant of a gene (e.g. NAT2) compared to another variant of the same gene. In embodiments, the control is the activity of a drug in the presence of one variant of a gene (e.g. NAT2) compared to the activity of the drug in the presence of another variant of the same gene. In embodiments, the control is the acetylation level of a drug in the presence of one variant of a gene (e.g. NAT2) compared to the acetylation level of the drug in the presence of another variant of the same gene.

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

II. Methods of Detecting

Provided herein, inter alia, is a method for predicting drug acetylation levels in subjects based on detection of NAT2 polymorphisms. In embodiments, the drug is an arylamine drug or a hydrazine drug. As described herein, five (5) NAT2 SNPs-G191A, C282T, T341C, G590A and G857A were identified which could predict phased genotype with >99.9% accuracy. The unphased genotype prediction is contemplated to be useful for predicting phenotype. As described herein, these five polymorphisms were used to develop NAT2/PGx assay, which was successfully demonstrated on an automated DNA extraction and real-time PCR platform (GeneXpert). Multicolor melt curve analysis (MMCA) was used to calculate melt Tm difference between mutant, heterozygous and wild types. The data generated were used to predict acetylator phenotype by NAT2 phenotype predictor algorithm. The polymorphism data were validated by Sanger sequencing. NAT2/PGx assay could detect all five NAT2 polymorphisms including heterozygous alleles with 100% accuracy directly from whole blood in about 140 minutes.

As used herein, the terms "single-nucleotide polymorphism" and "SNP" refer to a substitution of a single nucleotide that occurs at a specific position in the genome. The genetic variations may be unique or occur relatively frequently within a population. For example, a SNP may be present at a level of more than 1% in the population. For example, at a specific base position in the human genome, the C nucleotide may appear in most individuals, but in a minority of individuals, the position is occupied by an A. Thus, there is a SNP at this specific position, and the two possible nucleotide variations—C or A—are said to be the alleles for this specific position.

In embodiments, the SNPs described herein are identified by the "SNP ID number" as provided in the NCBI dbSNP database. In embodiments, G191A NAT2 SNP is identified by the SNP ID number rs1801279. In embodiments, C282T NAT2 SNP is identified by the SNP ID number rs1041983. In embodiments, T341C NAT2 SNP is identified by the SNP ID number rs1801280. In embodiments, G590A NAT2 SNP is identified by the SNP ID number rs1799930. In embodiments, G857A NAT2 SNP is identified by the SNP ID number rs1799931.

The presence or absence of NAT2 SNPs in a subject is contemplated to be useful for predicting whether the subject displays rapid, intermediate or slow acetylation for classes of therapeutics (e.g. arylamine drugs, hydrazine drugs). For example, the presence of certain SNPs are predictive of slow acetylation, indicative of slow drug metabolism. In another instance, the absence of certain SNPs are predictive of fast acetylation, indicative of fast drug metabolism. Thus, the method provided herein including embodiments thereof is contemplated to be useful for administering arylamine drugs or hydrazine drugs to a subject in need thereof.

For the method provided herein, in embodiments, a clinical specimen from a subject (e.g. sputum, blood, oral swabs, saliva etc.) can be collected and stored in DNA preservative until processed. In embodiments, processing inludes mixing samples with appropriate lysis buffer and loading the samples into cartridges for automated DNA extraction followed by real time PCR-based amplification and probe-based detection.

Thus, in an aspect is provided a method of detecting single nucleotide polymorphisms in a subject, the method including: detecting G191A NAT2 SNP, C282T NAT2 SNP, T341C NAT2 SNP, G590A NAT2 SNP and G857A NAT2 SNP in a biological sample from the subject, wherein the subject is taking an arylamine drug or a hydrazine drug or the subject is in need of an arylamine drug or a hydrazine drug. In embodiments, the subject is taking an arylamine drug or a hydrazine drug. In embodiments, the subject is taking an arylamine drug. In embodiments, the subject is taking a hydrazine drug. In embodiments, the subject is in need of an arylamine drug or a hydrazine drug. In embodiments, the subject is in need of an arylamine drug. In embodiments, the subject is in need of a hydrazine drug.

In embodiments, the method does not include detecting an additional NAT2 SNP in the biological sample. In embodiments, the method does not include detecting an additional SNP in the biological sample. In embodiments, the detecting the G191A NAT2 SNP includes determining whether the G191A NAT2 SNP is not present, present once or present more than once within the chromosomes of the subject. In embodiments, the detecting the G191A NAT2 SNP includes determining whether the G191A NAT2 SNP is not present within the chromosomes of the subject. In embodiments, the detecting the G191A NAT2 SNP includes determining whether the G191A NAT2 SNP is present once within the chromosomes of the subject. In embodiments, the detecting the G191A NAT2 SNP includes determining whether the G191A NAT2 SNP is present more than once within the chromosomes of the subject.

In embodiments, the detecting the C282T NAT2 SNP includes determining whether the C282T NAT2 SNP is not present, present once or present more than once within the chromosomes of the subject. In embodiments, the detecting the C282T NAT2 SNP includes determining whether the C282T NAT2 SNP is not present within the chromosomes of the subject. In embodiments, the detecting the C282T NAT2 SNP includes determining whether the C282T NAT2 SNP is present once within the chromosomes of the subject. In embodiments, the detecting the C282T NAT2 SNP includes determining whether the C282T NAT2 SNP is present more than once within the chromosomes of the subject.

In embodiments, the detecting the T341C NAT2 SNP includes determining whether the T341C NAT2 SNP is not present, present once or present more than once within the chromosomes of the subject. In embodiments, the detecting the T341C NAT2 SNP includes determining whether the T341C NAT2 SNP is not present within the chromosomes of the subject. In embodiments, the detecting the T341C NAT2 SNP includes determining whether the T341C NAT2 SNP is present once within the chromosomes of the subject. In embodiments, the detecting the T341C NAT2 SNP includes determining whether the T341C NAT2 SNP is present more than once within the chromosomes of the subject.

In embodiments, the detecting the G590A NAT2 SNP includes determining whether the G590A NAT2 SNP is not present, present once or present more than once within the chromosomes of the subject. In embodiments, the detecting the G590A NAT2 SNP includes determining whether the G590A NAT2 SNP is not present within the chromosomes of the subject. In embodiments, the detecting the G590A NAT2 SNP includes determining whether the G590A NAT2 SNP is present once within the chromosomes of the subject. In embodiments, the detecting the G590A NAT2 SNP includes determining whether the G590A NAT2 SNP is present more than once within the chromosomes of the subject.

In embodiments, the detecting the G857A NAT2 SNP includes determining whether the G857A NAT2 SNP is not present, present once or present more than once within the chromosomes of the subject. In embodiments, the detecting the G857A NAT2 SNP includes determining whether the G857A NAT2 SNP is not present within the chromosomes of the subject. In embodiments, the detecting the G857A NAT2 SNP includes determining whether the G857A NAT2 SNP is present once within the chromosomes of the subject. In embodiments, the detecting the G857A NAT2 SNP includes determining whether the G857A NAT2 SNP is present more than once within the chromosomes of the subject.

In embodiments, the method does not include detecting any additional NAT2 SNP. In embodiments, the method does not include detecting any additional SNP. For example, detection of at least one of the five NAT2 SNPs described herein (e.g. G191A NAT2 SNP, C282T NAT2 SNP, T341C NAT2 SNP, G590A NAT2 SNP and G857A NAT2 SNP) is sufficient for predicting acetylation of a drug compound provided herein. For example, the absence of one or more of the five NAT2 SNPs described herein (e.g. G191A NAT2 SNP, C282T NAT2 SNP, T341C NAT2 SNP, G590A NAT2 SNP and G857A NAT2 SNP) is sufficient for predicting acetylation of a drug compound provided herein.

In embodiments, the detecting includes melt curve analysis, 5' exonuclease polymerase chain reaction, DNA sequencing, restriction fragment length polymorphism, chip hybridization or single base extension assay. In embodiments, the detecting includes melt curve analysis. In embodiments, the detecting includes 5' exonuclease polymerase chain reaction. In embodiments, the detecting includes DNA sequencing. In embodiments, the detecting includes restriction fragment length polymorphism. In embodiments, the detecting includes chip hybridization. In embodiments, the detecting includes single base extension assay.

Polymorphisms, including single nucleotide polymorphisms, can be detected in a biological sample, by any method known in the art. Methods of detecting SNPs include melt curve analysis (as provided in the examples herein), DNA sequencing, methods that require allele specific hybridization of primers or probes (e.g., dynamic allele-specific hybridization (DASH), use of molecular beacons, and SNP microarrays such as the Affymetrix Human SNP Array 6.0), allele specific incorporation of nucleotides to primers bound close to or adjacent to the polymorphisms ("single base extension", or "minisequencing"), allele-specific ligation of oligonucleotides (ligation chain reaction or ligation padlock probes), allele-specific cleavage of oligonucleotides or PCR products by restriction enzymes (restriction fragment length polymorphisms analysis or RFLP) or chemical or other agents, resolution of allele-dependent differences in electrophoretic or chromatographic mobilities, by structure specific enzymes including invasive structure specific enzymes, or mass spectrometry. DNA sequencing methods can include, but are not limited to, single-molecule real time sequencing (Pacific Biosciences), ion semiconductor (Ion Torrent Sequencing; Life Technologies), pyrosequencing (454 Life Sciences), sequencing by synthesis (Illumina Inc.), and sequencing by ligation (SOLiD Sequencing; Applied Biosystems). The term "DNA sequencing" is used according to its commonly known meaning in the art and refers to the process of determining the nucleic acid sequence in DNA. For example, the order of the four bases (A, G, C, and T) can be determined through DNA sequencing methods. Methods for DNA sequencing are well known in the art and described for example, by Heather J M, Chain B. The sequence of sequencers: The history of sequencing DNA. Genomics. 2016 January; 107(1):1-8. and Shendure J, Mitra R D, Varma C, Church G M. Advanced sequencing technologies: methods and goals. Nat Rev Genet. 2004 May; 5(5):335-44.; which are incorporated by reference herein in their entirery and for all purposes.

As used herein, "melt curve analysis" refers to an assessment of the dissociation characteristics of double-stranded DNA during heating. A nucleic acid probe that has a mismatch at the SNP will have a different melting characteristic than a nucleic acid probe that is complementary at the SNP.

As used herein, "5' exonuclease polymerase chain reaction" refers to a polymerase chain reaction that produces a detectable signal concomitantly with nucleic acid amplification. In instances, forward and reverse PCR primers that will amplify a region of DNA that includes the SNP polymorphic site are needed. Allele discrimination can be achieved using FRET combined with one or two allele-specific probes that hybridize to the SNP polymorphic site. The probes will have a detectable moiety (e.g. a fluorophore) linked to their 5' end and a quencher molecule linked to their 3' end. The quencher can remain in close proximity to the fluorophore, eliminating the fluorophore's signal. During the PCR amplification step, if the allele-specific probe is perfectly complementary to the SNP allele, it will bind to the target DNA strand and then get degraded by 5'-nuclease activity of the polymerase (e.g. Taq polymerase) as it extends the DNA from the PCR primers. Thus, the fluorophore is separated from the quencher as the probe is degraded, thereby generating a detectable signal. If the allele-specific probe is not perfectly complementary, it will not bind as efficiently, therefore preventing the nuclease from acting on the probe.

As used herein, "restriction fragment length polymorphism" or "RFLP" refers to a method that detects polymorphisms in homologous DNA sequences. The polymorphisms may be used to determine the locations of genes within a DNA sequence. In instances, a DNA sample is digested into fragments by one or more endonucleases (e.g. restriction enzymes), and the resulting DNA fragments are then separated (e.g. by gel electrophoresis) according to their size.

The term "chip hybridization" or "DNA microarray" are used interchangeably and refer to a method in which single nucleotide polymorphisms among alleles within or between a populations are detected. Typically, chip hybridization detects hybridization between two DNA strands, for example the immobilized allele-specific oligonucleotide (ASO) probe and the test DNA samples. For example, following removal (e.g. washing off) non-specific binding DNA sequences, DNA sequences with higher percentage of complementarity remain hybridized. In instances, fluorescently labeled target sequences that bind to a probe sequence generate a signal that depends on the hybridization conditions (e.g. temperature), and washing after hybridization. Total strength of the signal, depends upon the amount of target sample binding to the probes present on that spot. For example, a strong signal can indicates presence of the SNP. For example, microarrays use relative quantitation in which the intensity of a feature is compared to the intensity of the same feature under a different condition.

The term "single base extension assay" or "SBE" refers to a method for determining the identity of a nucleotide base at a specific position within a DNA sequence. SBE is commonly used to identify SNPs. In instances, an oligonucleotide primer hybridizes to a complementary fragment along the nucleic acid to form a duplex, with the primer's terminal 3'-end adjacent to the nucleotide base to be identified. The oligonucleotide primer can be enzymatically extended (e.g. by a DNA polymerase) by a single base in the presence of all four nucleotide terminators. Thus, the nucleotide terminator complementary to the base in the template being identified is incorporated. In this manner, misincorporation of non-complementary nucleotides is suppressed in the presence of all four terminators.

In embodiments, a nucleic acid probe is used in the method described herein including embodiments thereof. The terms "nucleic acid probe" or "probe" as used herein refer to a nucleic acid sequence (e.g. DNA, RNA) that is used to detect a target nucleic acid sequence (e.g. DNA, RNA) that is complementary to the sequence of the probe. In embodiments, the nucleic acid probe has a secondary structure (e.g. stem loop). In embodiments, the nucleic acid probe is single-stranded. The probe can be from 10 nucleic acid residues to about 10,0000 nucleic residues long. Preferably, the probe is 15 nucleic acid residues, 16 nucleic acid residues, 17 nucleic acid residues, 18 nucleic acid residues, 19 nucleic acid residues, 20 nucleic acid residues, 21 nucleic acid residues, 22 nucleic acid residues, 23 nucleic acid residues, 24 nucleic acid residues, 25 nucleic acid residues, 26 nucleic acid residues, 27 nucleic acid residues, 28 nucleic acid residues, 29 nucleic acid residues, or 30 nucleic acid residues long. In embodiments, the probe includes a detectable moiety allowing allowing detection of hybridization of the probe to the target nucleic acid, wherein hybridization occurs by complementary base pairing. For example, the probe may be used to detect the presence of a SNP. In embodiments, the nucleic acid probe is a molecular beacon probe. For example, the molecular beacon probe may include a quencher on one end of the probe and and a fluorophore on the other end. If the molecular beacon probe hybridizes to the target nucleic acid sequence (e.g. a sequence including a SNP), the quencher and fluorophore may be further apart in distance, thereby producing a fluorescent signal. In instances, the molecular beacon probe may form a stem-loop structure. In this instance, if the probe is not hybridized to a target nucleic acid sequence, no fluorescent signal is observed due to the close proximity of the fluorophore and quencher.

Thus, for the method provided herein, in embodiments, the nucleic acid probe to G191A NAT2 SNP includes the sequence of SEQ ID NO:7. In embodiments, the nucleic acid probe to G191A NAT2 SNP is the sequence of SEQ ID NO:7. In embodiments, the nucleic acid probe to C282T NAT2 SNP includes the sequence of SEQ ID NO: 8. In embodiments, the nucleic acid probe to C282T NAT2 SNP is the sequence of SEQ ID NO:8. In embodiments, the nucleic acid probe to T341C NAT2 SNP includes the sequence of SEQ ID NO:9. In embodiments, the nucleic acid probe to T341C NAT2 SNP is the sequence of SEQ ID NO:9. In embodiments, the nucleic acid probe to G590A NAT2 SNP includes the sequence of SEQ ID NO:10. In embodiments, the nucleic acid probe to G590A NAT2 SNP is the sequence of SEQ ID NO:10. In embodiments, the nucleic acid probe to G857A NAT2 SNP includes the sequence of SEQ ID NO:11. In embodiments, the nucleic acid probe to G857A NAT2 SNP is the sequence of SEQ ID NO:11.

For the method provided herein, in embodiments, an unphased SNP is detected. In reference to the SNP(s) detected by the methods provided herein, the term "unphased" refers to detecting the presence of the SNP without regard to which one of the pair of chromosomes from the subject includes the allele comprising the SNP. For example, the SNP may be detected and quantified (e.g. two occurences of the SNP) without determination of which chromosome the SNP is on.

For the method provided herein, in embodiments, the biological sample is a sputum sample, a saliva sample, a blood sample or a buccal sample. In embodiments, the biological sample is a sputum sample. In embodiments, the biological sample is a saliva sample. In embodiments, the biological sample is a blood sample. In embodiments, the biological sample is a buccal sample. Methods for obtaining such biological samples are well known in the art.

In embodiments, the subject has a tuberculosis infection. In embodiments, the tuberculosis infection is latent. In embodiments, the tuberculosis infection is active. In embodiments, the drug is isoniazid, hydralazine, sulphadoxine, procainamide, or dapsone. In embodiments the drug is isoniazid. In embodiments the drug is hydralazine. In embodiments the drug is sulphadoxine. In embodiments the drug is procainamide. In embodiments the drug is dapsone.

In embodiments, the subject with a TB infection is a daily user of alcohol, has active chronic liver disease or severe renal dysfunction, is an age greater than 35, concurrently uses one or more chronically administered medication, has previously discontinued administration of isoniazid, is pregnant, has injection drug use, has peripheral neuropathy or conditions predisposing to neuropathy is a woman belonging to a minority group, or is HIV seropositive. In embodiments, the subject with a TB infection is a daily users of alcohol. Daily ingestion of alcohol may be associated with a higher incidence of + isoniazid hepatitis. In embodiments, the subject with a TB infection has active chronic liver disease or severe renal dysfunction. In embodiments, the subject with a TB infection is greater than 35 years old. In embodiments, the subject with a TB infection concurrently uses at least one chronically administered medication. In embodiments, the subject with a TB infection is previously discontinued administration of isoniazid. In embodiments, the subject with a TB infection has peripheral neuropathy or conditions predisposing to neuropathy. In embodiments, the subject with a TB infection is pregnant. In embodiments, the subject with a TB infection is has injection drug use. In embodiments, the subject with a TB infection is a women belonging to a minority group, particularly in the postpartum period. In embodiments, the subject with a TB infection is a HIV seropositive.

In embodiments, detecting includes quantitating a level of the G191A NAT2 SNP, the C282T NAT2 SNP, the T341C NAT2 SNP, the G590A NAT2 SNP and the G857A NAT2 SNP. In embodiments, detecting includes quantitating a level of the G191A NAT2 SNP. In embodiments, detecting includes quantitating a level of the C282T NAT2 SNP. In embodiments, detecting includes quantitating a level of the T341C NAT2 SNP. In embodiments, detecting includes quantitating a level of the G590A NAT2 SNP. In embodiments, detecting includes quantitating a level of the G857A NAT2 SNP.

For the method provided herein, in embodiments, the method further includes administering an arylamine drug or a hydrazine drug at a dose greater than the prescribed dose where a G191A NAT2 SNP, C282T NAT2 SNP, T341C NAT2 SNP, G590A NAT2 SNP and G857A NAT2 SNP are not detected in said biological sample. In embodiments, the method further includes administering an arylamine drug at a dose greater than the prescribed dose where a G191A NAT2 SNP, C282T NAT2 SNP, T341C NAT2 SNP, G590A NAT2 SNP and G857A NAT2 SNP are not detected in said biological sample. In embodiments, the method further includes administering a hydrazine drug at a dose greater than the prescribed dose where a G191A NAT2 SNP, C282T NAT2 SNP, T341C NAT2 SNP, G590A NAT2 SNP and G857A NAT2 SNP are not detected in said biological sample. In embodiments the dosage is increased by at least about 50% to at least about 100%. In embodiments the dosage is increased by about 50% to about 100%. In embodiments the dosage is increased by about 55% to about 100%. In embodiments the dosage is increased by about 60% to about 100%. In embodiments the dosage is increased by about 65% to about 100%. In embodiments the dosage is increased by about 70% to about 100%. In embodiments the dosage is increased by about 75% to about 100%. In embodiments the dosage is increased by about 80% to about 100%. In embodiments the dosage is increased by about 85% to about 100%. In embodiments the dosage is increased by about 90% to about 100%. In embodiments the dosage is increased by about 95% to about 100%.

In embodiments the dosage is increased by about 50% to about 95%. In embodiments the dosage is increased by about 50% to about 90%. In embodiments the dosage is increased by about 50% to about 85%. In embodiments the dosage is increased by about 50% to about 80%. In embodiments the dosage is increased by about 50% to about 75%. In embodiments the dosage is increased by about 50% to about 70%. In embodiments the dosage is increased by about 50% to about 65%. In embodiments the dosage is increased by about 50% to about 60%. In embodiments the dosage is increased by about 50% to about 55%. In embodiments the dosage is increased by 50%, 55%, 60%, 65%, 70%, 75%, 80%, 85%, 90%, 95%, or 100%.

In embodiments, the method further includes administering an arylamine drug or a hydrazine drug at a dose less than the prescribed dose wherein: (a) two occurrences of G191A NAT2 SNP is detected, two occurrences of C282T NAT2 SNP is detected, two occurrences of T341C NAT2 SNP is detected, two occurrences of G590A NAT2 SNP is detected or two occurrences of G857A NAT2 SNP is detected; or, (b) at least two SNPs selected from the group including G191A NAT2 SNP, C282T NAT2 SNP, T341C NAT2 SNP, G590A NAT2 SNP and G857A NAT2 SNP are detected and the at least two SNPs reside on different chromosomes. In embodiments, the method further includes administering an arylamine drug or a hydrazine drug at a dose less than the prescribed dose, wherein: two occurrences of G191A NAT2 SNP is detected, two occurrences of C282T NAT2 SNP is detected, two occurrences of T341C NAT2 SNP is detected, two occurrences of G590A NAT2 SNP is detected or two occurrences of G857A NAT2 SNP is detected. In embodiments, the method further includes administering an arylamine drug at a dose less than the prescribed dose, wherein two occurrences of G191A NAT2 SNP is detected. In embodiments, the method further includes administering an arylamine drug at a dose less than the prescribed dose, wherein two occurrences of C282T NAT2 SNP is detected. In embodiments, the method further includes administering an arylamine drug at a dose less than the prescribed dose, wherein two occurrences of T341C NAT2 SNP is detected. In embodiments, the method further includes administering an arylamine drug at a dose less than the prescribed dose, wherein two occurrences of G590A NAT2 SNP is detected. In embodiments, the method further includes administering an arylamine drug at a dose less than the prescribed dose, wherein two occurrences of G857A NAT2 SNP is detected. In embodiments, the method further includes administering a hydrazine drug at a dose less than the prescribed dose, wherein two occurrences of G191A NAT2 SNP is detected. In embodiments, the method further includes administering a hydrazine drug at a dose less than the prescribed dose, wherein two occurrences of C282T NAT2 SNP is detected. In embodiments, the method further includes administering a hydrazine drug at a dose less than the prescribed dose, wherein two occurrences of T341C NAT2 SNP is detected. In embodiments, the method further includes administering a hydrazine drug at a dose less than the prescribed dose, wherein two occurrences of G590A NAT2 SNP is detected. In embodiments, the method further includes administering a hydrazine drug at a dose less than the prescribed dose, wherein two occurrences of G857A NAT2 SNP is detected. In embodiments, the method further includes administering an arylamine drug or a hydrazine drug at a dose less than the prescribed dose, wherein at least two SNPs from the group including G191A NAT2 SNP, C282T NAT2 SNP, T341C NAT2 SNP, G590A NAT2 SNP and G857A NAT2 SNP are detected and the at least two SNPs reside on different chromosomes. In embodiments, the method further includes administering an arylamine drug at a dose less than the prescribed dose, wherein at least two SNPs from the group including G191A NAT2 SNP, C282T NAT2 SNP, T341C NAT2 SNP, G590A NAT2 SNP and G857A NAT2 SNP are detected and the at least two SNPs reside on different chromosomes. In embodiments, the method further includes administering a hydrazine drug at a dose less than the prescribed dose, wherein at least two SNPs from the group including G191A NAT2 SNP, C282T NAT2 SNP, T341C NAT2 SNP, G590A NAT2 SNP and G857A NAT2 SNP are detected and the at least two SNPs reside on different chromosomes. In embodiments, the dosage is decreased by about 30% to about 50%. In embodiments, the dosage is decreased by about 35% to about 50%. In embodiments, the dosage is decreased by about 40% to about 50%. In embodiments, the dosage is decreased by about 45% to about 50%.

In embodiments, the dosage is decreased by about 30% to about 45%. In embodiments, the dosage is decreased by about 30% to about 40%. In embodiments, the dosage is decreased by about 30% to about 35%. In embodiments, the dosage is decreased by about 30%, 35%, 40%, 45%, or 50%.

In embodiments the drug is dapsone. In embodiments, the subject has a tuberculosis infection. In embodiments, the tuberculosis infection is latent. In embodiments, the tuberculosis infection is active. In embodiments, the drug is isoniazid, hydralazine, sulphadoxine, procainamide, or dapsone. In embodiments the drug is isoniazid. In embodiments the drug is hydralazine. In embodiments the drug is sulphadoxine. In embodiments the drug is procainamide.

In embodiments, the subject has a tuberculosis infection and the drug is isoniazid. In embodiments, the subject is an adult subject with active tuberculosis and the prescribed dose is 5 mg/kg up to 300 mg daily in a single dose; or 15 mg/kg up to 900 mg/day, two or three times/week. In embodiments, the subject is a minor subject with active tuberculosis and the prescribed dose is 10 mg/kg to 15 mg/kg up to 300 mg daily in a single dose; or 20 mg/kg to 40 mg/kg up to 900 mg/day, two or three times/week. In embodiments, the subject is an adult subject with drug-resistant tuberculosis and the prescribed dose is 15 mg/kg. In embodiments, the subject is an adult subject with a latent tuberculosis infection and the prescribed dose is 15 mg/kg. For preventative therapy of tuberculosis, the prescribed dose is 300 mg per day in a single dose for adults over 30 kg and 10 mg/kg (up to 300 mg daily) in a single dose.

Standard dosing for arylamine drugs and hydrazine drugs are well known in the art. For example, approved FDA labeling of isoniazid tablets manufactured by Sandoz Inc provides the following dosages 100 mg and 300 mg tablets for oral administration. Details regarding administration and dosage can be found at https://www.accessdata.fda.gov/drugsatfda_docs/label/2016/008678s0281b1.pdf; which is incorporated by reference herein in its entirety and for all purposes. Slow acetylation may lead to higher blood levels of the drug, and, thus, an increase in toxic reactions. Thus, the method described herein including embodiments thereof is contemplated to be useful for administering to a subject an arylamine drug or a hydrazine drug.

The method provided herein including embodiments thereof is contemplated to be useful for subjects taking an arylamine drug or a hydrazine drug or the subject is in need of an arylamine drug or a hydrazine drug, wherein the drug is taken for preventative therapy. For preventive therapy of tuberculous infection and treatment of tuberculosis, the following publications provide details regarding administration and dosage of therapeutics: The Recommendations of the Advisory Council for the Elimination of Tuberculosis, published in the MMWR: vol 42; RR-4, 1993; and Treatment of Tuberculosis and Tuberculosis Infection in Adults and Children, American Journal of Respiratory and Critical Care Medicine: vol 149; 1359-1374, 1994; which are incorporated by reference herein in their entirety and for all purposes.

As for Isoniazid tablets, the United States Pharmacopeia (USP) recommends as preventive therapy for the following groups, regardless of age. It is noted that the criterion for a positive reaction to a skin test (in millimeters of induration) for each group is given in parenthesis. 1) Persons with human immunodeficiency virus (HIV) infection (greater than or equal to 5 mm) and persons with risk factors for HIV infection whose HIV infection status is unknown but who are suspected of having HIV infection. Preventive therapy may be considered for HIV infected persons who are tuberculin-negative but belong to groups in which the prevalence of tuberculosis infection is high. Candidates for preventive therapy who have HIV infection should have a minimum of 12 months of therapy. 2.) Close contacts of persons with newly diagnosed infectious tuberculosis (greater than or equal to 5 mm). In addition, tuberculin-negative (less than 5 mm) children and adolescents who have been close contacts of infectious persons within the past 3 months are candidates for preventive therapy until a repeat tuberculin skin test is done 12 weeks after contact with the infectious source. If the repeat skin test is positive (greater than 5 mm), therapy should be continued. 3.) Recent converters, as indicated by a tuberculin skin test (greater than or equal to 10 mm increase within a 2-year period for those less than 35 years old; greater than or equal to 15 mm increase for those greater than or equal to 35 years of age). All infants and children younger than 4 years of age with a greater than 10 mm skin test are included in this category. 4.) Persons with abnormal chest radiographs that show fibrotic lesions likely to represent old healed tuberculosis (greater than or equal to 5 mm). Candidates for preventive therapy who have fibrotic Reference ID: 3957716 pulmonary lesions consistent with healed tuberculosis or who have pulmonary silicosis should have 12 months of isoniazid or 4 months of isoniazid and rifampin, concomitantly. 5.) Intravenous drug users known to be HIV-seronegative (greater than 10 mm). 6.) Persons with the following medical conditions that have been reported to increase the risk of tuberculosis (greater than or equal to 10 mm): silicosis; diabetes mellitus; prolonged therapy with adrenocorticosteroids; immunosuppressive therapy; some hematologic and reticuloendothelial diseases, such as leukemia or Hodgkin's disease; end-stage renal disease; clinical situations associated with substantial rapid weight loss or chronic undernutrition (including: intestinal bypass surgery for obesity, the postgastrectomy state [with or without weight loss], chronic peptic ulcer disease, chronic malabsorption syndromes and carcinomas of the oropharynx and upper gastrointestinal tract that prevent adequate nutritional intake). Candidates for preventive therapy who have fibrotic pulmonary lesions consistent with healed tuberculosis or who have pulmonary silicosis should have 12 months of isoniazid or 4 months of isoniazid and rifampin, concomitantly.

Additionally, in the absence of any of the above risk factors, it is contemplated that persons under the age of 35 with a tuberculin skin test reaction of 10 mm or more are appropriate candidates for preventive therapy if they are a member of any of the following high-incidence groups. 1.) Foreign-born persons from high-prevalence countries who never received BCG vaccine. 2.) Medically underserved low-income populations, including high-risk racial or ethnic minority populations, especially blacks, Hispanics and Native Americans. 3.) Residents of facilities for long-term care (e.g., correctional institutions, nursing homes and mental institutions).

Children who are less than 4 years old are candidates for isoniazid preventive therapy if they have greater than 10 mm induration from a PPD Mantoux tuberculin skin test. Also, persons under the age of 35 who a) have none of the above risk factors (1 to 6); b) belong to none of the high-incidence groups; and c) have a tuberculin skin test reaction of 15 mm or more, are appropriate candidates for preventive therapy. Also, the use of isoniazid is recommended for those with the additional risk factors listed above (1 to 6) and on an individual basis in situations where there is likelihood of serious consequences to contacts who may become infected.

In embodiments, the subject with a TB infection is one or more of the following: 1. Daily users of alcohol. Daily ingestion of alcohol may be associated with a higher incidence of + isoniazid hepatitis. 2. Patients with active chronic liver disease or severe renal dysfunction. 3. Age greater than 35. 4. Concurrent use of any chronically administered medication. 5. History of previous discontinuation of isoniazid. 6. Existence of peripheral neuropathy or conditions predisposing to neuropathy. 7. Pregnancy. 8. Injection drug use. 9. Women belonging to minority groups, particularly in the postpartum period. 10. HIV seropositive patients.

Slow acetylation may lead to higher blood levels of the drug, therefy leading to a potential increase in toxic reactions. Thus, the method provided herein including embodimens thereof are is contemplated to be useful for monitoring overdosages of an arylamine drug or a hydrazine drug. Thus, for the method provided herein, in embodiments the subject administered isoniazid can be monitored for overdosage. In embodiments the subject administered isoniazid can be monitored for symptoms of overdosage. Isoniazid overdosage symptoms can occur within 30 minutes to 3 hours after ingestion. Isoniazid overdosage symptoms include nausea, vomiting, dizziness, slurring of speech, blurring of vision and visual hallucinations. Isoniazid overdosage symptoms include respiratory distress, CNS depression, seizures, metabolic acidosis, acetonuria and hyperglycemias.

III. Methods of Detecting Multiple Genetic Targets

The method provided herein, including embodiments thereof is contemplated to be useful in settings with minimal laboratory infrastructure. For example, the haplotype prediction algorithm has over 99% accuracy, exceeding previous tools, and can be used to guide isoniazid dosing in treatment of tuberculosis. Additionally, as described herein, a molecular Beacon probe was developed and validated to be specific to the IS6110 gene specific to Mycobacterium tuberculosis complex (MTBC) for simultaneous detection of pathogen in clinical samples. The IS6110 probe was tested for its specificity on single-plex qPCR. Thus, in embodiments, the IS6110 and NAT2 assays are combined on a single platform.

Thus, for the method provided herein including embodiments thereof, detection includes detection of multiple genetic targets in a point-of-care device. In embodiments, the multiple genetic targets are targets in a pathogen and in a host. The number of genetic targets for the pathogen and host nucleic acids can vary for differing uses, for example specific assays for tuberculosis, HIV, invasive bacterial infections, viral respiratory infections. For this method, amplification of genetic material (RNA/DNA) from the pathogen and host can be performed on the same sample and platform, and results returned together. For example, the readout indicates the presence or absence of particular PCR-targets indicating pathogens present, and the presence or absence of SNPs/indels in pathogen genes indicating drug-resistance. Additionally, results can indicate whether SNPs in particular human genes related to drug-metabolism are present. From this, prediction of metabolic haplotype can be determined. Thus, using this method, the pathogen, and predicted optimized treatment dose are returned to the user.

Thus, in an aspect, is provided a method for detecting single polypeptide polymorphisms in a sample from a subject having or suspected of having tuberculosis, the method including detecting a G191A NAT2 SNP, a C282T NAT2 SNP, a T341C NAT2 SNP, a G590A NAT2 SNP and a G857A NAT2 SNP in a sample from said subject. In embodiments, provided herein is a method for detecting single polypeptide polymorphisms in a sample from a subject having or suspected of having tuberculosis, the method including detecting a G191A NAT2 SNP. In embodiments, provided herein is a method for detecting single polypeptide polymorphisms in a sample from a subject having or suspected of having tuberculosis, the method including detecting a C282T NAT2 SNP. In embodiments, provided herein is a method for detecting single polypeptide polymorphisms in a sample from a subject having or suspected of having tuberculosis, the method including detecting a T341C NAT2 SNP. In embodiments, provided herein is a method for detecting single polypeptide polymorphisms in a sample from a subject having or suspected of having tuberculosis, the method including detecting a G590A NAT2 SNP. In embodiments, provided herein is a method for detecting single polypeptide polymorphisms in a sample from a subject having or suspected of having tuberculosis, the method including detecting a G857A NAT2 SNP in a sample from said subject.

In embodiments, detecting includes polymerase chain reaction (PCR) assay detection.

For the method provided herein, in embodiments, detecting includes quantitating a level of the G191A NAT2 SNP, the C282T NAT2 SNP, the T341C NAT2 SNP, the G590A NAT2 SNP and the G857A NAT2 SNP. In embodiments, detecting includes quantitating a level of the G191A NAT2 SNP. In embodiments, detecting includes quantitating a level of the C282T NAT2 SNP. In embodiments, detecting includes quantitating a level of the T341C NAT2 SNP. In embodiments, detecting includes quantitating a level of the G590A NAT2 SNP. In embodiments, detecting includes quantitating a level of the G857A NAT2 SNP.

In embodiments, based on detecting of the G191A NAT2 SNP, the C282T NAT2 SNP, the T341C NAT2 SNP, the G590A NAT2 SNP and the G857A NAT2 SNP, a dose of isoniazid is determined for treating the subject for tuberculosis. In embodiments, based on detecting of the G191A NAT2 SNP, a dose of isoniazid is determined for treating the subject for tuberculosis. In embodiments, based on detecting of the C282T NAT2 SNP, a dose of isoniazid is determined for treating the subject for tuberculosis. In embodiments, based on detecting of the T341C NAT2 SNP, a dose of isoniazid is determined for treating the subject for tuberculosis. In embodiments, based on detecting of the G590A NAT2 SNP, a dose of isoniazid is determined for treating the subject for tuberculosis. In embodiments, based on detecting of the G857A NAT2 SNP, a dose of isoniazid is determined for treating the subject for tuberculosis.

In embodiments, the sample is sputum, blood, saliva or an oral swab. In embodiments, the sample is sputum. In embodiments, the sample is blood. In embodiments, the sample is an oral swab. In embodiments, the sample is saliva. In embodiments, the subject is being treated with isoniazid.

In another aspect is provided a method of treating a subject with a tuberculosis infection, the method including administering isoniazid to the subject at a dose greater than the isoniazid prescribed dose where a G191A NAT2 SNP, C282T NAT2 SNP, T341C NAT2 SNP, G590A NAT2 SNP and G857A SNPG857A NAT2 SNP are not detected in a biological sample from the subject.

In another aspect is provided a method of treating a subject with a tuberculosis infection, the method including administering isoniazid to the subject at a dose less than the isoniazid prescribed dose where: (a) two occurrences of G191A NAT2 SNP is detected in a biological sample from the subject, two occurrences of C282T NAT2 SNP is detected in a biological sample from the subject, two occurrences of T341C NAT2 SNP is detected in a biological sample from the subject, two occurrences of G590A NAT2 SNP is detected in a biological sample from the subject, or two occurrences of G857A SNPG857A NAT2 SNP is detected in a biological sample from the subject or, (b) at least two SNPs selected from the group consisting of G191A NAT2 SNP, C282T NAT2 SNP, T341C NAT2 SNP, G590A NAT2 SNP and G857A NAT2 SNP are detected in a biological sample from the subject and the at least two SNPs reside on different chromosomes.

In embodiments, the method includes administering isoniazid to the subject at a dose less than the isoniazid prescribed dose where: two occurrences of G191A NAT2 SNP is detected in a biological sample from the subject, two occurrences of C282T NAT2 SNP is detected in a biological sample from the subject, two occurrences of T341C NAT2 SNP is detected in a biological sample from the subject, two occurrences of G590A NAT2 SNP is detected in a biological sample from the subject, or two occurrences of G857A NAT2 SNP is detected in a biological sample from the subject. In embodiments, the method includes administering isoniazid to the subject at a dose less than the isoniazid prescribed dose where two occurrences of G191A NAT2 SNP is detected in a biological sample from the subject. In embodiments, the method includes administering isoniazid to the subject at a dose less than the isoniazid prescribed dose where two occurrences of C282T NAT2 SNP is detected in a biological sample from the subject. In embodiments, the method includes administering isoniazid to the subject at a dose less than the isoniazid prescribed dose where two occurrences of T341C NAT2 SNP is detected in a biological sample from the subject. In embodiments, the method includes administering isoniazid to the subject at a dose less than the isoniazid prescribed dose where two occurrences of G590A NAT2 SNP is detected in a biological sample from the subject. In embodiments, the method includes administering isoniazid to the subject at a dose less than the isoniazid prescribed dose where two occurrences of G857A SNPG857A NAT2 SNP is detected in a biological sample from the subject.

In embodiments, the method includes administering isoniazid to the subject at a dose less than the isoniazid prescribed dose where at least two SNPs selected from the group consisting of G191A NAT2 SNP, C282T NAT2 SNP, T341C NAT2 SNP, G590A NAT2 SNP and G857A NAT2 SNP are detected in a biological sample from the subject and the at least two SNPs reside on different chromosomes.

In embodiments, for the method provided herein, a nucleic acid probe is used. In embodiments, the nucleic acid probe to G191A NAT2 SNP includes the sequence of SEQ ID NO:7. In embodiments, the nucleic acid probe to G191A NAT2 SNP is the sequence of SEQ ID NO:7. In embodiments, the nucleic acid probe to C282T NAT2 SNP includes the sequence of SEQ ID NO:8. In embodiments, the nucleic acid probe to C282T NAT2 SNP is the sequence of SEQ ID NO:8. In embodiments, the nucleic acid probe to T341C NAT2 SNP includes the sequence of SEQ ID NO:9. In embodiments, the nucleic acid probe to T341C NAT2 SNP is the sequence of SEQ ID NO:9. In embodiments, the nucleic acid probe to G590A NAT2 SNP includes the sequence of SEQ ID NO:10. In embodiments, the nucleic acid probe to G590A NAT2 SNP is the sequence of SEQ ID NO:10. In embodiments, the nucleic acid probe to G857A NAT2 SNP includes the sequence of SEQ ID NO:11. In embodiments, the nucleic acid probe to G857A NAT2 SNP is the sequence of SEQ ID NO:11. In embodiments, the nucleic acid probe detects the presence of a pathogen. In embodiments, the nucleic acid probe includes the sequence of SEQ ID NO:14. In embodiments, the nucleic acid probe is the sequence of SEQ ID NO:14.

IV. Kits

The kits provided herein including embodiments thereof detect the occurences of the NAT2 SNPs (e.g. G191A NAT2 SNP, C282T NAT2 SNP, T341C NAT2 SNP, G590A NAT2 SNP, G857A NAT2 SNP) described herein. The presence or absence of the NAT2 SNPs are contemplated to predict if a subject is a rapid, intermediate or slow acetylator. For example, the detection of at least one SNP may indicate the subject is a slow acetylator. Slow acetylation may be a predictor that the subject has slow clearance of a therapeutic. In this instance, the subject may require a small dose of a therapeutic (e.g. an arylamine drug or a hydrazine drug) acetylated by NAT2. In another example, if SNPs are not detected, the subject may be a fast acetylator. Fast acetylation may be apredictor that the subject has fast clearance of a therapeutic. In this instand, the subject may require a larger dose of a therapeutic (e.g an arylamine drug or a hydrazine drug) acetylated by NAT2. Thus, in an aspect is provided a kit for determining acetylator type in a subject, the kit including nucleic acid probes to G191A NAT2 SNP, C282T NAT2 SNP, T341C NAT2 SNP, G590A NAT2 SNP and G857A NAT2 SNP.

In embodiments, the nucleic acid probe to G191A NAT2 SNP includes the sequence of SEQ ID NO:7. In embodiments, the nucleic acid probe to G191A NAT2 SNP is the sequence of SEQ ID NO:7. In embodiments, the nucleic acid probe to C282T NAT2 SNP includes the sequence of SEQ ID NO:8. In embodiments, the nucleic acid probe to C282T NAT2 SNP is the sequence of SEQ ID NO:8. In embodiments, the nucleic acid probe to T341C NAT2 SNP includes the sequence of SEQ ID NO:9. In embodiments, the nucleic acid probe to T341C NAT2 SNP is the sequence of SEQ ID NO:9. In embodiments, the nucleic acid probe to G590A NAT2 SNP includes the sequence of SEQ ID NO:10. In embodiments, the nucleic acid probe to G590A NAT2 SNP is the sequence of SEQ ID NO:10. In embodiments, the nucleic acid probe to G857A NAT2 SNP includes the sequence of SEQ ID NO:11. In embodiments, the nucleic acid probe to G857A NAT2 SNP is the sequence of SEQ ID NO:11. In embodiments, at least one probe is labeled. For example, the at least one probe can be labeled with a detectable moiety. In embodiements, the detectable moiety is a fluorescent molecule.

In embodiments, the kit can further detect presence of a pathogen. In embodiments, the pathogen is tuberculosis. Thus, in embodiments, the nucleic acid probe includes the sequence of SEQ ID NO:14. In embodiments, the nucleic acid probe is the sequence of SEQ ID NO:14.

In embodiments, the kit further includes amplification primers. In embodiments, the amplification primers can be complementary to a portion or fragment of the NAT2 gene. In embodiments, the amplification primer includes the sequence of SEQ ID NO:1. In embodiments, the amplification primer is the sequence of SEQ ID NO:1. In embodiments, the amplification primer includes the sequence of SEQ ID NO:2. In embodiments, the amplification primer is the sequence of SEQ ID NO:2. In embodiments, the amplification primer includes the sequence of SEQ ID NO:3. In embodiments, the amplification primer is the sequence of SEQ ID NO:3. In embodiments, the amplification primer includes the sequence of SEQ ID NO:4. In embodiments, the amplification primer is the sequence of SEQ ID NO:4. In embodiments, the amplification primer includes the sequence of SEQ ID NO:5. In embodiments, the amplification primer is the sequence of SEQ ID NO:5. In embodiments, the amplification primer includes the sequence of SEQ ID NO:6. In embodiments, the amplification primer is the sequence of SEQ ID NO:6.

In embodiments, the amplification primers can be complementary to a portion or a fragment of the IS6110 gene. In embodiments, the amplification primer includes the sequence of SEQ ID NO:12. In embodiments, the amplification primer is the sequence of SEQ ID NO:12. In embodiments, the amplification primer includes the sequence of SEQ ID NO:13. In embodiments, the amplification primer is the sequence of SEQ ID NO:13.

In embodiments, the kit further includes a polymerase. In embodiments, the polymerase is Aptataq exo-DNA polymerase.

In embodiments, the kit includes the reagents as provided in Table 8. In embodiments, the reagents are provided in one container. In embodiments, the reagents are provided in separate containers. In embodiments, the reagents are provided in a concentration that is the working concentration. In embodiments, the reagents are provided in a concentration greater than the working concentration. In embodiments, the reagents are provided in a 2×, 5×, or 10× concentration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Introduction to Exemplary Experiments

More than 50 years after its introduction, isoniazid (INH) remains one of the major first line drugs used to treat active and latent tuberculosis infections (14,15). There has been an increasing number of genetic markers identified that predict metabolism and toxicities from various antimicrobials. INH is among the most well characterized of these, with more than 80% of its pharmacokinetic variability explained by mutations in the gene encoding arylamine N-acetyltransferase 2 (NAT2), responsible for its metabolism in the liver (16-18). The primary step in the metabolism of INH is acetylation, catalyzed by the NAT2 enzyme, resulting in the formation of acetyl-INH. The NAT2 enzyme displays genetic polymorphism, and its activity is expressed at highly variable levels. A high correlation between INH acetylator phenotype and seven most frequent SNPs in NAT2 gene has been demonstrated by several studies (19-22). Individuals can be classified into three phenotypes—rapid, intermediate, and slow acetylators—according to whether they carry polymorphisms on neither, one, or both copies of this gene, respectively. Rapid acetylators typically have the lowest plasma INH concentrations, while slow acetylators have high concentrations (23). A worldwide population survey on NAT2 acetylation phenotype reported that more than half of the global population are slow or rapid acetylators (18). A meta-analysis of 14 studies, comprising 474 cases and 1446 controls based on NAT2 polymorphisms found that rapid acetylators are twice as likely to have microbiological failure and acquired drug resistance. Additionally, a significant association has been consistently observed between NAT2 slow acetylators and the risk of anti-tuberculosis drug-induced liver injury (17). Additional meta-analyses have identified a three- to four-fold increased risk of hepatotoxicity among slow acetylators (24). A randomized trial of pharmacogenomic guided dosing for tuberculosis treatment found that, compared with standard dosing, it reduced hepatotoxicity among slow acetylators and increased treatment response at 8 weeks among rapid acetylators (25)

Despite this evidence, pharmacogenomic testing and guided treatment has not entered the mainstream of clinical practice for tuberculosis. Few clinical laboratories perform NAT2 genotyping, which requires detection of multiple polymorphisms and testing for heterozygous allele patterns. Such testing is not widely available in resource-constrained environments where the majority of tuberculosis burden falls. To address this gap, Applicant developed an algorithm from unphased SNP patterns, derived from globally representative genomic data, to predict INH metabolism phenotype using fewer SNPs while retaining high accuracy. Based on the SNP combination derived from this model, a prototype NAT2 pharmacogenomic (NAT2-PGx) assay was further developed on a commercial, automated PCR platform (GeneXpert) to detect NAT2 polymorphisms. Applicant demonstrates herein that this tool can accurately predict INH clearance rates directly from clinical samples and can be easily performed with minimal training and hands-on time.

EXAMPLE 1

Development of a Rapid Pharmacogenomic Assay for NAT2 Polymorphisms to Guide Isoniazid Dosing for Treatment of Tuberculosis Described herein is an approach that will address current limitations in effective treatment of infectious diseases through rapid detection of pharmacogenetic markers of antimicrobial metabolism and toxicity that will be performed concurrently with rapid detection of pathogens on the same sample. Clinical samples, such as blood, sputum, saliva, and oral swab, typically have pathogen DNA as well as abundant human DNA present in them. Molecular assays that target single nucleotide polymorphisms (SNPs) associated with drug metabolism and toxicity on a point-of-care testing platform are used. In a short time, this platform can report what pathogen is present, and what drug-metabolism markers are present in the patient. The latter can be interpreted automatically to inform the clinician about risks of toxicities and the appropriate dosing adjustments. In sum, this platform can inform what drug should be used, for what duration and at what dose, using a single patient sample.

This approach can have immediate applications in treatment of active and latent tuberculosis as well as HIV infections. Globally, there are 9.6 million cases of tuberculosis annually and over 30 million prevalent cases of HIV requiring treatment. Additionally, over 2 billion people have latent tuberculosis who would benefit from treatment, for which isoniazid is the primary treatment. In the United States, there are 9000 cases of active tuberculosis annually and over 9 million individuals with latent tuberculosis. Additionally, this approach may have application in management of other infectious diseases for which pharmacogenomic predictive variants are already known or are identified.

Thus, a rapid pharmacogenomic assay for detection of NAT2 polymorphism to guide isoniazid treatment of TB was developed. Isoniazid (INH) is an important first line antitubercular drug used to treat active and latent tuberculosis infections. High INH levels in plasma are strongly associated with hepatotoxicity, while low drug levels are a determinant of treatment failure, slow response, and emergence of drug resistance. Common polymorphisms in the N-acetyltransferase 2 gene (NAT2) explain about 80% of intra-individual variability in drug levels, and numerous clinical studies have shown that NAT2 haplotypes strongly predict drug-induced hepatotoxicity and treatment failure. A recent randomized trial demonstrated that pharmacogenomic (PGx) guided dosing isoniazid reduced hepatotoxicity and improved treatment response. Additionally, Applicants' recent analysis showed that NAT2 polymorphism-based pharmacogenomic test for stratified isoniazid dosing in treatment of active TB is cost effective and improves health outcomes.

A phenotype prediction algorithm was developed to predict INH acetylation levels in TB patients based on NAT2 polymorphisms. Applicant identified 5 NAT2 SNPs-G191A, C282T, T341C, G590A and G857A which could predict phased genotype with >99.9% accuracy, which is predictive of phenotype. These five polymorphisms were used to develop NAT2/PGx assay, which Applicant successfully demonstrated on an automated DNA extraction and real-time PCR platform (GeneXpert). Multicolor melt curve analysis (MMCA) was used to calculate melt Tm difference between mutant, heterozygous and wild types. The data generated were used to predict acetylator phenotype by NAT2 phenotype predictor algorithm. The polymorphism data were validated on Sanger sequencing. NAT2/PGx assay could detect all five NAT2 polymorphisms including heterozygous alleles with 100% accuracy directly from whole blood in 140 minutes. The assay developed here is easy to perform and could be utilized in settings with minimal laboratory infrastructure. Applicant's haplotype prediction algorithm has over 99% accuracy, exceeding previous tools, and could be used to guide isoniazid dosing in treatment of tuberculosis. Additionally, molecular Beacon probe was developed and validated specific to IS6110 gene specific to Mycobacterium tuberculosis complex (MTBC) for simultaneous detection of pathogen in clinical sample. The IS6110 probe was tested for its specificity on single-plex qPCR. The IS6110 and NAT2 assays are further combined on a single platform.

EXAMPLE 2

Material & Methods

NAT2 Phenotype Prediction Algorithm

Using NAT2 gene sequencing data from a globally representative database of 8,561 individuals, random forest models were trained to predict the phased haplotype from partial, unphased SNP data. Phased haplotypes were mapped to phenotypes from a global NAT2 database. Two-thirds (⅔) of the data was used for training using leave-one-out cross validation, and then the remaining ⅓ was used for testing using the algorithm and the widely used NAT2Pred tool. In order to make the phenotype prediction model equally reliable to predict phenotype in any population globally, 191G>A polymorphisms was included, which is commonly found in African population but not included in NAT2Pred.

Sample Details

For assay optimization and validation on GeneXpert cartridge, blood samples from healthy individuals were obtained from Stanford blood center.

For phenotype prediction from genotype derived from qPCR assays, 48 sputum samples from active TB cases were collected in DNA preservative in Mato Grosso do Sul in Brazil. DNA was extracted and shipped to Stanford by Dr. Julio Croda, Federal University of Grande Dourados, Brazil. Additionally, plasma samples were collected at 1 hour and 8 hours after first dose on day 2 and after 1 hour on day 14 to analyze plasma drug levels.

Thirteen standardized DNA samples from Coriell Institute were also procured for assay development and optimization Quantification of INH and Acetyl-INH Levels in Plasma Plasma samples from patients with active TB were collected at 1 hour and 8 hours after first dose on day 2 and after 1 hour on day 14. Drug levels for INH and acetyl-INH were quantified by High-performance liquid chromatography (HPLC).

DNA Extraction

Genomic DNA from 100 ul of whole blood was extracted using Qiagen Blood and tissue kit (#69504) as per the manufacturer's instructions. The DNA was eluted in 30 ul DNAse free water and quantified on Qubit. 100 ng of DNA was used for Sanger sequencing validation. For sputum samples, DNA was extracted from 1 ml decontaminated sputum using QIAamp DNA Mini Kit (#51304)

Primer and Probe Designing and Validation

For Host NAT2 Polymorphisms

In order to achieve high specificity for melting temperature detection, the probes were designed and selected in such a way that the mutant and wild type has a minimum of 2-degree temperature difference. Primers and probes were manually designed and were validated using Beacon Designer, Premier Biosoft International, Palo, CA (version 8). Three sets of primers were designed to amplify the sequences spanning 191, 282, 341, 590 and 857 positions on NAT2 exon2. Sloppy molecular beacon probes which bind to mutant and wild type regions resulting in different Tms were designed and validated for any cross talk and non-specific binding. The five NAT2 probes; NAT2-191G>A, NAT2-282C>T, NAT2-341 C>T NAT2-590A>G and NAT2-857G>A were labelled at their 5' terminal with Cy5.5, Alexa647, Alex532, FAM and Alexa405 fluorescent dyes respectively.

TABLE 1

List of primers used in NAT2/PGx assay

| Primers | SEQ ID NO. |
|---|---|
| -NAT2-FP1-<br>5'-CATGGAGTTGGGCTTAGAGG-3' | 1 |
| -NAT2-RP1-<br>5'-AGCTTCCAGACCCAGCATC-3' | 2 |
| -NAT2-FP2-<br>5'-GTGCCTTGCATTTTCTGCTT-3' | 3 |
| -NAT2-RP2-<br>5'-GCAAGGAACAAAATGATGTGG-3' | 4 |

TABLE 1-continued

| List of primers used in NAT2/PGx assay | |
|---|---|
| Primers | SEQ ID NO. |
| -NAT2-FP3<br>-5'-ACTGTTTGGTGGGCTTCATC-3' | 5 |
| -NAT2-RP3-<br>5'-GAGTTGGGTGATACATACACAAGG-3' | 6 |

TABLE 2

| List of probes used in NAT2-PGx assay | |
|---|---|
| Probes | SEQ ID NO. |
| NAT2-191G > A-Cy5.5-CGGCGCTGTA AGAAGAAACCAGGGTGGGTGGTGTGCGCCG | 7 |
| NAT2-282C > T-Alex647-CGCAGCGTA TTTTTACATCCCTCCAGTTAACAAATACAGC GCTGCG | 8 |
| NAT2-341T > C-Alex532-GGCGAGGGT GACCATTGACGGCAGGAATTACATTGTCTCG CC | 9 |
| NAT2-590A > G-FAM- GCCGCGCGCTTGAACCTCAAACAATTGAAG ATTTTGAGTCGCGGC | 10 |
| NAT2-857C > A-Alexa405- CGCGGCCAAACCTGGTGATGAATCCCTTAC TATTTAGAAGCCGCG | 11 |

Probe for Pathogen Detection

A primer set amplifying 183 bp region of IS6110 gene and molecular beacon probe specific to IS6110, labelled with FAM fluorophore at 5' terminal was further designed and validated.

Primers for Sanger Sequencing

For DNA sequencing, an 823 bp fragment of the NAT2 gene (819-1641 bp of the gene code) was amplified using the forward primer 5'-GGGCTGTTCCCTTTGAGA-3' (SEQ ID NO:15) and reverse primer 5'-TAGTGAGTTGGGTGA-TAC-3' (SEQ ID NO:16).

Single-Plex Real Time PCR for Assay Development and Optimization

Single-plex real time PCR assays were developed to optimize and validate primers and probes. Five probes corresponding to NAT2 polymorphisms were labelled with FAM and BHQ quencher at their 5' and 3' termini respectively. The assay was performed in a 20 μl reaction mix. A 20 ul total reaction volume was set up using 10 ng genomic DNA per assay. PCR mastermix included (0.5 ul of 2U Aptataq exo-DNA polymerase, 1× betaine, 1× Aptataq buffer, 4 mM MgCl2, 1× ROX passive reference dye, 60 nM FP, 1000 nM reverse primers, 250 uM of each probe). PCR was initiated by 10 min of denaturation—activation at 95° C., followed by 50 cycles at 95° C. for 15 sec (denaturation), annealing at 60° C. for 15 s and extension at 76° C. for 20 sec. The melting program included three steps: denaturation at 95° C. for 1 min, followed by renaturation at 35° C. for 3 min and a continuous reading of fluorescence from 45 to 85° C. by heating at increments of 0.03° C./s.

Multicolor Melt Curve Analysis on GeneXpert Platform

Asymmetric PCR and melt curve analysis were performed on a GeneXpert IV instrument using GeneXpert Dx 4.8 software (Cepheid, Sunnyvale). Flex cartridge-01 (Cepheid) were used to perform automated DNA extraction from whole blood followed by PCR amplification and melt curve analysis to detect SNPs. PCR and melt conditions were optimized using mastermix prepared in house. The NAT2-PGx assay was performed in an 80 ul reaction volume (70 ul mastermix and 10 ul eluted DNA). Briefly, 100 ul of whole blood was mixed with 900 ul of lysis buffer (Cepheid) in a 1.5 ml Eppendorf tube. The sample was vortexed for 2-3 sec and incubated at room temperature for 2 min. The entire 1 ml whole blood and lysis buffer mix was loaded into sample preparation chamber of flex cart-01 for automated DNA extraction. 70 ul PCR mastermix was simultaneously loaded in the PCR reaction chamber of the flex cart-01. The GeneXpert was programmed to elute DNA in 10 ul volume which was used for the NAT2-PGx assay. PCR mastermix included (2 ul of 2U Aptataq exo-DNA polymerase, 1× Betaine, 1× PCR additive reagent, 1× Aptataq buffer, 8 mM MgCl2, 400 nM FP, 900 nM reverse primers, 500 nM of 191-Cy5.5 and 857-Alexa-405, 430 nM 282-Alexa-647 and 590-FAM and 300 nM 341-Alexa-537 probes). PCR was initiated at holding stage—50° C. for 2 min, initial denaturation at 94° C. for 2 min, followed by 50 cycles of denaturation at 95° C. for 15 sec, annealing at 57° C. for 30 sec and extension at 65° C. for 60 sec. The melting program included three steps: denaturation at 95° C. for 1 min, followed by renaturation at 40° C. for 3 min and a continuous reading of fluorescence from 40 to 72° C. by heating at increments of 0.05° C./sec. The MMCA curve was analyzed using the GXP version 4.8 software.

Melt Curve Data Interpretation

Single-plex assays were performed on StepOne plus (Applied Biosystems) real time PCR to assess the Tm difference between mutant and wildtypes. Tm values for the mutant and wild types calculated by melt curve analysis were manually validated by analyzing melt curves from 50 DNA samples from TB patients plus 13 DNA samples from Coriell. Once finalized, the GeneXpert software was programmed to detect the specific melting temperatures and call them as homozygous mutant, homozygous wild type and heterozygous. The final result was displayed as—PCR positive; Mutation type for all 5 SNVs. The Tm results were then used to predict acetylator phenotype using NAT2 phenotype prediction algorithm.

EXAMPLE 3

Results

Accuracy of NAT2 Phenotype Algorithm

Using a random forest model trained on two thirds of the data (n=5,738), out-of-sample phenotype prediction accuracy from unphased data on the remaining one third (n=2,823) was 100% for 5 SNPs model.

TABLE 3

Out-of-sample prediction accuracy of unphased NAT2 SNP data for acetylation phenotype in random forest models. Models were trained with 5,738 individuals and tested on 2,823 individuals. Sens: sensitivity. Spec: specificity.

| NAT2 SNP Positions | SNP number | Accuracy | 95% CI | Sens. Rapid | Spec. Rapid | Sens. Slow | Spec Slow |
|---|---|---|---|---|---|---|---|
| 191, 282, 341, 481, 590, 803, 857 | 7 | 1.000 | (0.999-1.000) | 1.000 | 1.000 | 1.000 | 1.000 |

TABLE 3-continued

Out-of-sample prediction accuracy of unphased NAT2 SNP data for acetylation phenotype in random forest models. Models were trained with 5,738 individuals and tested on 2,823 individuals. Sens: sensitivity. Spec: specificity.

| NAT2 SNP Positions | SNP number | Accu-racy | 95% CI | Sens. Rapid | Spec. Rapid | Sens. Slow | Spec Slow |
|---|---|---|---|---|---|---|---|
| 191, 282, 341, 481, 590, 857 | 6 | 1.000 | (0.999-1.000) | 1.000 | 1.000 | 1.000 | 1.000 |
| 191, 282, 341, 590, 857 | 5 | 1.000 | (0.999-1.000) | 1.000 | 1.000 | 1.000 | 1.000 |
| 282, 341, 590, 857 | 4 | 0.978 | (0.972-0.983) | 0.996 | 0.988 | 0.969 | 0.999 |
| 341, 590, 847 | 3 | 0.976 | (0.970-0.982) | 1.000 | 0.986 | 0.967 | 1.000 |

TABLE 3-continued

Out-of-sample prediction accuracy of unphased NAT2 SNP data for acetylation phenotype in random forest models. Models were trained with 5,738 individuals and tested on 2,823 individuals. Sens: sensitivity. Spec: specificity.

| NAT2 SNP Positions | SNP number | Accu-racy | 95% CI | Sens. Rapid | Spec. Rapid | Sens. Slow | Spec Slow |
|---|---|---|---|---|---|---|---|
| 341, 590 | 2 | 0.852 | (0.838-0.865) | 1.000 | 0.889 | 0.832 | 1.000 |

INH Metabolism and NAT2 Genotype

Drug levels for all four first line drugs and acetyl-INH were performed by HPLC. MTB DNA was detected in sputum of TB patients by GeneXpert MTB/RIF. Seven (7) single nucleotide variants in the NAT2 gene influencing metabolism of isoniazid were profiled. The TaqMan qPCR assays (Thermo Fischer Scientific) tested on sputum samples had perfect correlation in all cases with Sanger sequencing of the NAT2 gene from sputum and plasma. Isoniazid clearance was strongly predicted by qPCR-based NAT2 variant detection in sputum (FIGS. 1A-1B and 4A-4B). Additionally, it has been demonstrated that the number of slow metabolizing variants (regardless of their specific haplotype) predicts metabolism as well as haplotype reconstruction. Based on the recently developed algorithm, it has also been demonstrated that metabolism phenotype can be predicted by assaying fewer polymorphisms.

Single-Plex Assay Development and Validation

Reaction conditions for five NAT2 probes were independently optimized on Step-One plus real time PCR and analytical sensitivity and specificity were calculated for each assay. Of the 48 sputum positive individuals tested, 27 (56.2%) slow, 16 (33.3%) intermediate and 5 (10.4%) rapid. The specificity of melts to accurately detect SNPs was confirmed either by commercial single-plex assays or Sanger sequencing or both. The melt data was in 100% concordance with commercial assays in accurately detecting NAT2 SNPs.

To assess the analytical sensitivity and specificity of melt curve anaylsis to accurately detect NAT2 polymorphisms, 64 DNA samples were analyzed on single-plex PCR against five NAT2 positions. The assay showed high specificity, with the maximum standard deviation of 0.3 degree in the Tms between the samples. Additonally, the NAT2 polymorphism could be accurately detected in as low as 10 copies of NAT2 in the PCR reaction.

TABLE 4

Melting temperature (Tm) values for five NAT2 polymorphisms derived from DNA-probe hybrid melts using single-plex assays validated on 48 pulmonary TB patients

| NAT2 SNP position | Mutant Total samples analyzed | Wild type Total samples analyzed | Het Total samples analyzed | Mutant Tm ± SD | Wild type Tm ± SD | ΔTm (WT − MT) |
|---|---|---|---|---|---|---|
| 191 | 0 | 44 | 5 | 66.3 ± 0.28 | 61.92 ± 0.68 | 4.38 |
| 282 | 6 | 24 | 19 | 62.81 ± 0.40 | 66.85 ± 0.34 | 4.04 |
| 341 | 12 | 23 | 14 | 66.30 ± 0.48 | 68.70 ± 0.38 | 2.40 |
| 590 | 0 | 35 | 14 | 68.0 ± 0.28 | 64.37 ± 0.28 | 3.63 |
| 857 | 1 | 41 | 7 | 66.4 ± 0.11 | 62.72 ± 0.29 | 3.68 |

SD: Standard deviation,

ΔTm: DNA-probe hybrid melting temperature difference,

WT: Wild type,

MT: mutant

5-Plex MMCA Assay on GeneXpert Platform

Multiplex qPCR with five different fluorophores was developed using same probe sequences optimized on single-plex qPCR. Open cartridges manufactured and supplied by Cepheid; Sunnyvale were used to optimize reaction conditions with standardized DNA samples from Coriell. Once optimized the assay was transferred to Flex cartridges 01 provided by cepheid. Flex cart 01 allows automated DNA extraction followed by PCR and results are generated in 140 min. This makes it an ideal point-of care test. NAT2/PGx 5-plex assay produced reliable identification of all 5 SNPs directly from 50 ul of whole blood.

EXAMPLE 4

Description of NAT2 Haplotype Prediction Algorithm

The relationship between NAT2 haplotype and phenotype, as defined by metabolism of isoniazid and other substrates, is well characterized. One of the main challenges with developing a diagnostic based on measuring single nucleotide polymorphisms (SNPs) is predicting the haplotype (i.e. the full genotype, accounting for both chromosome copies) from unphased genotypic data. Unphased genomic data are data in which the specific alignment along the chromosome are not known. For example, if an individual has SNPs in two positions, that could represent two SNPs on one chromosome, causing loss of function for one gene copy while the other is normal, or one SNP on each chromosome, results in two dysfunctional gene copies. Furthermore, with data available on only a partial number of the known function-determining SNPs, the challenge of prediction becomes even greater. A tool for predicting haplotype from unphased SNP data is known as "NAT2Pred", which makes predictions based on 6 SNPs. NAT2Pred was tested with globally representative data and found that the accuracy was only 94.4%. Then the algorithm herein was trained on separate global data and tested it on that same test set. It was found that with only 5 SNPs, the algorithm described herein achieved 100% accuracy in predicting haplotype. After training, the algorithm will take the output of the assay, which is whether each of the 5 genomic positions contains homozygous wild type, heterozygous (one wild type, one mutation) or homozygous alternate (both mutants), and make a prediction of whether the individual has a "slow metabolizer", "intermediate metabolizer" or "rapid metabolizer" phenotype. It also provides a probability assigned with each of these states.

The haplotype prediction algorithm markedly outperformed the existing state of the art algorithm ("NAT2Pred"), which showed 94.4% accuracy using 6 SNPs on the test dataset, whereas Applicant's algorithm achieved 100% accuracy using only 5 SNPs.

There does not appear to be existing methods for: point-of-care detection of pathogens and pharmacogenomic markers (human SNP variants) on the same sample and platform. Nor have any combination of these been applied in treatment of infectious diseases. Additionally, performing SNP testing directly often of a non-invasive sample (sputum) represents a novel component.

Thus, results shown herein demonstrate that automated the NAT2-PGx assay developed by Applicant is easy to perform and could be utilized in settings with minimal laboratory infrastructure. Given that tuberculosis treatment is usually initiated at the time of diagnosis, a rapid point of care test for INH dose adjustment would be highly beneficial. Moreover, the test developed here uses only 50 ul of whole blood. The assay can further be optimized to perform with lower volumes. In such case, a finger stick sample collection method could be used.

Variations and Modifications

Variations include sample type, assay type and diseases targeted. For example, sample types include the use of sputum, blood, urine, buccal swabs, or other bodily fluids which can be directly tested for pathogens and human DNA. Assay types include PCR-type SNP assays, which are well established, may be used on a point-of-care platform. Most immediate application will be TB and HIV due to Applicant's experience in these diseases, the large need/market, and the well-characterized human pharmacogenomics variants. However, additional commercial applications can include targeting of blood stream infections and antibiotics (e.g. *Staphylococcus aureus*, resistance gram negative organisms), sputum for bacterial and viral pathogens, urinary tract infections, etc.

Thus, features of this approach are: 1) An improved haplotype prediction algorithm that improves accuracy of phenotype prediction and therefore drug dosing; 2) that human genetic markers related to medication metabolism are detected simultaneously, from the same samples and on the sample platform as the genetic markers of pathogens and pathogen resistance; 3) the resultant information is then interpreted to provide the user with information on the appropriate therapies for the infection present, informed by the resistance and pharmacogenomics data.

EXAMPLE 5

A Rapid Pharmacogenomic Assay to Detect NAT2 Polymorphisms and Guide Isoniazid Dosing for Tuberculosis Treatment Standardized weight-based dose of anti-tubercular drugs contributes to a substantial incidence of toxicities, inadequate treatment response, and relapse, in part due to variable drug levels achieved. Single nucleotide polymorphisms (SNPs) in the N-acetyltransferase-2 (NAT2) gene explain the majority of interindividual pharmacokinetic variability of isoniazid (INH). However, an obstacle to implementing pharmacogenomic-guided dosing is the lack of a point-of-care assay. Thus, Applicant describes herein the development of a NAT2 classification algorithm, validation of its performance in predicting isoniazid clearance, and development of a prototype pharmacogenomic assay.

Applicant trained random forest models to predict NAT2 acetylation genotype from unphased SNP data using a global collection of 8,561 phased genomes. Forty-eight pulmonary TB patients were enrolled, sparse pharmacokinetic sampling was performed, and the acetylator prediction algorithm accuracy was tested against estimated INH clearance. Applicant then developed a cartridge-based multiplex qPCR assay on the GeneXpert platform and assessed its analytical sensitivity on whole blood samples from healthy individuals.

Measurements and main results indicated that a 5-SNP model trained on two-thirds of the data (n=5,738), out-of-sample acetylation genotype prediction accuracy on the remaining third (n=2,823) was 100%. Among the 48 TB patients, predicted acetylator types were: 27 (56.2%) slow, 16 (33.3%) intermediate and 5 (10.4%) rapid. INH clearance rates were lowest in predicted slow acetylators (median 19.3 L/hr), moderate in intermediate acetylators (median 41.0 L/hr) and highest in fast acetylators (median 46.7 L/hr). The cartridge-based assay accurately detected all allele patterns directly from 25 ul of whole blood. Thus, an automated pharmacogenomic assay on a platform widely used globally for tuberculosis diagnosis enables personalized dosing of isoniazid.

Methods

Datasets: The datasets used to develop the NAT2 classifier was obtained from the IGSR (International Genome Sample Resource, 1000 genomes project) and a meta-analysis by Sabbagh et. al (18, 26). Population information on the combined dataset is provided in Table 9.

NAT2 acetylator phenotype prediction classifier: Phased genomes from 8,561 individuals were used and haplotypes were labeled based on seven most frequent SNPs (both synonymous and non-synonymous) which are reported to affect the acetylation on INH-rs1801279 (191G>A), rs1041983 (282C>T), rs1801280 (3411>C), rs1799929 (481C>T), rs1799930 (590G>A), rs1208 (803A>G) and rs1799931 (857G>A) (19) in the NAT2 gene, following an international consensus nomenclature (27). An unphased dataset was then constructed containing only information on whether each sample was wild type for both alleles, homozygous variant for both alleles, or heterozygous. Applicant stratified the dataset by geographic region and then drew a random sample from two-thirds of each stratum for a training set and one third for an out-of-sample test set, to ensure geographic representativeness in the training and test sets. Applicant trained random forest models on the training set using the caret package in R and assessed classification performance on the held-out test set. Applicant began with a 7 SNP model and eliminated SNPs in sequential models according to the lowest variable importance factor.

Sample collection: Sputum and plasma samples from 48 newly diagnosed patients with active pulmonary tuberculosis were collected at the Federal University of Grande Dourados, Brazil. All participants were treated with standardized, weight-based doses of isoniazid, rifampicin, pyrazinamide and ethambutol. Plasma samples were collected at 1 hour and 8 hours after the first dose and after 1 hour on day 14. Plasma drug concentrations for isoniazid and acetyl-isoniazid were quantified by high-performance liquid chromatography coupled to tandem mass spectrometry (HPLC-MS) as previously described (28).

Pharmacokinetic analysis of INH clearance in tuberculosis patients: The population PK analysis was performed using the non-linear mixed effects modeling approach using NONMEM (version 7.4.3; ICON plc, Gaithersburg, MD, USA), PsN and R-based Xpose (version 4.7 and higher) (29,30). One-compartment model with a first-order absorption with a log normal distribution for inter-individual variability (IIV) on different PK parameter(s) as well as an additive and/or proportional model for the residual error were tested for the base model selection. Mixture models with two or three subpopulations representing different clearance rate were then evaluated. The first-order conditional estimation with interaction method (FOCEI) was applied and the model-building procedure and model selection was based on the log-likelihood criterion (the difference in the minimum OFV between hierarchical models was assumed to be Chi-square distributed with degrees of freedom equal to the difference in the number of parameters between models), goodness-of-fit plots (e.g. relevant residuals against time randomly distributed around zero), and scientific plausibility of the model. Visual predictive check was conducted to evaluate whether the final model with estimated fixed-effect parameters and covariates adequately describe data.

Sputum processing and host DNA extraction: Spontaneously expectorated sputum samples from confirmed pulmonary tuberculosis patients were collected in 10 mL of guanidine thiocyanate (GTC) solution. The samples were needle sheared and centrifuged at 3000 rpm for 30 min. The supernatant was collected in Trizol LS and host DNA was extracted from the supernatant using a manual extraction method described previously (31).

Primers and probes for melt curve analysis: Applicant first developed single-plex melt curve assays based on molecular beacon probe chemistry for five NAT2 polymorphisms. Using same primer and probe sequences, Applicant further developed multiplex NAT2-PGx assay compatible on GeneXpert platform. Three sets of primers and five molecular beacon probes spanning the NAT2 gene were used. Primers and probes were designed using Beacon Designer (Premier Biosoft International, Palo, CA; version 8). The primers and probes sequences with their corresponding fluorophores and quenchers are as described herein.

NAT2-genotyping on pulmonary TB samples: Host genomic DNA extracted from 48 sputum samples from TB positive patients was used to perform single-plex qPCR assays developed in-house. The assays were validated using TaqMan commercial genotyping assays (NAT2 TaqMan® SNP Genotyping Assays, Applied Biosystems). The genotyping was performed on StepOne Plus Real Time PCR (Applied Biosystems). The NAT2-genotypes derived from the assays were used to predict INH acetylator phenotype by Applicant's 5-SNP model.

Automated NAT2-PGx Multiplex PCR and melt curve analysis: Applicant combined the five single-plex NAT2 melt curve assays validated on TB samples into one and developed a multiplex assay (NAT2-PGx) on the FleXible Cartridge (Flex cart-01, Cepheid) platform. Flex cart allows automated DNA extraction from whole blood followed by PCR amplification and melt curve analysis to detect SNPs in NAT2 gene in a single run. NAT2-PGx assay was performed on a GeneXpert IV instrument using GeneXpert Dx 4.8 software (Cepheid, Sunnyvale). Briefly, 100 ul of whole blood was mixed with 900 ul of GeneXpert lysis buffer for whole blood (Cepheid), incubated for 2 min at room temperature and loaded into sample preparation chamber of the flex cart for automated DNA extraction. A 70 ul of PCR mastermix was simultaneously loaded in the PCR reaction chamber of the flex cart-01. PCR and melt conditions were optimized using mastermix prepared in house.

The multiplex assay was validated on blood samples from 20 healthy individuals. The accuracy of multiplex NAT2-PGx assay in SNP calling was subsequently validated by Sanger sequencing (see methods). Applicant assessed analytical sensitivity of the assay and robustness to input blood volume by performing it on varying volumes of whole blood (200 ul, 100 ul, 50 ul, 25 ul) and comparing the Tm results and standard deviation for each position across blood volumes.

Results:

SNP Selection and Development of Acetylation Prediction Model

Complete phased data for the seven polymorphisms that define acetylation haplotypes were available for 8,561 individuals from 59 populations. The dataset contains 3,573 (41.7%) individuals with a slow genotype, 3,428 (40.0%) individuals with an intermediate genotype, and 1,560 (18.2%) individuals with a rapid genotype (See Table 5). The highest proportion of rapid acetylators were in East Asia (40%), and three regions had prevalence of slow acetylator phenotypes over 50% (Central and South Asia, Europe and North Africa). Applicant used these phased allele data to select SNPs for inclusion in an assay measuring unphased SNPs. Using a random forest model trained on two thirds of the data (n=5,738), out-of-sample phenotype prediction accuracy from unphased data on the remaining one third (n=2,823) was 100% for models using 7, 6 or 5 SNPs. With 4 SNPs, prediction accuracy was 98.0% (95% CI: 97.4-98.5%), and a 3 SNP model had similar performance (98.0%; 95% CI: 97.4-98.4%) (Table 3). However, both of these models performed poorly on data from Sub-Saharan Africa (4 SNP model accuracy: 82.5%, 95% CI: 78.1-86.4%); 3 SNP model accuracy: 81.3%, 95% CI: 76.8-85.3%). Based on these results, Applicant selected the 5 SNP model (191G>A, 282C>T, 341T>C, 590G>A and 857G>A) to take forward for clinical validation and diagnostic development.

TABLE 5

Summary of populations included in genomic analysis and their acetylation genotypes.

| Region | Number of individuals | Acetylation Genotype, n (%) Slow | Intermediate | Rapid |
|---|---|---|---|---|
| Americas | 1,112 | 432 (39%) | 463 (42%) | 217 (20%) |
| Central and South Asia | 588 | 355 (60%) | 198 (34%) | 35 (6%) |
| East Asia | 2,308 | 340 (15%) | 1049 (45%) | 919 (40%) |

TABLE 5-continued

Summary of populations included in genomic analysis and their acetylation genotypes.

| Region | Number of individuals | Acetylation Genotype, n (%) Slow | Intermediate | Rapid |
|---|---|---|---|---|
| Europe | 3,458 | 1966 (57%) | 1249 (36%) | 243 (7%) |
| North Africa | 44 | 30 (68%) | 10 (23%) | 4 (9%) |
| sub-Saharan Africa | 1,051 | 450 (43%) | 459 (44%) | 142 (14%) |
| Total | 8,561 | 3573 (42%) | 3428 (40%) | 1560 (18%) |

Genotype Correlation with Isoniazid Clearance in Patients with Tuberculosis

A cohort of 48 patients were enrolled with newly diagnosed pulmonary tuberculosis and collected plasma at 1 hour and 8 hours after dose on day 1 and at 1 hour after dose on day 14. To detect five NAT2 polymorphisms identified by Applicant's classifier, single-plex melt curve qPCR assays developed in-house using host DNA extracted from sputum samples were performed. Additionally, Applicant used commercial 7-SNP single-plex genotyping assays and compared the results with 5-SNP single-plex PCR to validate the melt curve accuracy in SNP detection. There was 100% concordance in terms of SNP detection between single-plex melt curve and commercial 7-SNP assays. Of the 48 individuals for whom NAT2 genotypes were profiled, DNA-probe hybrid melting temperature difference (ΔTm) (° C.) between wild-type and mutant alleles for positions 191, 282, 341, 590 and 857 were found to be 4.38, 4.04, 2.40, 3.63 and 3.68 respectively. Both mutant and wild type probes had a minimum 2.40° C. Tm difference which allowed SNP calling with high accuracy (Table 4).

Figure 4A:
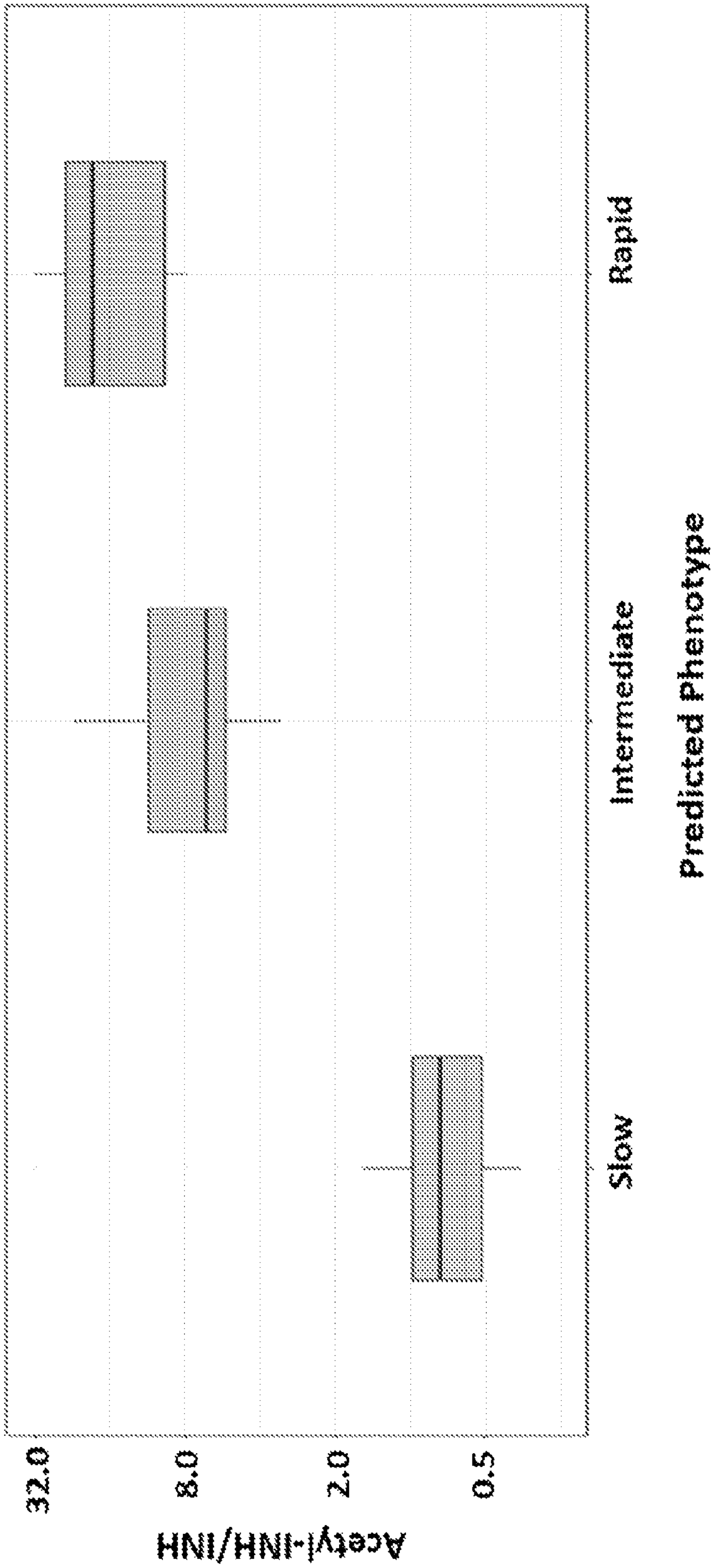
FIGS. 4A-4B show the predicted NAT2 phenotype from sputum samples and associated acetylation ratio and isoniazid clearance rates from patients receiving tuberculosis treatment. The (FIG. 4A) 8 hour acetyl-INH to INH ratio and (FIG. 4B) isonazid clearance rates, according to acetylation phenotype predicted from 5 SNPs, measured in sputum samples from 48 patients receiving treatment for active tuberculosis.
Figure 4B:
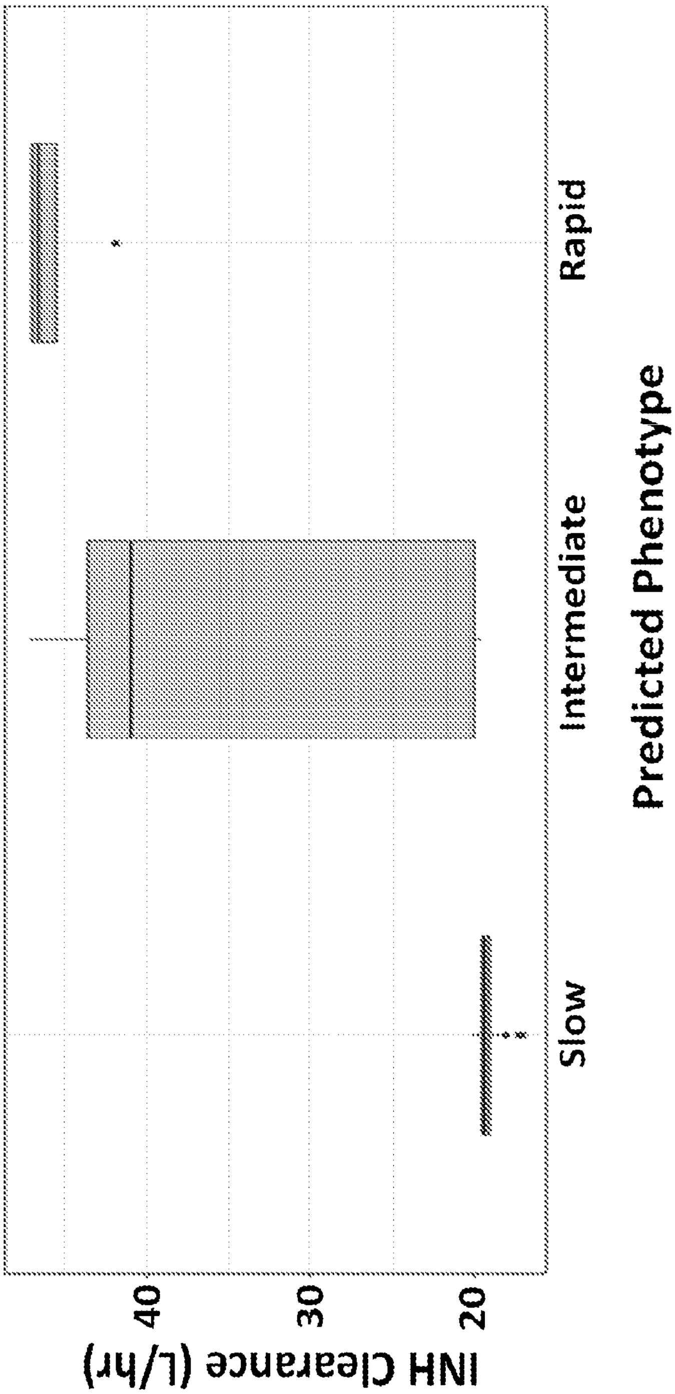

Phenotypes were further predicted from 5-SNP using the algorithm described above as well as a publicly available tool (NAT2Pred) (32), which uses a 6 SNP model that excludes rs1801279 (191G>A) and includes other two sites from 7-SNP model-rs1799929 (481C>T) and rs1208 (803A>G) when compared with Applicant's 5-SNP model. Among the 48 participants, predicted acetylator types from the 5 SNP assay were: 27 (56.2%) slow, 16 (33.3%) intermediate and 5 (10.4%) rapid. NAT2Pred classified 4 samples as intermediate that were classified as rapid (n=1) or slow (n=3) by the 5 SNP classifier. Among those classified as slow by the 5 SNP classifier and intermediate by NAT2Pred, acetyl-INH to INH ratios at 8 hours were 0.61, 0.38, 0.41, consistent with slow acetylation (median: 0.76, range 0.36-1.55) rather than intermediate acetylation (median 6.67, range 3.32-22.21) and suggesting misclassification by NAT2Pred. The sample classified as intermediate by NAT2PRed and rapid by the 5 SNP classifier had an acetyl-INH to INH ratio of 9.8, which fell between the median values, and within both ranges, for intermediate and rapid acetylators (range 8.09-∞). Phenotypes predicted by the 5 SNP classifier were strongly predictive of INH acetylation and clearance (FIGS. 4A and 4B). INH clearance rates were lowest in slow acetylators (median 19.3 L/hr), moderate in intermediate acetylators (median 41.0 L/hr) and highest in fast acetylators (median 46.7 L/hr).

Development of an Automated Pharmacogenomic Assay

Figure 5:
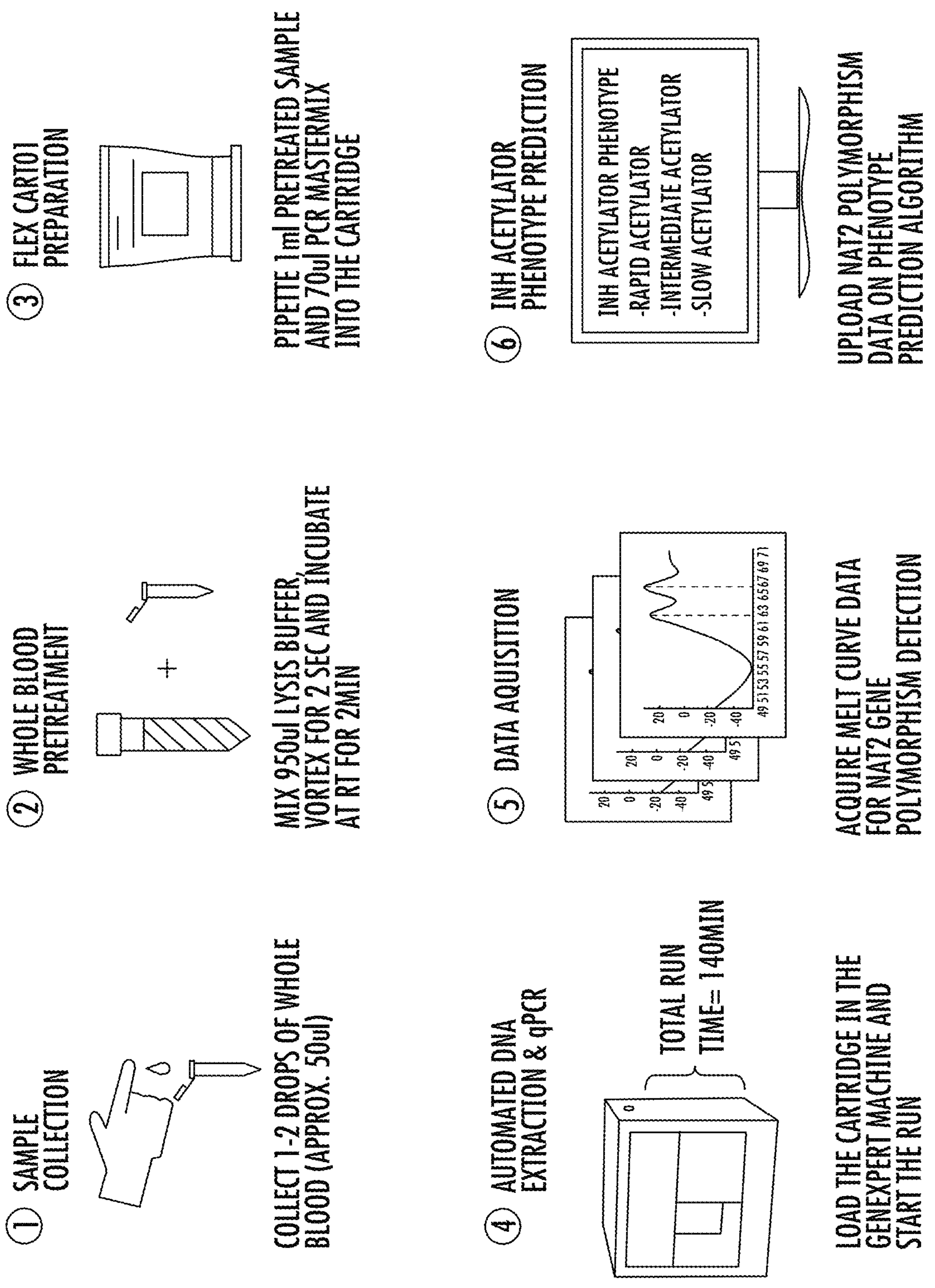
FIG. 5 illustrates schemata for the automated NAT2 Pharmacogenomic assay. 1-2 drops of blood is collected in an Eppendorf tube and mixed with lysis buffer to a total of 1 ml, which is then loaded onto a GeneXpert Flex01 cartridge and placed into a GeneXpert instrument for automated DNA extraction, qPCR and meltcurve analysis. Allele patterns for each of the 5 SNPs are determined by Tm analysis, and the resulting data are used to predict acetylator phenotype.
Figure 6:
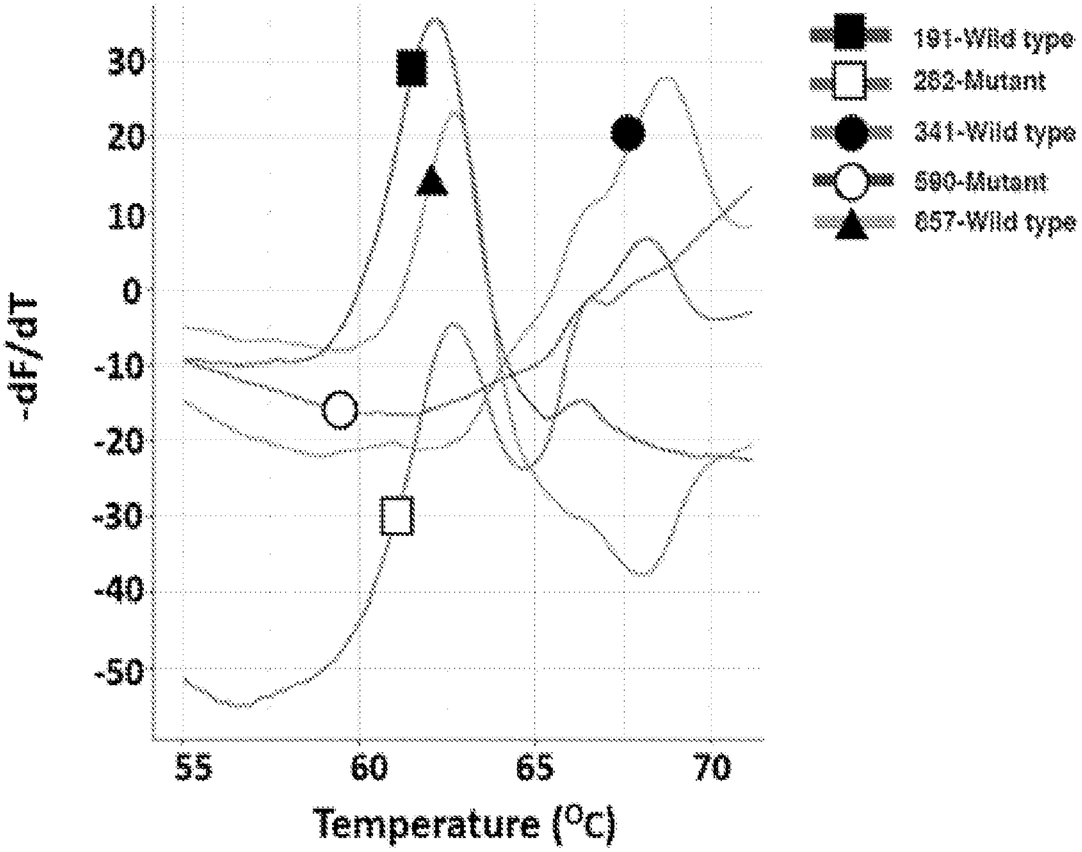
FIG. 6 shows negative derivative transformed melt curves for the five NAT2 gene polymorphisms. The shift in melt curve temperature is observed during a nucleotide exchange. Molecular beacon probes are first hybridized and then melted off of their NAT2 target amplicon. The melt curves indicate wild type alleles at positions 191 (black square), 341 (black circle) and 857 (black triangle); and mutant alleles at positions 282 (white square) and 590 (white circle).
Figure 7A:
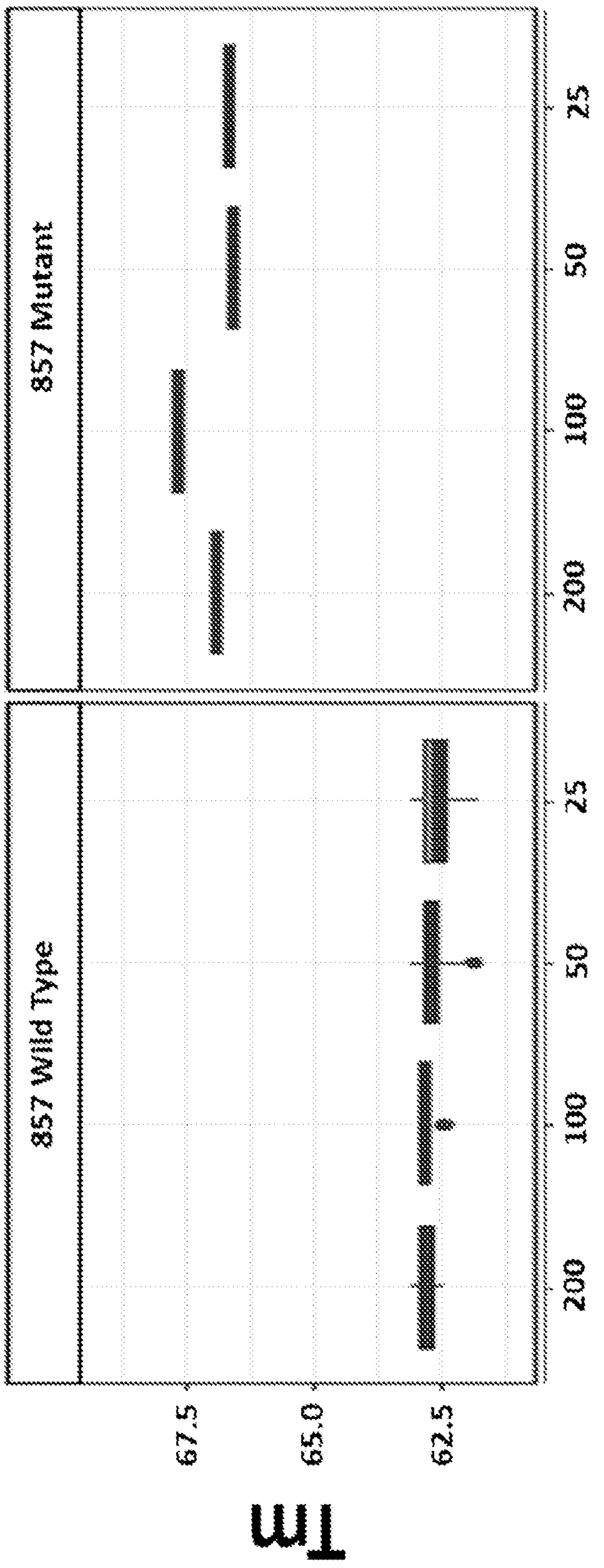
FIGS. 7A-7E illustrates the effect of whole blood sample volume on melting temperature for wild type and mutant alleles at 5 positions in NAT2: NAT2 polymorphisms were accurately detected at all volumes with sufficient different in melting temperature (Tm) to distinguish wild type from mutant alleles at positions 857 (FIG. 7A), 341 (FIG. 7B), 282 (FIG. 7C), and 590 (FIG. 7D). None of the individuals in this dataset had mutations at position 191 (FIG. 7E).
Figure 7B:
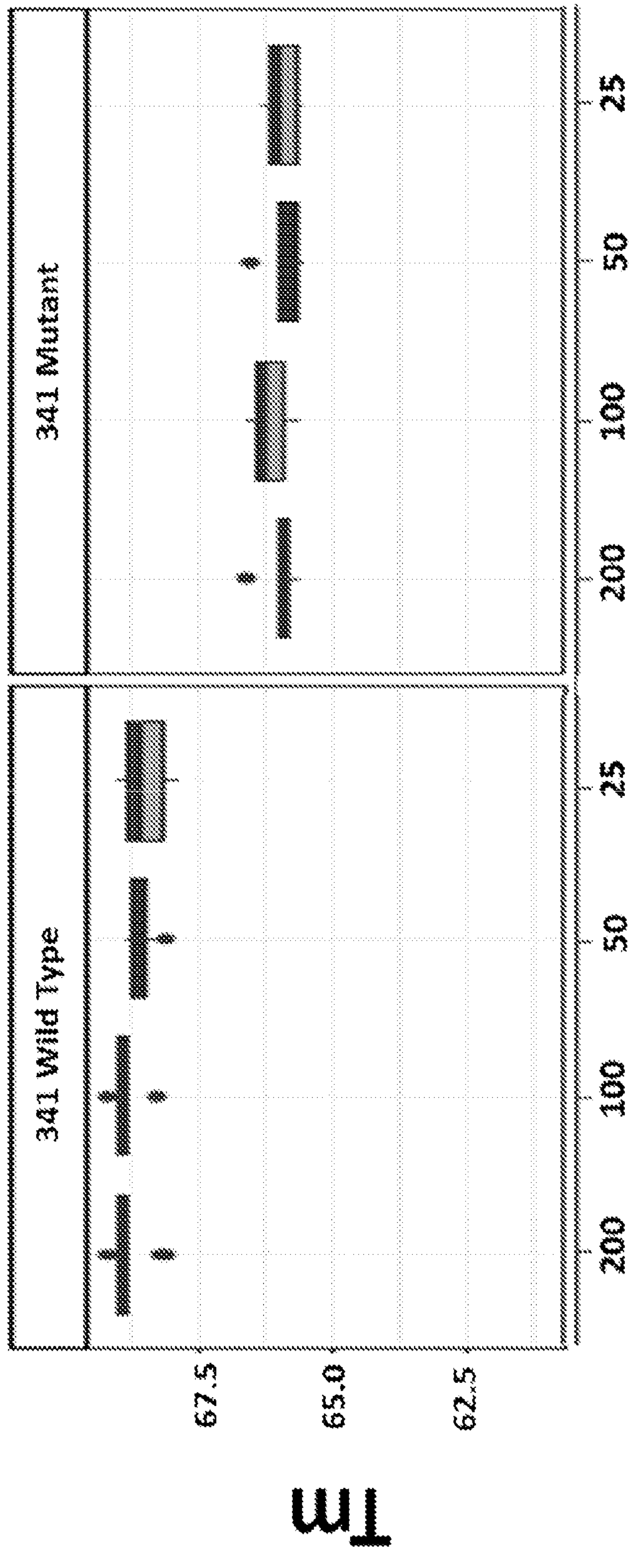
Figure 7C:
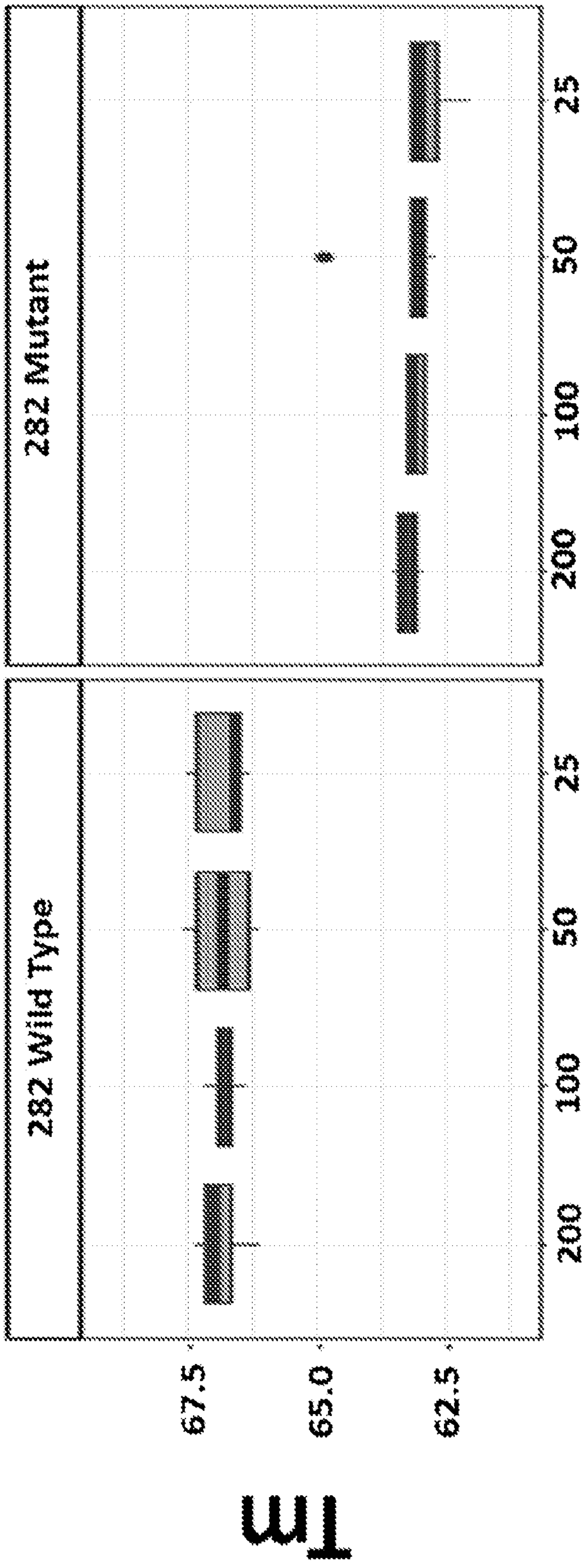
Figure 7D:
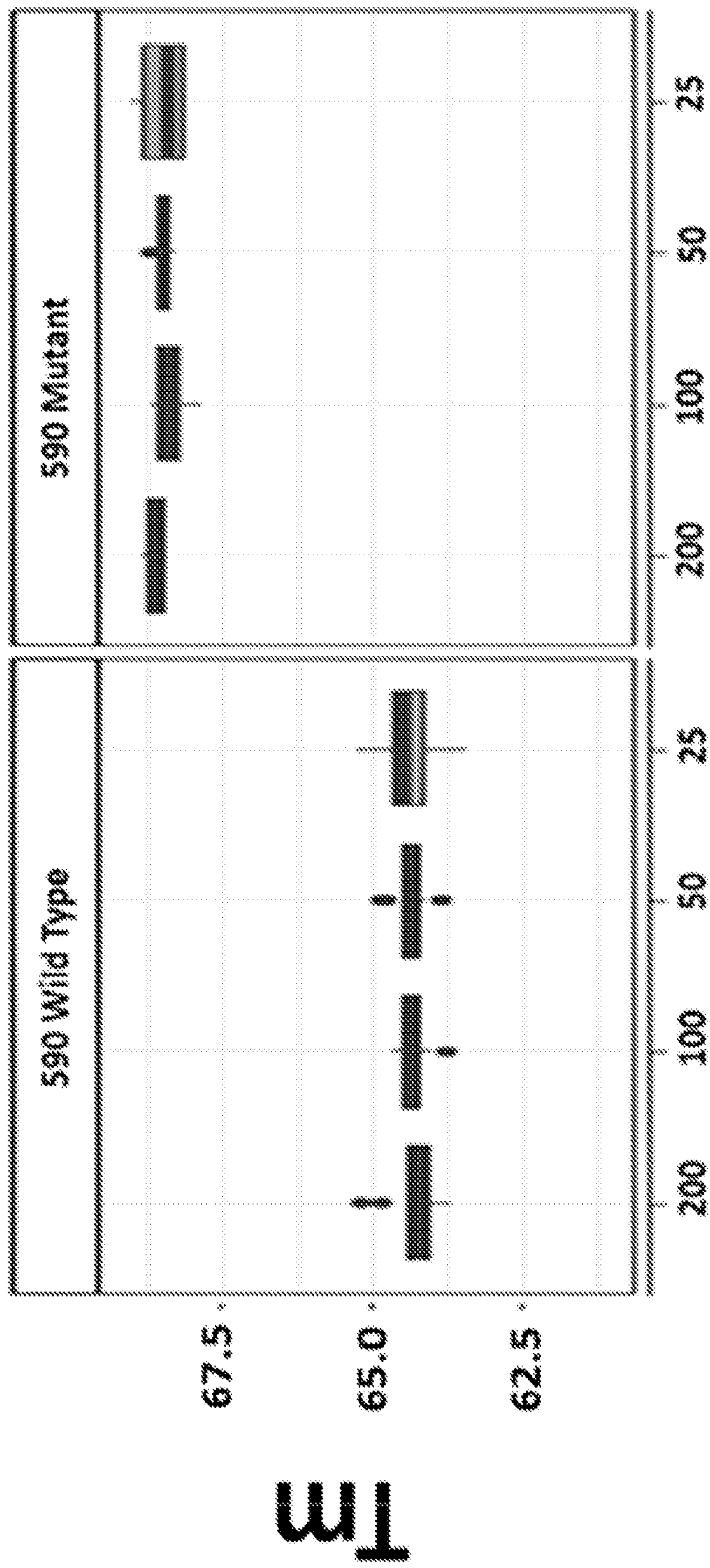
Figure 7E:
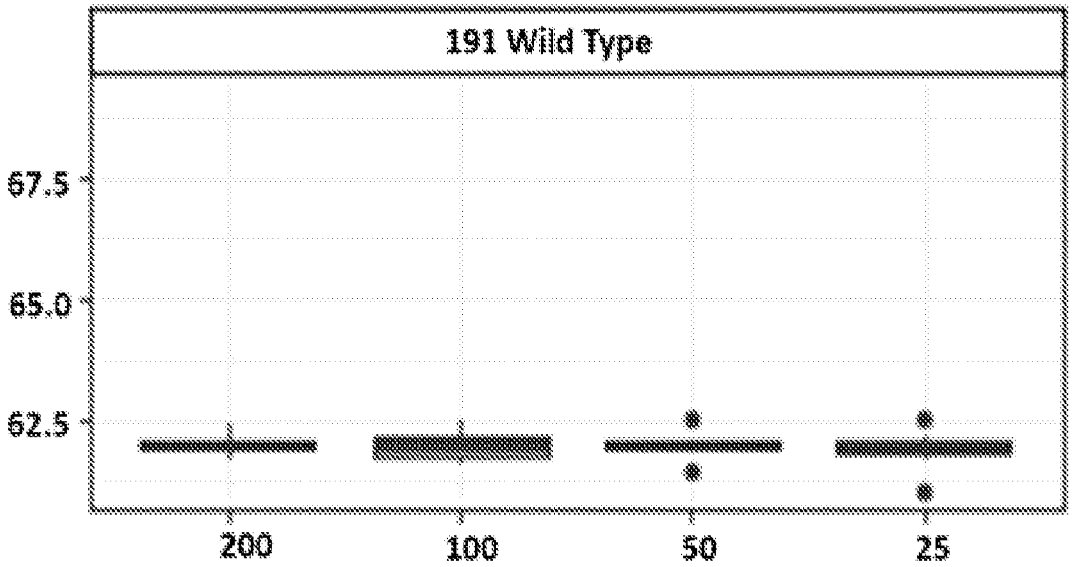

Applicant validated the NAT2-PGx assay on 20 whole blood samples from healthy individuals. The hands-on time for the cartridge preparation per sample was 5 minutes followed by 140 minutes for overall run that included automated DNA extraction (FIG. 5). Mutant, wild-type and heterozygous alleles were manually called based on peak patterns and Tm values detected in melt curves. Negative derivative transformed melt curves from five NAT2 gene polymorphisms are shown in FIG. 6. The assay detected all polymorphisms with 100% accuracy (average SD in Tm across all probes=0.34° C.) compared with Sanger sequencing. The NAT2 genotypes corresponding to 20 blood samples covered all three categories—mutant, wild-type and heterozygous for five NAT2 positions except for NAT2-191 for which all samples were all wild-type. The 191G>A mutation is highly prevalent in African and African-American populations and is less common in other populations (33). Among the 20 samples, predicted acetylator types using the 5-SNP classifier were: 8 (40%) slow, 10 (50%) intermediate and 2 (10%) rapid (Table 10).

Applicant further assessed the analytic performance of the NAT2-PGx assay at lower sample volumes. The assay could accurately detect all melt peaks with as low as 25 ul of sample volume. The variability in Tm from five NAT2 probes for sample volumes 200 ul-25 ul is shown in FIGS. 7A-7E. NAT2 polymorphisms were accurately detected at all volumes (Table 11) and demonstrated robustness to variation in input volume.

Discussion

Despite availability of effective treatment for drug-sensitive tuberculosis, a substantial proportion of population encounters drug associated toxicity or treatment failure, much of which could be averted through dosing guided by genetic markers of drug metabolism (34). It was previously found that pharmacogenomic guided dosing of isoniazid could be highly cost-effective in low- and middle-income countries (35). A major barrier to its implementation has been the lack of a simple, scalable assay that could be used at points of care where tuberculosis is treated in resource-constrained settings. To address this gap, globally representative genomic data was used to identify patterns of 5 SNPs that enable accurate prediction of isoniazid acetylator phenotype, validating this with pharmacokinetic data of patients receiving tuberculosis treatment. Applicant then developed a prototype automated pharmacogenomic assay on the GeneXpert platform, which is widely available globally but had never been applied to pharmacogenomics. Applicant found that this assay could robustly distinguish wild type, mutant and heterozygous alleles from a range of blood volumes as low as 25 ul, making it suitable for use with venous blood samples or finger-stick blood samples. The assay requires minimal hands-on time for sample preparation, which would facilitate its use in resource-constrained settings.

An earlier model ("NAT2Pred") predicted NAT2 acetylation phenotype from unphased genomic data; however, it had moderate error rates in distinguishing intermediate from rapid acetylators (33). Moreover, error rates among individuals from Sub-Saharan Africa were 14%, in part due to the exclusion of the G191A (R64Q) SNP, common to the NAT2*14 allele cluster, which is frequent in Africans and African-Americans, but virtually absent in Caucasian, Indian, and Korean populations (36). A recent study using the set of 6 NAT2 SNPs included in NAT2Pred, but not including G191A, found no correlation between NAT2 genotype and INH acetylation phenotype in HIV-infected, Zulu individuals with culture-confirmed tuberculosis in Durban, South Africa (37), underscoring the importance of including this SNP in genotype predictions in this region.

Indeed, ethnic differences in SNP frequencies are responsible for the differences in frequency of rapid, intermediate and slow acetylator NAT2 haplotypes (18, 23). Applicant trained the SNP classifier with globally representative data, which resulted in the selection and inclusion of the G191A SNP in the model and assay. This is particularly important as Sub-Saharan Africa bears a substantial burden of tuberculosis disease and mortality as well as HIV co-infection, which is independently associated with greater pharmacokinetic variability and tuberculosis treatment toxicity (38, 39).

The association between acetylation polymorphisms and INH metabolism was first demonstrated in 1959, and their importance was well characterized in subsequent decades through phenotypic descriptions (40-42). Subsequent genotypic descriptions confirmed that NAT2 polymorphisms predicted INH early bactericidal activity, and clinical outcomes including hepatotoxicity, relapse and acquisition of drug resistance. Further dosing studies demonstrated that provision of lower doses to slow acetylators and higher doses to rapid acetylators could achieve target concentrations (43). One randomized trial of pharmacogenomic-guided dosing of INH during active tuberculosis treatment found that it significantly reduced toxicities (among slow acetylators) and treatment non-response (among rapid acetylators). Taken together, the evidence for pharmacogenomic guided dosing to achieve consistent drug levels and improve clinical outcomes is strong. Automated, easy-to-use assays could enable pharmacogenomic guided isoniazid dosing in resource constrained settings, where a substantial burden of the world's tuberculosis occurs.

The findings of this study are subject to several limitations. Applicant tested the assays on 48 individuals with active tuberculosis and 20 healthy individuals with a diverse representation of polymorphisms, but the number of participants with G191A mutations was limited (n=5). A larger validation study involving testing on whole blood, including from finger stick capillary blood, is needed to assess real-world performance of this assay under field conditions. Due to unavailability of whole blood samples from TB patients, sputum samples were used to extract host DNA for genotyping. Further studies should also investigate testing on non-invasive samples including sputum, saliva or oral swabs, from which DNA is abundant. Second, Applicant focused on NAT2 polymorphisms, as they explain majority of interindividual pharmacokinetic variability, though polymorphisms in several other genes have been associated with hepatotoxicity. However, these associations have been comparatively modest and somewhat inconsistent (44-45). Applicant focused on INH and did not include other important tuberculosis drugs, such as rifampicin. The evidence base for pharmacogenomic markers predicting rifampin pharmacokinetics is less robust, and findings concerning clinical outcomes such as toxicities or treatment response are limited (46-49). However, given the importance of this drug class in treatment of active and latent tuberculosis, and emerging evidence supporting greater efficacy of higher doses of rifampin, further investigation of pharmacogenomic markers in rifampicin is needed. Future assays may include polymorphisms influencing rifampicin metabolism to further optimize treatment of tuberculosis.

Since the demonstration of the efficacy of six month, short-course chemotherapy in 1979, standardized treatment for drug susceptible tuberculosis using weight-based doses has remained essentially unchanged. Additionally, INH remains a major component of regimens for treatment of latent tuberculosis, which is recommended by the WHO for young children, HIV-infected individuals and household contacts of tuberculosis cases (50). More than half the world's population have slow or rapid acetylation phenotypes, which put them at risk for excessive drug levels resulting in drug toxicities or insufficient drug levels putting them at risk of acquired drug resistance or disease relapse. Dose adjustment based on NAT2 acetylation genotyping can achieve consistent, target drug levels and reduce the incidence of poor clinical outcomes. A prototype automated, cartridge-based assay was developed that can reliably predict acetylation phenotype directly from as low as 25 ul of whole blood. By developing this for the GeneXpert platform, which is widely used in low- and middle-income countries for tuberculosis diagnosis, this assay could make personalized tuberculosis treatment dosing available in resource-constrained settings. Further studies are needed to evaluate its accuracy and clinical impact in real-world clinical settings.

EXAMPLE 6

Supplementary Methods

Primers and Probes for Melt Curve Analysis

Three sets of primers spanning the NAT2 gene were used for single-plex and multiplex PCR. Primers and sloppy molecular beacon (SMB) probes were designed using Beacon Designer (Premier Biosoft International, Palo, CA; version 8). Three of 5 molecular beacon probes (NAT2-191, NAT2-590 and NAT2-857) were designed with 100% complementarity towards mutant alleles and two (NAT2-282 and NAT2-341) were 100% specific to wild type alleles. For single-plex assays, all probes were labelled with FAM at their 5' end and BHQ-1 at 3'. For the multiplex assay on GeneXpert, FAM was replaced with other fluorophores except for NAT2-590.

Single-Plex PCR and Melt Curve Analysis on Pulmonary TB Patients

Genomic DNA extracted from sputum samples from TB positive patients was used for single-plex assays performed on StepOne Plus Real Time PCR. A 20 ul total reaction volume was set up using 10 ng genomic DNA per assay. PCR mastermix included (0.5 ul of 2U Aptataq exo-DNA polymerase, 1× betaine, 1× Aptataq buffer, 4 mM MgCl2, 1× ROX passive reference dye, 60 nM FP, 1000 nM reverse primers, 250 uM of each probe). PCR was initiated by 10 min of denaturation-activation at 95° C., followed by 50 cycles at 95° C. for 15 sec (denaturation), annealing at 60° C. for 15 s and extension at 76° C. for 20 sec. The melting program included three steps: denaturation at 95° C. for 1 min, followed by renaturation at 35° C. for 3 min and a continuous reading of fluorescence from 45 to 85° C. by heating at increments of 0.03° C./s. The MMCA curve was analyzed using the StepOne Plus software version 2.0. For single-plex melt curve assay validation, TaqMan 7-SNP genotyping assays were performed using commercial assays (NAT2 TaqMan® SNP Genotyping Assays, Applied Biosystems) on DNA extracted from sputum samples from 49 pulmonary TB patients on a StepOne Plus Real Time PCR machine.

Automated NAT2-PGx Multiplex PCR and Melt Curve Analysis

Asymmetric PCR and melt curve analysis were performed on a GeneXpert IV instrument using GeneXpert Dx 4.8 software (Cepheid, Sunnyvale). Flex cartridge-01 (Cepheid) were used to perform automated DNA extraction from whole blood followed by PCR amplification and melt curve analysis to detect SNPs. PCR and melt conditions were optimized using mastermix prepared in house. The NAT2-PGx assay was performed in an 80 ul reaction volume (70 ul mastermix and 10 ul eluted DNA). Briefly, 100 ul of whole blood was mixed with 900 ul of lysis buffer (Cepheid)

in a 1.5 ml Eppendorf tube. The sample was vortexed for 2-3 sec and incubated at room temperature for 2 min. The entire 1 ml whole blood and lysis buffer mix was loaded into sample preparation chamber of flex cart-01 for automated DNA extraction. 70 ul PCR mastermix was simultaneously loaded in the PCR reaction chamber of the flex cart-01. The GeneXpert was programmed to elute DNA in 10 ul volume which was used for the NAT2-PGx assay. PCR mastermix included (2 ul of 2 U Aptataq exo-DNA polymerase, 1× Betaine, 1× PCR additive reagent, 1× Aptataq buffer, 8 mM MgCl2, 400 nM FP, 900 nM reverse primers, 500 nM of 191-Cy5.5 and 857-Alexa-405, 430 nM 282-Alexa-647 and 590-FAM and 300 nM 341-Alexa-537 probes). PCR was initiated at holding stage—50° C. for 2 min, initial denaturation at 94° C. for 2 min, followed by 50 cycles of denaturation at 95° C. for 15 sec, annealing at 57° C. for 30 sec and extension at 65° C. for 60 sec. The melting program included three steps: denaturation at 95° C. for 1 min, followed by renaturation at 40° C. for 3 min and a continuous reading of fluorescence from 40 to 72° C. by heating at increments of 0.05° C./sec. The MMCA curve was analyzed using the GXP version 4.8 software.

Applicant validated the automated NAT2-PGx assay by analyzing 20 blood samples, for which polymorphisms in the 5 positions were confirmed by Sanger sequencing. Applicant assessed analytical sensitivity of the assay and robustness to input blood volume by performing it on varying volumes of whole blood (200 ul, 100 ul, 50 ul, 25 ul) and comparing the Tm results and standard deviation for each position across blood volumes.

EXAMPLE 7 qPCR Run Method and Melt Curve Analysis

Datasets

The datasets used to develop the NAT2 classifier was obtained from the IGSR (International Genome Sample Resource, 1000 genomes project) and a meta-analysis by Sabbagh et. al (E1,E2).

NAT2 Acetylator Phenotype Prediction Classifier

Phased genomes from 8,561 individuals were used and haplotypes were labeled based on 7 polymorphic sites in the NAT2 gene (191G>A, 282C>T, 341T>C, 481C>T, 590G>A, 803A>G and 857G>A), following an international consensus nomenclature. Individuals with two slow haplotypes were considered slow acetylators; those with two rapid haplotypes were considered rapid acetylators; and those with one slow and one rapid acetylator were considered intermediate acetylators. An unphased dataset was constructed containing only information on whether each sample was wild type for both alleles, homozygous variant for both alleles, or heterozygous. Applicant then split the dataset into two-thirds for a training set and one third for an out-of-sample test set, using sampling stratified by geographic representation to ensure representativeness in the training and test sets. Applicant trained a random forest model on the training set using the caret package in R (E3) and assessed classification performance on the test set. Applicant began with a 7 SNP model and eliminated SNPs in sequential models according to the lowest variable importance factor.

Sample Collection

Sputum and plasma samples from 48 newly diagnosed patients with active pulmonary tuberculosis were collected at the Federal University of Grande Dourados, Brazil. All participants were treated with standardized, weight-based doses of isoniazid, rifampicin, pyrazinamide and ethambutol. Plasma samples were collected at 1 hour and 8 hours after the first dose and after 1 hour on day 14. Plasma drug concentrations for isoniazid and acetyl-isoniazid were quantified by high-performance liquid chromatography coupled to tandem mass spectrometry (HPLC-MS) as previously described (E4).

Reference NAT2 SNP Genotyping Assays

Sputum processing, host DNA extraction and single-plex assays on clinical samples: Spontaneously expectorated sputum from confirmed pulmonary tuberculosis patients was collected in approximately 10 mL of guanidine thiocyanate (GTC) solution (5 M guanidinium thiocyanate, 0.5% w/v sodium N-lauryl sarcosine, 25 mM trisodium citrate, 0.1 M 2-mercaptoethanol, 0.5% w/v Tween 80 [pH 7.0]) as described previously (E5). The samples were needle sheared and centrifuged at 3000 rpm for 30 min. The supernatant was removed leaving behind 1 ml pellet. The pellet was centrifuged at 11,500 rpm for 3 min. Approximately 0.5 ml supernatant was transferred to a fresh cryovial and 0.75 ml Trizol LS was added to the supernatant. The samples were frozen at −80 until used. Host DNA was extracted from the supernatant using a manual extraction method described previously (E6). The DNA was eluted in 50 ul DNase-free water and quantified on Qubit. Approximately 10 ng of genomic DNA was used for each single-plex melt curve and commercial TaqMan SNP (NAT2 TaqMan® SNP Genotyping Assays, Applied Biosystems) assay.

DNA extraction from whole blood samples from healthy individuals: For 5-plex assay validation, genomic DNA from 100 ul of whole blood from healthy individuals was extracted using Qiagen Blood and tissue kit (#69504). The DNA was eluted in 30 ul DNase-free water and quantified on Qubit. 100 ng of DNA was used for Sanger sequencing validation.

PCR Amplification for Sanger DNA Sequencing

For DNA sequencing, an 823 bp fragment of the NAT2 gene (819-1641 bp of the gene) was amplified using the forward primer 5'-GGGCTGTTCCCTTTGAGA-3' (SEQ ID NO:15) and reverse primer 5'-TAGTGAGTTGGGTGATAC-3' (SEQ ID NO:16). A 20 µl PCR mixture contained 0.5 µl of each forward and reverse primers from 10 µM stocks, 8 µl double distilled water, 0.5 ul Phusion Taq polymerase and 1 µl (~100 ng) DNA template. PCR was performed with initial denaturation at 95° C. for 5 min followed by 30 cycles of denaturation at 95° C. for 30 s, annealing at 55° C. for 30 s and extension at 72° C. for 1 min, with an additional extension at 72° C. for 10 min. PCR products were analyzed on 1.5% agarose gels to confirm size of product which was then sequenced at the (Stanford PAN Facility, CA).

Primers and Probes for Melt Curve Analysis

Three sets of primers spanning the NAT2 gene were used for single-plex and multiplex PCR. Primers and sloppy molecular beacon (SMB) probes were designed using Beacon Designer (Premier Biosoft International, Palo, CA; version 8). Three of 5 molecular beacon probes (NAT2-191, NAT2-590 and NAT2-857) were designed with 100% complementarity towards mutant alleles and two (NAT2-282 and NAT2-341) were 100% specific to wild type alleles. For single-plex assays, all probes were labelled with FAM at their 5' end and BHQ-1 at 3'. For the multiplex assay on GeneXpert, FAM was replaced with other fluorophores except for NAT2-590. Primers and probes sequences for the multiplex assay with their corresponding fluorophores and quenchers are as described herein.

Single-Plex PCR and Melt Curve Analysis on Pulmonary TB Patients

Genomic DNA extracted from sputum samples from TB positive patients was used for single-plex assays performed on StepOne Plus Real Time PCR. A 20 ul total reaction volume was set up using 10 ng genomic DNA per assay. PCR mastermix included (0.5 ul of 2U Aptataq exo-DNA polymerase, 1× betaine, 1× Aptataq buffer, 4 mM MgCl2, 1× ROX passive reference dye, 60 nM FP, 1000 nM reverse primers, 250 uM of each probe). PCR was initiated by 10 min of denaturation-activation at 95° C., followed by 50 cycles at 95° C. for 15 sec (denaturation), annealing at 60° C. for 15 s and extension at 76° C. for 20 sec. The melting program included three steps: denaturation at 95° C. for 1 min, followed by renaturation at 35° C. for 3 min and a continuous reading of fluorescence from 45 to 85° C. by heating at increments of 0.03° C./s. The MMCA curve was analyzed using the StepOne Plus software version 2.0. For single-plex melt curve assay validation, TaqMan 7-SNP genotyping assays were performed using commercial assays (NAT2 TaqMan® SNP Genotyping Assays, Applied Biosystems) on DNA extracted from sputum samples from 49 pulmonary TB patients on a StepOne Plus Real Time PCR machine.

Pharmacokinetic Analysis of INH Clearance in Tuberculosis Patients

The population PK analysis was performed using the non-linear mixed effects modeling approach using NONMEM (version 7.4.3; ICON plc, Gaithersburg, MD, USA), PsN and R-based Xpose (version 4.7 and higher) (E7,E8). One-compartment model with a first-order absorption with a lognormal distribution for inter-individual variability (IIV) on different PK parameter(s) as well as an additive and/or proportional model for the residual error were tested for the base model selection. Mixture models with two or three subpopulations representing different clearance rate were then evaluated. The first-order conditional estimation with interaction method (FOCEI) was applied and the model-building procedure and model selection was based on the log-likelihood criterion (the difference in the minimum OFV between hierarchical models was assumed to be Chi-square distributed with degrees of freedom equal to the difference in the number of parameters between models), goodness-of-fit plots (e.g. relevant residuals against time randomly distributed around zero), and scientific plausibility of the model. Visual predictive check was conducted to evaluate whether the final model with estimated fixed-effect parameters and covariates adequately describe data.

Automated NAT2-PGx Multiplex PCR and Melt Curve Analysis

Asymmetric PCR and melt curve analysis were performed on a GeneXpert IV instrument using GeneXpert Dx 4.8 software (Cepheid, Sunnyvale). Flex cartridge-01 (Cepheid) were used to perform automated DNA extraction from whole blood followed by PCR amplification and melt curve analysis to detect SNPs. PCR and melt conditions were optimized using mastermix prepared in house. The NAT2-PGx assay was performed in an 80 ul reaction volume (70 ul mastermix and 10 ul eluted DNA). Briefly, 100 ul of whole blood was mixed with 900 ul of lysis buffer (Cepheid) in a 1.5 ml Eppendorf tube. The sample was vortexed for 2-3 sec and incubated at room temperature for 2 min. The entire 1 ml whole blood and lysis buffer mix was loaded into sample preparation chamber of flex cart-01 for automated DNA extraction. 70 ul PCR mastermix was simultaneously loaded in the PCR reaction chamber of the flex cart-01. The GeneXpert was programmed to elute DNA in 10 ul volume which was used for the NAT2-PGx assay. PCR mastermix included (2 ul of 2U Aptataq exo-DNA polymerase, 1× Betaine, 1× PCR additive reagent, 1× Aptataq buffer, 8 mM MgCl2, 400 nM FP, 900 nM reverse primers, 500 nM of 191-Cy5.5 and 857-Alexa-405, 430 nM 282-Alexa-647 and 590-FAM and 300 nM 341-Alexa-537 probes). PCR was initiated at holding stage—50° C. for 2 min, initial denaturation at 94° C. for 2 min, followed by 50 cycles of denaturation at 95° C. for 15 sec, annealing at 57° C. for 30 sec and extension at 65° C. for 60 sec. The melting program included three steps: denaturation at 95° C. for 1 min, followed by renaturation at 40° C. for 3 min and a continuous reading of fluorescence from 40 to 72° C. by heating at increments of 0.05° C./sec. The MMCA curve was analyzed using the GXP version 4.8 software.

The automated NAT2-PGx assay was validated by analyzing 20 blood samples, for which polymorphisms in the 5 positions were confirmed by Sanger sequencing. Applicant assessed analytical sensitivity of the assay and robustness to input blood volume by performing it on varying volumes of whole blood (200 ul, 100 ul, 50 ul, 25 ul) and comparing the Tm results and standard deviation for each position across blood volumes.

TABLE 6

List of primers and probes

| Sequence name | Sequence type | Sequence | SEQ ID NO. |
|---|---|---|---|
| NAT2-Seq1-FP | Primer | CATGGAGTTGGGCTTAGAGG | 1 |
| NAT2-Seq1-RP | Primer | AGCTTCCAGACCCAGCATC | 2 |
| NAT2-Seq2-FP | Primer | GTGCCTTGCATTTTCTGCTT | 3 |
| NAT2-Seq2-RP | Primer | GCAAGGAACAAAATGATGTGG | 4 |
| NAT2-Seq3-FP | Primer | ACTGTTTGGTGGGCTTCATC | 5 |
| NAT2-Seq3-RP | Primer | GAGTTGGGTGATACATACACAAGG | 6 |
| NAT2-191 | Sloppy molecular Beacon probe | 5'-Cy5.5-CGGCGCTGTAAGAAGAAACCAGGGTGGGTGGTGTGCGCCG-3IAbRQSp-3' | 7 |
| NAT2-282 | Sloppy molecular Beacon probe | 5'-Alexa647/CGCAGCGTATTTTTACATCCCTCCAGTTAACAAATACAGCGCTGCG/3IAbRQSp-3' | 8 |
| NAT2-341 | Sloppy molecular Beacon probe | 5'-Alex532N/GGCGAGGGTGACCATTGACGGCAGGAATTACATTGTCTCGCC/3IABkFQ-3' | 9 |
| NAT2-590 | Sloppy molecular Beacon probe | 5'-FAM-GCCGCGCGCTTGAACCTCAAACAATTGAAGATTTTGAGTCGCGGC/3IAbRQSp-3' | 10 |
| NAT2-857 | Sloppy molecular Beacon probe | 5'-Alexa405-CGCGGCCAAACCTGGTGATGAATCCCTTACTATTTAGAAGCCGCG-3IABkFQ-3' | 11 |

TABLE 7

| Primers and probe from MTB detection | | | |
|---|---|---|---|
| Sequence name | | | SEQ ID NO: |
| MTB_1S6110-FP | Primer | GTCGAACGGCTGATGACCA | 12 |
| MTB_1S6110-RP | Primer | AGCGGCGCTGGACGAGAT | 13 |
| MTB_IS6110-Molecular Beacon Probe | Sloppy molecular Beacon probe | **5'-FAM**-CGCAGCGACCACGATCGCTGATCCGGCCACAGGCTGCG-**BHQ1-3'** | 14 |

TABLE 8

| NAT2-PGx multiplex qPCR mastermix composition | | |
|---|---|---|
| 5-plex | Working concentration | Volume (ul) |
| 5× APTAtaq buffer | 1× | 16 |
| Betaine | 1× | 16 |
| Additive reagent (5×) | 1× | 14 |
| 100 mM MgCl2 | 8 mM | 6.5 |
| 25 mM dNTP | 1 mM | 3.5 |
| Seq1-FP 50 uM | 400 nM | 0.7 |
| Seq-1-RP 60 uM | 900 nM | 1.2 |
| Seq2-FP 50 uM | 400 nM | 0.7 |
| Seq-2-RP 60 uM | 900 nM | 1.2 |
| Seq3-FP 50 uM | 400 nM | 0.7 |
| Seq-3-RP 60 uM | 900 nM | 1.2 |
| Probe-191-Cy5.5 (20 uM) | 500 nM | 2 |
| Probe-282-Alexa 647 (20 uM) | 430 nM | 1.75 |
| Probe-341-Alexa-537 (10 uM) | 300 nM | 2.5 |
| Probe-590-FAM (20 uM) | 430 nM | 1.75 |
| Probe-857-Alexa-405 (20 uM) | 500 nM | 2 |
| Aptataq exo polymerase enzyme | 1× | 2 |

TABLE 9

Population information on the dataset used to develop 5-SNP classifier.

| | Intermediate | | Rapid | | Slow | | Total |
|---|---|---|---|---|---|---|---|
| | n | % | n | % | n | % | n |
| Colombians from Medellin, Colombia | 34 | 36% | 11 | 12% | 49 | 52% | 94 |
| Mexican Ancestry from Los Angeles USA | 30 | 47% | 7 | 11% | 27 | 42% | 64 |
| Peruvians from Lima, Peru | 45 | 53% | 17 | 20% | 23 | 27% | 85 |
| Puerto Ricans from Puerto Rico | 37 | 36% | 14 | 13% | 53 | 51% | 104 |
| Embera | 59 | 43% | 57 | 42% | 20 | 15% | 136 |
| Ngawbe | 38 | 36% | 59 | 56% | 8 | 8% | 105 |
| Nicaraguans | 69 | 50% | 29 | 21% | 39 | 28% | 137 |
| US Caucasians | 151 | 39% | 23 | 6% | 213 | 55% | 387 |
| Total | 463 | 42% | 217 | 20% | 432 | 39% | 1112 |
| Bengali from Bangladesh | 35 | 41% | 6 | 7% | 45 | 52% | 86 |
| Gujarati Indian from Houston, Texas | 38 | 37% | 3 | 3% | 62 | 60% | 103 |
| Indian Telugu from the UK | 38 | 37% | 7 | 7% | 57 | 56% | 102 |
| Punjabi from Lahore, Pakistan | 24 | 25% | 4 | 4% | 68 | 71% | 96 |

TABLE 9-continued

Population information on the dataset used to develop 5-SNP classifier.

| | Intermediate | | Rapid | | Slow | | Total |
|---|---|---|---|---|---|---|---|
| | n | % | n | % | n | % | n |
| Sri Lankan Tamil from the UK | 27 | 27% | 9 | 9% | 65 | 64% | 101 |
| Gujarati Indians | 12 | 24% | 2 | 4% | 36 | 72% | 50 |
| Turkish Men | 24 | 48% | 4 | 8% | 22 | 44% | 50 |
| Total | 198 | 34% | 35 | 6% | 355 | 60% | 588 |
| Chinese Dai in Xishuangbanna, China | 35 | 38% | 25 | 27% | 33 | 35% | 93 |
| Han Chinese in Beijing, China | 47 | 46% | 39 | 38% | 17 | 17% | 103 |
| Southern Han Chinese | 48 | 46% | 31 | 30% | 26 | 25% | 105 |
| Japanese in Tokyo, Japan | 40 | 38% | 45 | 43% | 19 | 18% | 104 |
| Kinh in Ho Chi Minh City, Vietnam | 47 | 47% | 17 | 17% | 35 | 35% | 99 |
| Chinese | 23 | 52% | 12 | 27% | 9 | 20% | 44 |
| HanChinese | 61 | 54% | 37 | 33% | 14 | 13% | 112 |
| Japanese | 139 | 44% | 153 | 48% | 24 | 8% | 316 |
| Koreans | 470 | 47% | 434 | 43% | 96 | 10% | 1000 |
| Koreanwomen | 122 | 42% | 121 | 42% | 45 | 16% | 288 |
| Thai | 17 | 39% | 5 | 11% | 22 | 50% | 44 |
| Total | 1049 | 45% | 919 | 40% | 340 | 15% | 2308 |
| Finnish in Finland | 37 | 37% | 6 | 6% | 56 | 57% | 99 |
| British in England and Scotland | 31 | 34% | 6 | 7% | 54 | 59% | 91 |
| Iberian Population in Spain | 37 | 35% | 3 | 3% | 67 | 63% | 107 |
| Toscani in Italia | 37 | 35% | 10 | 9% | 60 | 56% | 107 |
| AshkenaziJews | 7 | 18% | 1 | 3% | 32 | 80% | 40 |
| French | 15 | 25% | 6 | 10% | 39 | 65% | 60 |
| Germans | 392 | 37% | 53 | 5% | 622 | 58% | 1067 |
| Kyrgyz | 132 | 46% | 56 | 19% | 102 | 35% | 290 |
| Polish | 74 | 30% | 18 | 7% | 156 | 63% | 248 |
| Romanians | 52 | 37% | 16 | 11% | 72 | 51% | 140 |
| Russians | 107 | 37% | 15 | 5% | 168 | 58% | 290 |
| Saami | 17 | 35% | 3 | 6% | 28 | 58% | 48 |
| Sardinians | 18 | 37% | 1 | 2% | 30 | 61% | 49 |
| Spanish | 99 | 38% | 20 | 8% | 139 | 54% | 258 |
| Swedes | 11 | 22% | 0 | 0% | 39 | 78% | 50 |
| Turks | 117 | 39% | 12 | 4% | 174 | 57% | 303 |
| UKCaucasians | 30 | 27% | 8 | 7% | 74 | 66% | 112 |
| Utah Residents (CEPH) with Northern and Western European Ancestry | 36 | 36% | 9 | 9% | 54 | 55% | 99 |
| Total | 1249 | 36% | 243 | 7% | 1966 | 57% | 3458 |
| Moroccans | 10 | 23% | 4 | 9% | 30 | 68% | 44 |
| African Caribbeans in Barbados | 46 | 48% | 10 | 10% | 40 | 42% | 96 |
| Americans of African Ancestry in SW USA | 22 | 36% | 6 | 10% | 33 | 54% | 61 |
| Esan in Nigeria | 38 | 38% | 13 | 13% | 48 | 48% | 99 |
| Gambian in Western Divisions in the Gambia | 48 | 42% | 12 | 11% | 53 | 47% | 113 |
| Luhya in Webuye, Kenya | 39 | 39% | 7 | 7% | 53 | 54% | 99 |
| Mende in Sierra Leone | 45 | 53% | 13 | 15% | 27 | 32% | 85 |
| Yoruba in Ibadan, Nigeria | 62 | 57% | 13 | 12% | 33 | 31% | 108 |
| AtekeBantu | 27 | 55% | 0 | 0% | 22 | 45% | 49 |
| BakaPygmies | 18 | 60% | 7 | 23% | 5 | 17% | 30 |
| BakolaPygmies | 11 | 28% | 25 | 63% | 4 | 10% | 40 |
| BlackSouthAfricans | 40 | 40% | 21 | 21% | 40 | 40% | 101 |
| Malians | 15 | 30% | 5 | 10% | 30 | 60% | 50 |

TABLE 9-continued

| Population information on the dataset used to develop 5-SNP classifier. | Intermediate | | Rapid | | Slow | | Total |
|---|---|---|---|---|---|---|---|
| | n | % | n | % | n | % | n |
| Senegalese | 42 | 44% | 8 | 8% | 46 | 48% | 96 |
| Somali | 6 | 25% | 2 | 8% | 16 | 67% | 24 |
| Total | 459 | 44% | 142 | 14% | 450 | 43% | 1051 |

TABLE 10

Whole blood samples (n = 20) analyzed on 5-plex NAT2-PGx assay and validated on Sanger sequencing

| Sample ID | Predicted Phenotype | Genotyping method | 191-MT | 191-WT | 282-MT | 282-WT | 341-MT | 341-WT | 590-MT | 590-WT | 857-MT | 857-WT |
|---|---|---|---|---|---|---|---|---|---|---|---|---|
| SBC-673 | Slow | Sanger | NA | G | NA | C | C | NA | NA | G | NA | 62.8 |
| SBC-673 | Slow | Xpert | NA | 61.8 | NA | 66.93 | 66.6 | NA | NA | 64 | NA | 62.53 |
| SBC-674 | Slow | Sanger | NA | G | T | C | C | T | NA | G | A | G |
| SBC-674 | Slow | Xpert | NA | 61.82 | 62.9 | 66.7 | 66.8 | 68.9 | NA | 63.9 | 66.3 | 62.3 |
| SBC-676 | Rapid | Sanger | NA | G | NA | C | NA | T | NA | G | NA | G |
| SBC-676 | Rapid | Xpert | NA | 61.9 | NA | 66.7 | NA | 68.7 | NA | 64.1 | NA | 62.5 |
| SBC-677 | Intermediate | Sanger | NA | G | NA | C | C | T | NA | G | NA | G |
| SBC-677 | Intermediate | Xpert | NA | 61.9 | NA | 66.6 | 66.7 | 68.8 | NA | 63.9 | NA | 62.2 |
| SBC-678 | Slow | Sanger | NA | G | T | NA | NA | T | A | NA | NA | G |
| SBC-678 | Slow | Xpert | NA | 62.4 | 63.4 | NA | NA | 69.2 | 68.7 | NA | NA | 63.1 |
| SBC-685 | Intermediate | Sanger | NA | G | T | C | NA | T | A | G | NA | G |
| SBC-685 | Intermediate | Xpert | NA | 62.1 | 63.3 | 66.8 | NA | 68.9 | 68.5 | 64.3 | NA | 62.8 |
| SBC-686 | Intermediate | Sanger | NA | G | NA | C | C | T | NA | G | NA | G |
| SBC-686 | Intermediate | Xpert | NA | 62.6 | NA | 67.1 | 66.6 | 68.7 | NA | 64.5 | NA | 63.1 |
| SBC-687 | Intermediate | Sanger | NA | G | NA | C | C | T | NA | G | NA | G |
| SBC-687 | Intermediate | Xpert | NA | 62.2 | NA | 66.8 | 66.6 | 68.8 | NA | 64.3 | NA | 62.8 |
| SBC-688 | Slow | Sanger | NA | G | T | NA | NA | T | A | NA | NA | G |
| SBC-688 | Slow | Xpert | NA | 62.1 | 62.6 | NA | NA | 68.6 | 68.1 | NA | NA | 62.8 |
| SBC-690 | Intermediate | Sanger | NA | G | T | C | NA | T | A | G | NA | G |
| SBC-690 | Intermediate | Xpert | NA | 62 | 63.1 | 66.6 | NA | 68.7 | 68.4 | 64.3 | NA | 62.76 |
| SBC-693 | Slow | Sanger | NA | G | T | NA | NA | T | A | G | A | G |
| SBC-693 | Slow | Xpert | NA | 62.2 | 62.7 | NA | NA | 68.8 | 68.4 | 64.2 | 66.3 | 62.8 |
| SBC-695 | Intermediate | Sanger | NA | G | NA | C | C | T | NA | G | NA | G |
| SBC-695 | Intermediate | Xpert | NA | 62.3 | NA | 67.1 | 66.9 | 69.4 | NA | 64.5 | NA | 63 |
| SBC-696 | Slow | Sanger | NA | G | T | C | C | T | A | G | NA | G |
| SBC-696 | Slow | Xpert | NA | 61.8 | 62.9 | 66.7 | 66.6 | 69 | 68.2 | 64.1 | NA | 62.5 |
| SBC-697 | Intermediate | Sanger | NA | G | T | C | NA | T | NA | G | A | G |
| SBC-697 | Intermediate | Xpert | NA | 62.5 | 63.2 | 67.2 | NA | 69.2 | NA | 64.5 | 67.7 | 62.9 |
| SBC-699 | Intermediate | Sanger | NA | G | NA | C | C | T | NA | G | NA | G |
| SBC-699 | Intermediate | Xpert | NA | 62.2 | NA | 66.9 | 66.3 | 68.9 | NA | 64.5 | NA | 62.8 |
| SBC-700 | Slow | Sanger | NA | G | T | NA | NA | T | A | G | A | G |
| SBC-700 | Slow | Xpert | NA | 61.9 | 63 | NA | NA | 68.6 | 68.6 | 64.5 | 66.5 | 62.8 |
| SBC-702 | Rapid | Sanger | NA | G | NA | C | NA | T | A | G | NA | G |
| SBC-702 | Rapid | Xpert | NA | 61.9 | NA | 66.5 | NA | 68.2 | 68 | 63.8 | NA | 62.7 |
| SBC-703 | Intermediate | Sanger | NA | G | T | C | NA | T | A | G | NA | G |
| SBC-703 | Intermediate | Xpert | NA | 62.3 | 63.3 | 67.2 | NA | 69.1 | 68.7 | 64.7 | NA | 62.9 |
| SBC-704 | Intermediate | Sanger | NA | G | NA | C | C | T | NA | G | NA | G |
| SBC-704 | Intermediate | Xpert | NA | 62 | NA | 67.3 | 65.9 | 68.9 | NA | 64.9 | NA | 63 |
| SBC-714 | Slow | Sanger | NA | G | NA | C | C | NA | NA | G | NA | G |
| SBC-714 | Slow | Xpert | NA | 62.7 | NA | 67.6 | 66.5 | NA | NA | 64.9 | NA | 63.1 |

TABLE 11

NAT2 polymorphism detection at various sample volumes.

| Sample ID | Predicted Phenotype | Genotyping method | 191-MT | 191-WT | 282-MT | 282-WT | 341-MT | 341-WT | 590-MT | 590-WT | 857-MT | 857-WT |
|---|---|---|---|---|---|---|---|---|---|---|---|---|
| SBC-673 | Slow | 100 ul | NA | 61.8 | NA | 66.7 | 66.3 | NA | NA | 64.3 | NA | 62.8 |
| SBC-678 | Slow | 100 ul | NA | 62.2 | 62.9 | NA | NA | 69 | 68.4 | NA | NA | 62.9 |
| SBC-685 | Intermediate | 100 ul | NA | 62.1 | 63.3 | 66.8 | NA | 68.9 | 68.5 | 64.3 | NA | 62.8 |
| SBC-696 | Slow | 100 ul | NA | 61.8 | 62.9 | 66.7 | 66.6 | 69 | 68.2 | 64.1 | NA | 62.5 |
| SBC-697 | Intermediate | 100 ul | NA | 62.5 | 63.2 | 67.2 | NA | 69.2 | NA | 64.5 | 67.7 | 62.9 |
| SBC-699 | Intermediate | 100 ul | NA | 62.2 | NA | 66.9 | 66.3 | 68.9 | NA | 64.5 | NA | 62.8 |

TABLE 11-continued

NAT2 polymorphism detection at various sample volumes.

| Sample ID | Predicted Phenotype | Genotyping method | 191-MT | 191-WT | 282-MT | 282-WT | 341-MT | 341-WT | 590-MT | 590-WT | 857-MT | 857-WT |
|---|---|---|---|---|---|---|---|---|---|---|---|---|
| SBC-702 | Rapid | 100 ul | NA | 61.7 | NA | 66.5 | NA | 68.3 | 68.6 | 63.8 | NA | 62.5 |
| SBC-703 | Rapid | 100 ul | NA | 62.3 | 63.3 | 67.2 | NA | 69.1 | 68.7 | 64.7 | NA | 62.9 |
| SBC-704 | Intermediate | 100 ul | NA | 62 | NA | 66.9 | 65.7 | 68.8 | NA | 64.4 | NA | 62.9 |
| SBC-VT | Slow | 100 ul | NA | 61.8 | 63.1 | 66.4 | 65.9 | 68.9 | 67.9 | 64.4 | NA | 62.9 |
| SBC-673 | Slow | 200 ul | NA | 61.8 | NA | 66.93 | 66.6 | NA | NA | 64 | NA | 62.53 |
| SBC-678 | Slow | 200 ul | NA | 62.4 | 63.4 | NA | NA | 69.2 | 68.7 | NA | NA | 63.1 |
| SBC-685 | Intermediate | 200 ul | NA | 62 | 63.2 | 66.68 | NA | 68.8 | 68.5 | 64.4 | NA | 62.9 |
| SBC-696 | Slow | 200 ul | NA | 62.1 | 63.1 | 67 | 65.9 | 68.1 | 68.5 | 64.2 | NA | 62.7 |
| SBC-697 | Intermediate | 200 ul | NA | 62.2 | 63.5 | 67.1 | NA | 68.9 | NA | 64.3 | 66.9 | 62.9 |
| SBC-699 | Intermediate | 200 ul | NA | 61.9 | NA | 66.2 | 65.8 | 68.9 | NA | 64.1 | NA | 62.8 |
| SBC-702 | Rapid | 200 ul | NA | 61.9 | NA | 66.5 | NA | 68.2 | NA | 63.8 | NA | 62.7 |
| SBC-703 | Intermediate | 200 ul | NA | 62.1 | 63.4 | 67.2 | NA | 68.8 | 68.7 | 64.3 | NA | 63 |
| SBC-704 | Intermediate | 200 ul | NA | 62 | NA | 67.3 | 65.9 | 68.9 | NA | 64.9 | NA | 63 |
| SBC-VT | Slow | 200 ul | NA | 61.9 | 63 | 67.2 | 65.7 | 68.9 | 68.8 | 65.2 | NA | 62.9 |
| SBC-673 | Slow | 25 ul | NA | 62.5 | NA | 67.5 | 66.3 | NA | NA | 64.9 | NA | 62.4 |
| SBC-678 | Slow | 25 ul | NA | 61.9 | 62.6 | NA | NA | 68.7 | 68.2 | NA | NA | 62.5 |
| SBC-685 | Intermediate | 25 ul | NA | 61.9 | 63 | 66.6 | NA | 68.6 | 68.4 | 64.5 | NA | 61.9 |
| SBC-696 | Slow | 25 ul | NA | 61.8 | 63 | 66.5 | 66.2 | 68.2 | 68.2 | 64.2 | NA | 62.7 |
| SBC-697 | Intermediate | 25 ul | NA | 61.08 | 62.1 | 66.3 | NA | 67.9 | NA | 63.5 | 66.7 | 62.1 |
| SBC-699 | Intermediate | 25 ul | NA | 62 | NA | 66.5 | 65.7 | 68.9 | NA | 64.2 | NA | 62.5 |
| SBC-702 | Rapid | 25 ul | NA | 61.9 | NA | 66.3 | NA | 68.2 | NA | 63.8 | NA | 62.9 |
| SBC-703 | Intermediate | 25 ul | NA | 62.1 | 63.2 | 67.2 | NA | 68.7 | 68.8 | 64.7 | NA | 62.8 |
| SBC-704 | Intermediate | 25 ul | NA | 62.2 | NA | 67.3 | 66.1 | 68.7 | NA | 64.7 | NA | 63.1 |
| SBC-VT | Slow | 25 ul | NA | 62 | 63.2 | 67.3 | 65.6 | 69 | 69 | 65.3 | NA | 62.9 |
| SBC-673 | Slow | 50 ul | NA | 62.5 | NA | 67.4 | 66.5 | NA | NA | 64.9 | NA | 61.9 |
| SBC-678 | Slow | 50 ul | NA | 62.1 | 62.8 | NA | NA | 68.8 | 68.3 | NA | NA | 62.1 |
| SBC-685 | Intermediate | 50 ul | NA | 62 | 63.1 | 66.6 | NA | 68.6 | 68.5 | 64.4 | NA | 62.8 |
| SBC-696 | Slow | 50 ul | NA | 62 | 64.9 | 66.8 | 65.6 | 68.1 | 68.5 | 64.3 | NA | 62.5 |
| SBC-697 | Intermediate | 50 ul | NA | 61.9 | 62.9 | 67.6 | NA | 68.2 | NA | 63.9 | 66.6 | 62.8 |
| SBC-699 | Intermediate | 50 ul | NA | 62.05 | NA | 66.25 | 65.8 | 68.5 | NA | 64.15 | NA | 62.9 |
| SBC-702 | Rapid | 50 ul | NA | 61.5 | NA | 66.2 | NA | 68.5 | NA | 64.4 | NA | 62.8 |
| SBC-703 | Intermediate | 50 ul | NA | 62 | 62.9 | 66.3 | NA | 68.6 | 68.4 | 64.4 | NA | 62.9 |
| SBC-704 | Intermediate | 50 ul | NA | 62.1 | NA | 66.8 | 66 | 68.7 | NA | 64.4 | NA | 63.1 |
| SBC-VT | Slow | 50 ul | NA | 62.1 | 63.2 | 67.3 | 65.8 | 68.8 | 68.7 | 64.8 | NA | 62.9 |
| SBC-673 | Slow | Sanger | NA | G | NA | C | C | NA | NA | G | NA | 62.8 |
| SBC-678 | Slow | Sanger | NA | G | T | NA | NA | T | A | NA | NA | G |
| SBC-685 | Intermediate | Sanger | NA | G | T | C | NA | T | A | G | NA | G |
| SBC-696 | Slow | Sanger | NA | G | T | C | C | T | A | G | NA | G |
| SBC-697 | Intermediate | Sanger | NA | G | T | C | NA | T | NA | G | A | G |
| SBC-699 | Intermediate | Sanger | NA | G | NA | C | C | T | NA | G | NA | G |
| SBC-702 | Rapid | Sanger | NA | G | NA | C | NA | T | A | G | NA | G |
| SBC-703 | Intermediate | Sanger | NA | G | T | C | NA | T | A | G | NA | G |
| SBC-704 | Intermediate | Sanger | NA | G | NA | C | C | T | NA | G | NA | G |
| SBC-VT | Slow | Sanger | NA | G | T | C | C | T | A | G | NA | G |

REFERENCES

1. Gillespie S H, Crook A M, McHugh T D, Mendel C M, Meredith S K, Murray S R, Pappas F, Phillips P P, Nunn A J; REMoxTB Consortium. Four-month moxifloxacin-based regimens for drug-sensitive tuberculosis. N Engl J Med. 2014 Oct. 23; 371(17):1577-87. doi: 10.1056/NEJMoa1407426. Epub 2014 Sep. 7.
2. Merle C S, Fielding K, Sow O B, Gninafon M, Lo M B, Mthiyane T, Odhiambo J, Amukoye E, Bah B, Kassa F, N'Diaye A, Rustomjee R, de Jong B C, Horton J, Perronne C, Sismanidis C, Lapujade O, Illiaro P L, Lienhardt C; OFLOTUB/Gatifloxacin for Tuberculosis Project. A four-month gatifloxacin-containing regimen for treating tuberculosis. N Engl J Med. 2014 Oct. 23; 371(17):1588-98. doi: 10.1056/NEJMoa1315817. Erratum in: N Engl J Med. 2015 Apr. 23; 372(17):1677.
3. Jindani A, Harrison T S, Nunn A J, Phillips P P, Churchyard G J, Charalambous S, Hatherill M, Geldenhuys H, McIlleron H M, Zvada S P, Mungofa S, Shah N A, Zizhou S, Magweta L, Shepherd J, Nyirenda S, van Dijk J H, Clouting H E, Coleman D, Bateson A L, McHugh T D, Butcher P D, Mitchison D A; RIFAQUIN Trial Team. High-dose rifapentine with moxifloxacin for pulmonary tuberculosis. N Engl J Med. 2014 Oct. 23; 371(17):1599-608.
4. Pratt V M, Everts R E, Aggarwal P, Beyer B N, Broeckel U, Epstein-Baak R, Hujsak P, Kornreich R, Liao J, Lorier R, Scott S A, Smith C H, Toji L H, Turner A, Kalman L V. Characterization of 137 Genomic DNA Reference Materials for 28 Pharmacogenetic Genes: A GeT-RM Collaborative Project. J Mol Diagn. 2016 January; 18(1): 109-23.
5. Garcia-Martin E. Interethnic and intraethnic variability of NAT2 single nucleotide polymorphisms. Curr Drug Metab. 2008 July; 9(6):487-97.
6. Schaberg T, Rebhan K, Lode H. Risk factors for side-effects of isoniazid, rifampin and pyrazinamide in patients hospitalized for pulmonary tuberculosis. Eur Respir J. 1996 October; 9(10):2026-30.
7. Saukkonen J J, Cohn D L, Jasmer R M, Schenker S, Jereb J A, Nolan C M, Peloquin C A, Gordin F M, Nunes D, Strader D B, Bernardo J, Venkataramanan R, Sterling T R; ATS (American Thoracic Society) Hepatotoxicity of Antituberculosis Therapy Subcommittee. An official ATS statement: hepatotoxicity of antituberculosis therapy. Am J Respir Crit Care Med. 2006 Oct. 15; 174(8):935-52.

8. Schutz C, Ismail Z, Proxenos C J, Marais S, Burton R, Kenyon C, Maartens G, Wilkinson R J, Meintjes G. Burden of antituberculosis and antiretroviral drug-induced liver injury at a secondary hospital in South Africa. S Afr Med J. 2012 Mar. 2; 102(6):506-11.
9. Lutze H, Johnson D F, Dickman K, Mayanja-Kizza H, Okwera A, Eisenach K, Cave M D, Whalen C C, Johnson J L, Boom W H, Joloba M; Tuberculosis Research Unit. Relapse more common than reinfection in recurrent tuberculosis 1-2 years post treatment in urban Uganda. Int J Tuberc Lung Dis. 2013 March; 17(3):361-7.
10. Romanowski K, Balshaw R F, Benedetti A, Campbell J R, Menzies D, Ahmad Khan F, Johnston J C. Predicting tuberculosis relapse in patients treated with the standard 6-month regimen: an individual patient data meta-analysis. Thorax. 2019 March; 74(3):291-297.
11. Pasipanodya J G, Srivastava S, Gumbo T. Meta-analysis of clinical studies supports the pharmacokinetic variability hypothesis for acquired drug resistance and failure of antituberculosis therapy. Clin Infect Dis. 2012 July; 55(2): 169-77.
12. Gumbo T, Louie A, Liu W, Brown D, Ambrose P G, Bhavnani S M, Drusano G L. Isoniazid bactericidal activity and resistance emergence: integrating pharmacodynamics and pharmacogenomics to predict efficacy in different ethnic populations. Antimicrob Agents Chemother. 2007 July; 51(7):2329-36.
13. Pasipanodya J G, McIlleron H, Burger A, Wash P A, Smith P, Gumbo T. Serum drug concentrations predictive of pulmonary tuberculosis outcomes. J Infect Dis. 2013 Nov. 1; 208(9): 1464-73.
14. Hall R G, Leff R D, Gumbo T. Treatment of active pulmonary tuberculosis in adults: current standards and recent advances. Insights from the Society of Infectious Diseases Pharmacists. Pharmacotherapy. 2009 December; 29(12):1468-81
15. Sterling T R, Njie G, Zenner D, et al. Guidelines for the Treatment of Latent Tuberculosis Infection: Recommendations from the National Tuberculosis Controllers Association and CDC, 2020. MMWR Recomm Rep 2020; 69(No. RR-1):1-11.
16. Kinzig-Schippers M, Tomalik-Scharte D, Jetter A, Scheidel B, Jakob V, Rodamer M, Cascorbi I, Doroshyenko O, Sörgel F, Fuhr U. Should we use N-acetyltransferase type 2 genotyping to personalize isoniazid doses? Antimicrob Agents Chemother. 2005 May; 49(5):1733-8.
17. Du H, Chen X, Fang Y, Yan O, Xu H, Li L, Li W, Huang W. Slow N-acetyltransferase 2 genotype contributes to anti-tuberculosis drug-induced hepatotoxicity: a meta-analysis. Mol Biol Rep. 2013 May; 40
18. Sabbagh A, Langaney A, Darlu P, Gérard N, Krishnamoorthy R, Poloni E S. Worldwide distribution of NAT2 diversity: implications for NAT2 evolutionary history. BMC Genet. 2008 Feb. 27; 9:21.
19. Wang P Y, Xie S Y, Hao Q, Zhang C, Jiang B F. NAT2 polymorphisms and susceptibility to anti-tuberculosis drug-induced liver injury: a meta-analysis. Int J Tuberc Lung Dis. 2012 May; 16(5):589-95.
20. Parkin D P, Vandenplas S, Botha F J, Vandenplas M L, Seifart H I, van Helden P D, van der Walt B J, Donald P R, van Jaarsveld P P. Trimodality of isoniazid elimination: phenotype and genotype in patients with tuberculosis. Am J Respir Crit Care Med. 1997 May; 155(5):1717-22.
21. Gross M, Kruisselbrink T, Anderson K, Lang N, McGovern P, Delongchamp R, Kadlubar F. Distribution and concordance of N-acetyltransferase genotype and phenotype in an American population. Cancer Epidemiol Biomarkers Prey. 1999 August; 8(8):683-92.
22. Mrozikiewicz P M, Cascorbi I, Brockmoller J, Roots I. Determination and allelic allocation of seven nucleotide transitions within the arylamine N-acetyltransferase gene in the Polish population. Clin Pharmacol Ther. 1996 April; 59(4):376-82.
23. Hein D W, Doll M A. Accuracy of various human NAT2 SNP genotyping panels to infer rapid, intermediate and slow acetylator phenotypes. Pharmacogenomics. 2012 January; 13(1):31-41.
24. Snider D E Jr, Caras G J. Isoniazid-associated hepatitis deaths: a review of available information. Am Rev Respir Dis. 1992 February; 145(2 Pt 1):494-7.
25. Azuma J, Ohno M, Kubota R, Yokota S, Nagai T, Tsuyuguchi K, Okuda Y, Takashima T, Kamimura S, Fujio Y, Kawase I; Pharmacogenetics-based tuberculosis therapy research group. NAT2 genotype guided regimen reduces isoniazid-induced liver injury and early treatment failure in the 6-month four-drug standard treatment of tuberculosis: a randomized controlled trial for pharmacogenetics-based therapy. Eur J Clin Pharmacol. 2013 May; 69(5):1091-101.
26. McInnes G and Russ A. Drug Response Pharmacogenetics for 200,000 UK Biobank Participants.
27. Database of arylamine N-acetyltransferases (http://nat.mbg.duth.gr)
28. Prideaux B, Via L E, Zimmerman M D, Eum S, Sarathy J, O'Brien P, Chen C, Kaya F, Weiner D M, Chen P Y, Song T, Lee M, Shim T S, Cho J S, Kim W, Cho S N, Olivier K N, Barry C E 3rd, Dartois V. The association between sterilizing activity and drug distribution into tuberculosis lesions. Nat Med. 2015 October; 21(10): 1223-7.
29. Beal S L. Et al. NONMEM 7.4 Users Guides. (1989-2019). ICON plc, Gaithersburg, MD. https://nonmem.iconplc.com/nonmem744
30. Lindbom L, Ribbing J, Jonsson E N. Perl-speaks-NONMEM (PsN)—a Perl module for NONMEM related programming. Comput Methods Programs Biomed. 2004 August; 75(2):85-94.
31. Chomczynski P. A reagent for the single-step simultaneous isolation of RNA, DNA and proteins from cell and tissue samples. Biotechniques. 1993 September; 15(3): 532-4, 536-7. PMID: 7692896.
32. Kuznetsov I B, McDuffie M, Moslehi R. A web server for inferring the human N-acetyltransferase-2 (NAT2) enzymatic phenotype from NAT2 genotype. Bioinformatics. 2009 May 1; 25(9): 1185-6.
33. Sabbagh A, Darlu P, Vidaud M. Evaluating NAT2PRED for inferring the individual acetylation status from unphased genotype data. BMC Med Genet. 2009 Dec. 31; 10:148.
34. Ramachandran G, Swaminathan S. Role of pharmacogenomics in the treatment of tuberculosis: a review. Pharmgenomics Pers Med. 2012; 5:89-98
35. Rens N E, Uyl-de Groot C A, Goldhaber-Fiebert J D, Croda J, Andrews J R. Cost-effectiveness of a Pharmacogenomic Test for Stratified Isoniazid Dosing in Treatment of Active Tuberculosis. Clin Infect Dis. 2020 Dec. 15; 71(12):3136-3143.
36. Sabbagh A, Darlu P, Crouau-Roy B, Poloni E S. Arylamine N-acetyltransferase 2 (NAT2) genetic diversity and traditional subsistence: a worldwide population survey. PLoS One. 2011 Apr. 6; 6(4):e18507.
37. Mthiyane T, Millard J, Adamson J, Balakrishna Y, Connolly C, Owen A, Rustomjee R, Dheda K, McIlleron H, Pym A S. N-Acetyltransferase 2 Genotypes among Zulu-Speaking South Africans and Isoniazid and N-Acetyl-Isoniazid Pharmacokinetics during Antituberculosis Treatment. Antimicrob Agents Chemother. 2020 Mar. 24; 64(4):e02376-19.

38. van Oosterhout J J, Dzinjalamala F K, Dimba A, Waterhouse D, Davies G, Zijlstra E E, Molyneux M E, Molyneux E M, Ward S. Pharmacokinetics of Antituberculosis Drugs in HIV-Positive and HIV-Negative Adults in Malawi. Antimicrob Agents Chemother. 2015 October; 59(10):6175-80.

39. Wilkins J J, Langdon G, McIlleron H, Pillai G, Smith P J, Simonsson U S. Variability in the population pharmacokinetics of isoniazid in South African tuberculosis patients. Br J Clin Pharmacol. 2011 July; 72(1):51-62.

40. Iselius L, Evans D A. Formal genetics of isoniazid metabolism in man. Clin Pharmacokinet. 1983 November-December; 8(6):541-4.

41. Evans D A. Genetic variations in the acetylation of isoniazid and other drugs. Ann NY Acad Sci. 1968 Jul. 31; 151(2):723-33.

42. Evans D A. An improved and simplified method of detecting the acetylator phenotype. J Med Genet. 1969 December; 6(4):405-7.

43. Naidoo A, Chirehwa M, Ramsuran V, McIlleron H, Naidoo K, Yende-Zuma N, Singh R, Ncgapu S, Adamson J, Govender K, Denti P, Padayatchi N. Effects of genetic variability on rifampicin and isoniazid pharmacokinetics in South African patients with recurrent tuberculosis. Pharmacogenomics. 2019 March; 20(4):225-240.

44. Wilkins J J, Langdon G, McIlleron H, Pillai G C, Smith P J, Simonsson U S. Variability in the population pharmacokinetics of pyrazinamide in South African tuberculosis patients. Eur J Clin Pharmacol. 2006 September; 62(9):727-35.

45. Lee S W, Chung L S, Huang H H, Chuang T Y, Liou Y H, Wu L S. NAT2 and CYP2E1 polymorphisms and susceptibility to first-line anti-tuberculosis drug-induced hepatitis. Int J Tuberc Lung Dis. 2010 May; 14(5):622-6.

46. Roy B, Ghosh S K, Sutradhar D, Sikdar N, Mazumder S, Barman S. Predisposition of antituberculosis drug induced hepatotoxicity by cytochrome P450 2E1 genotype and haplotype in pediatric patients. J Gastroenterol Hepatol. 2006 April; 21(4):784-6.

47. Simon T, Becquemont L, Mary-Krause M, de Waziers I, Beaune P, Funck-Brentano C, Jaillon P. Combined glutathione-S-transferase M1 and T1 genetic polymorphism and tacrine hepatotoxicity. Clin Pharmacol Ther. 2000 April; 67(4):432-7.

48. Strange R C, Jones P W, Fryer A A. Glutathione S-transferase: genetics and role in toxicology. Toxicol Lett. 2000 Mar. 15; 112-113:357-63.

49. Mukonzo J K, Kengo A, Kutesa B, Nanzigu S, Pohanka A, McHugh T D, Zumla A, Aklillu E. Role of pharmacogenetics in rifampicin pharmacokinetics and the potential effect on TB-rifampicin sensitivity among Ugandan patients. Trans R Soc Trop Med Hyg. 2020 Feb. 7; 114(2):107-114.

50. Haley C A. Treatment of Latent Tuberculosis Infection. Microbiol Spectr. 2017 April; 5(2).

EXAMPLE 7

References

E1. Pratt V M, Everts R E, Aggarwal P, Beyer B N, Broeckel U, Epstein-Baak R, Hujsak P, Kornreich R, Liao J, Lorier R, Scott S A, Smith C H, Toji L H, Turner A, Kalman L V. Characterization of 137 Genomic DNA Reference Materials for 28 Pharmacogenetic Genes: A GeT-RM Collaborative Project. J Mol Diagn. 2016 January; 18(1): 109-23.

E2. Sabbagh A, Darlu P, Crouau-Roy B, Poloni E S. Arylamine N-acetyltransferase 2 (NAT2) genetic diversity and traditional subsistence: a worldwide population survey. PLoS One. 2011 Apr. 6; 6(4):e18507.

E3. Kuhn M. et al. (2019). caret: Classification and Regression Training. R package version 6.0-84. https://CRAN.R-project.org/package=caret E4. Prideaux B, Via L E, Zimmerman M D, Eum S, Sarathy J, O'Brien P, Chen C, Kaya F, Weiner D M, Chen P Y, Song T, Lee M, Shim T S, Cho J S, Kim W, Cho S N, Olivier K N, Barry C E 3rd, Dartois V. The association between sterilizing activity and drug distribution into tuberculosis lesions. Nat Med. 2015 October; 21(10): 1223-7.

E5. Walter N D, Dolganov G M, Garcia B J, Worodria W, Andama A, Musisi E, Ayakaka I, Van T T, Voskuil M I, de Jong B C, Davidson R M, Fingerlin T E, Kechris K, Palmer C, Nahid P, Daley C L, Geraci M, Huang L, Cattamanchi A, Strong M, Schoolnik G K, Davis J L. Transcriptional Adaptation of Drug-tolerant *Mycobacterium tuberculosis* During Treatment of Human Tuberculosis. J Infect Dis. 2015 Sep. 15; 212(6):990-8.

E6. Chomczynski P. A reagent for the single-step simultaneous isolation of RNA, DNA and proteins from cell and tissue samples. Biotechniques. 1993 September; 15(3): 532-4, 536-7. PMID: 7692896.

E7. Beal S L. Et al. NONMEM 7.4 Users Guides. (1989-2019). ICON plc, Gaithersburg, MD. https://nonmem.iconplc.com/nonmem744

E8. Lindbom L, Ribbing J, Jonsson E N. Perl-speaks-NONMEM (PsN)—a Perl module for NONMEM related programming. Comput Methods Programs Biomed. 2004 August; 75(2):85-94.

```
INFORMAL SEQUENCE LISTING
(NAT2-FP1)
                                        SEQ ID NO: 1
CATGGAGTTGGGCTTAGAGG

(NAT2-RP1)
                                        SEQ ID NO: 2
AGCTTCCAGACCCAGCATC

(NAT2-FP2)
                                        SEQ ID NO: 3
GTGCCTTGCATTTTCTGCTT

(NAT2-RP2)
                                        SEQ ID NO: 4
GCAAGGAACAAAATGATGTGG

(NAT2-FP3)
                                        SEQ ID NO: 5
ACTGTTTGGTGGGCTTCATC

(NAT2-RP3)
                                        SEQ ID NO: 6
GAGTTGGGTGATACATACACAAGG

(NAT2-191G > A)
                                        SEQ ID NO: 7
CGGCGCTGTAAGAAGAAACCAGGGTGGGTGGTGTGCGCCG
```

-continued (NAT2-282C > T)

SEQ ID NO: 8

CGCAGCGTATTTTTACATCCCTCCA

GTTAACAAATACAGCGCTGCG (NAT2-341T > C)

SEQ ID NO: 9

GGCGAGGGTGACCATTGACGGCAGGAATTACATTGTCTCGCC (NAT2-590A > G)

SEQ ID NO: 10

GCCGCGCGCTTGAACCTCAAACAATTGAAGATTTTGAGTCGCGGC (NAT2-857G > A)

SEQ ID NO: 11

CGCGGCCAAACCTGGTGATGAATCCCTTACTATTTAGAAGCCGCG (MTB_IS6110-FP Primer)

SEQ ID NO: 12

GTCGAACGGCTGATGACCA (MTB_IS6110-RP)

SEQ ID NO: 13

AGCGGCGCTGGACGAGAT (MTB_IS6110-Molecular Beacon_Probe)

SEQ ID NO: 14

CGCAGCGACCACGATCGCTGATCCGGCCACAGGCTGCG

SEQ ID NO: 15

GGGCTGTTCCCTTTGAGA

SEQ ID NO: 16

TAGTGAGTTGGGTGATAC

P Embodiments

P Embodiment 1. A method for detecting single polypeptide polymorphisms in a sample from a subject having or suspected of having tuberculosis, the method comprising: detecting a G191A NAT2 SNP, a C282T NAT2 SNP, a T341C NAT2 SNP, a G590A NAT2 SNP and a G857A NAT2 SNP in a sample from said subject.

P Embodiment 2. The method of P embodiment 1, wherein said detecting comprises PCR assay detection.

P Embodiment 3. The method of P embodiment 1, wherein said detecting comprises quantitating a level of said G191A NAT2 SNP, said C282T NAT2 SNP, said T341C NAT2 SNP, said G590A NAT2 SNP and said G857A NAT2 SNP.

P Embodiment 4. The method of one of P embodiments 1 to 3, wherein based detecting of said G191A NAT2 SNP, said C282T NAT2 SNP, said T341C NAT2 SNP, said G590A NAT2 SNP and said G857A NAT2 SNP, a dose of isoniazid is determined for treating said subject for tuberculosis.

P Embodiment 5. The method of one of P embodiments 1 to 4, wherein said sample is sputum, blood or an oral swab.

P Embodiment 6. The method of one of P embodiments 1 to 5, wherein said subject is being treated with isoniazid.

Embodiments

Embodiment 1. A method of detecting single nucleotide polymorphisms in a subject, the method comprising: detecting G191A NAT2 SNP, C282T NAT2 SNP, T341C NAT2 SNP, G590A NAT2 SNP and G857A NAT2 SNP in a biological sample from said subject, wherein the subject is taking an arylamine drug or a hydrazine drug or the subject is in need of an arylamine drug or a hydrazine drug.

Embodiment 2. The method of embodiment 1, wherein said method does not comprise detecting an additional NAT2 SNP in said biological sample.

Embodiment 3. The method of embodiment 1 or 2, wherein said detecting said G191A NAT2 SNP comprises determining whether said G191A NAT2 SNP is not present, present once or present more than once within the chromosomes of said subject.

Embodiment 4. The method of any of embodiments 1 to 3, wherein said detecting said C282T NAT2 SNP comprises determining whether said C282T NAT2 SNP is not present, present once or present more than once within the chromosomes of said subject.

Embodiment 5. The method of any of embodiments 1 to 4, wherein said detecting said T341C NAT2 SNP comprises determining whether said T341C NAT2 SNP is not present, present once or present more than once within the chromosomes of said subject.

Embodiment 6. The method of any of embodiments 1 to 5, wherein said detecting said G590A NAT2 SNP comprises determining whether said G590A NAT2 SNP is not present, present once or present more than once within the chromosomes of said subject.

Embodiment 7. The method of any of embodiments 1 to 6, wherein said detecting said G857A NAT2 SNP comprises determining whether said G857A NAT2 SNP is not present, present once or present more than once within the chromosomes of said subject.

Embodiment 8. The method of embodiment 1, wherein the method does not comprise detecting any additional NAT2 SNP.

Embodiment 9. The method of embodiment 1, wherein said detecting comprises melt curve analysis, 5' exonuclease polymerase chain reaction, DNA sequencing, restriction fragment length polymorphism, chip hybridization or single base extension assay.

Embodiment 10. The method of embodiment 1, wherein said biological sample is a sputum sample, a saliva sample, a blood sample or a buccal sample.

Embodiment 11. The method of any of embodiments 1 to 10, wherein said subject has a tuberculosis infection.

Embodiment 12. The method of embodiment 11, wherein the tuberculosis infection is latent.

Embodiment 13. The method of any of embodiments 1 to 10, wherein said method further comprises administering an arylamine drug or a hydrazine drug at a dose greater than the prescribed dose where a G191A NAT2 SNP, C282T NAT2 SNP, T341C NAT2 SNP, G590A NAT2 SNP and G857A NAT2 SNP are not detected in said biological sample.

Embodiment 14. The method of any of embodiments 1 to 10, wherein said method further comprises administering an arylamine drug or a hydrazine drug at a dose less than the prescribed dose wherein: (a) two occurrences of G191A NAT2 SNP is detected, two occurrences of C282T NAT2 SNP is detected, two occurrences of T341C NAT2 SNP is detected, two occurrences of G590A NAT2 SNP is detected or two occurrences of G857A NAT2 SNP is detected; or, (b) at least two SNPs selected from the group consisting of G191A NAT2 SNP, C282T NAT2 SNP, T341C NAT2 SNP, G590A NAT2 SNP and G857A NAT2 SNP are detected and said at least two SNPs reside on different chromosomes.

Embodiment 15. The method of embodiment 13 or 14, wherein the subject has a tuberculosis infection and the drug is isoniazid.

Embodiment 16. The method of embodiment 15, wherein the subject is an adult subject with tuberculosis and the prescribed dose is 5 mg/kg.

Embodiment 17. The method of embodiment 15, wherein the subject is a minor subject with tuberculosis and the prescribed dose is 10 mg/kg.

Embodiment 18. The method of embodiment 15, wherein the subject is an adult subject with drug-resistant tuberculosis and the prescribed dose is 15 mg/kg.

Embodiment 19. The method of embodiment 15, wherein the subject is an adult subject with a latent tuberculosis infection and the prescribed dose is 15 mg/kg.

Embodiment 20. A kit for determining acetylator type in a subject, said kit comprising nucleic acid probes to G191A NAT2 SNP, C282T NAT2 SNP, T341C NAT2 SNP, G590A NAT2 SNP and G857A NAT2 SNP.

Embodiment 21. The kit of embodiment 20, wherein said nucleic acid probe to G191A NAT2 SNP is SEQ ID NO:7.

Embodiment 22. The kit of embodiment 20 or 21, wherein said nucleic acid probe to C282T NAT2 SNP is SEQ ID NO:8.

Embodiment 23. The kit of any of embodiments 20 to 22, wherein said nucleic acid probe to T341C NAT2 SNP is SEQ ID NO:9.

Embodiment 24. The kit of any of embodiments 20 to 23, wherein said nucleic acid probe to G590A NAT2 SNP is SEQ ID NO:10.

Embodiment 25. The kit of any of embodiments 20 to 24, wherein said nucleic acid probe to G857A NAT2 SNP is SEQ ID NO:11.

Embodiment 26. The kit of any of embodiments 20 to 25, wherein at least one probe is labeled.

Embodiment 27. The kit of any of embodiments 20 to 26, further comprising amplification primers.

Embodiment 28. The kit of any of embodiments 20 to 27, further comprising a polymerase.

Embodiment 29. The kit of embodiment 28, wherein the polymerase is Aptataq exo-DNA polymerase.

What is claimed is:

1. A method of administering an arylamine drug or a hydrazine drug to a subject in need thereof, the method comprising assigning a NAT2 phenotype to the subject by a method comprising simultaneously detecting the nucleotide content at each allele of five unphased single nucleotide polymorphisms (SNPs) of N-acetyltransferase-2 (NAT2) in a biological sample of the subject in a 5-plex multiplex qPCR-based amplification and multicolor melt curve analysis (MMCA); and assigning, via implementation of a pretrained random forest algorithm, a NAT2 acetylation genotype and phenotype based on the detected unphased NAT2 SNPs;

wherein the alleles of the five NAT2 SNPs are 191A, 282T, 341C, 590A and 857A;

wherein the method does not comprise detecting additional alleles of NAT2 SNPs in the biological sample; and wherein the detecting comprises determining, for each allele of the five SNPs, whether the allele is present once, present more than once, or not present within the chromosomes of said subject; and detecting that none of the alleles of the five SNPs are present in the sample, and administering the arylamine drug or hydrazine drug to the subject at a dose greater than a prescribed dose; or detecting that at least two occurrences of one or more of the alleles of the five SNPs are present in the sample, and administering the arylamine drug or hydrazine drug at a dose less than a prescribed dose.

2. The method of claim 1, wherein said biological sample is a sputum sample, a saliva sample, a blood sample or a buccal sample.

3. The method of claim 1, wherein said subject has a tuberculosis infection.

4. The method of claim 3, wherein the tuberculosis infection is latent.

5. The method of claim 1, wherein the subject has a tuberculosis infection and the drug is isoniazid.

6. The method of claim 5, wherein the subject is an adult subject with tuberculosis and the prescribed dose is 5 mg/kg.

7. The method of claim 5, wherein the subject is a minor subject with tuberculosis and the prescribed dose is 10 mg/kg.

8. The method of claim 5, wherein the subject is an adult subject with drug-resistant tuberculosis and the prescribed dose is 15 mg/kg.

9. The method of claim 5, wherein the subject is an adult subject with a latent tuberculosis infection and the prescribed dose is 15 mg/kg.

10. The method of claim 1, wherein the method comprises simultaneous detection of *Mycobacterium tuberculosis* complex (MTBC) in the biological sample.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1

catggagttg ggcttagagg                                          20


<210> SEQ ID NO 2
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 2

agcttccaga cccagcatc                                           19


<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3

gtgccttgca ttttctgctt                                          20


<210> SEQ ID NO 4
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 4

gcaaggaaca aaatgatgtg g                                        21


<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 5
actgtttggt gggcttcatc 20

<210> SEQ ID NO 6
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 6
gagttgggtg atacatacac aagg 24

<210> SEQ ID NO 7
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 7
cggcgctgta agaagaaacc agggtgggtg gtgtgcgccg 40

<210> SEQ ID NO 8
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 8
cgcagcgtat ttttacatcc ctccagttaa caaatacagc gctgcg 46

<210> SEQ ID NO 9
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 9
ggcgagggtg accattgacg gcaggaatta cattgtctcg cc 42

<210> SEQ ID NO 10
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 10
gccgcgcgct tgaacctcaa acaattgaag attttgagtc gcggc 45

<210> SEQ ID NO 11
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 11
cgcggccaaa cctggtgatg aatcccttac tatttagaag ccgcg 45

<210> SEQ ID NO 12
<211> LENGTH: 19

-continued

```
<212> TYPE: DNA
<213> ORGANISM: Artificial Sequence
<220> FEATURE:
<223> OTHER INFORMATION: Synthetic Polynucleotide

<400> SEQUENCE: 12

gtcgaacggc tgatgacca                                                   19


<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 13

agcggcgctg gacgagat                                                    18


<210> SEQ ID NO 14
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 14

cgcagcgacc acgatcgctg atccggccac aggctgcg                              38


<210> SEQ ID NO 15
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 15

gggctgttcc ctttgaga                                                    18


<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 16

tagtgagttg ggtgatac                                                    18
```